(12) United States Patent
Jeschke et al.

(10) Patent No.: US 6,306,872 B1
(45) Date of Patent: Oct. 23, 2001

(54) 6-SUBSTITUTED 1,2,4A,5A,8A,8B-HEXAHYDRO- AND 1,2,3,4,4A,5A,8A,8B-OCTAHYDRO-6H-PYRROLO[3',4':4,5]FURO[3,2-B]PYRID-8(7H)-ONE DERIVATIVES AND THEIR USE IN COMBATTING ENDOPARASITES

(75) Inventors: Peter Jeschke, Leverkusen; Achim Harder, Köln; Norbert Mencke, Leverkusen; Georg von Samson-Himmelstjerna, Solingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/423,685

(22) PCT Filed: Apr. 29, 1998

(86) PCT No.: PCT/EP98/02511

§ 371 Date: Nov. 10, 1999

§ 102(e) Date: Nov. 10, 1999

(87) PCT Pub. No.: WO98/51688

PCT Pub. Date: Nov. 19, 1998

(30) Foreign Application Priority Data

May 12, 1997 (DE) .............................. 197 19 839

(51) Int. Cl.[7] .................. A61K 31/437; A61K 31/4355; C07D 491/147; A61P 33/00
(52) U.S. Cl. .............................. 514/293; 546/83; 546/16; 544/61; 544/121; 544/332; 544/361; 514/228.5; 514/232.8; 514/252.13; 514/275; 514/278

(58) Field of Search ................... 546/83, 16; 514/293, 514/228.5, 232.8, 252.15, 275, 278; 544/61, 121, 332, 361

(56) References Cited

FOREIGN PATENT DOCUMENTS

19538960 * 4/1997 (DE) .

* cited by examiner

Primary Examiner—Evelyn Mei Huang
(74) Attorney, Agent, or Firm—Joseph C. Gil; Godfried R. Akorli

(57) ABSTRACT

The present invention relates to 6-substituted 1,2,4a,5a,8a,8b-hexahydro- and 1,2,3,4,4a,5a,8a,8b-octahydro-6H-pyrrolo[3',4':4,5]furo[3,2-b]pyrid-8(7H)-one derivatives of the general formula (I) and their salts (I)

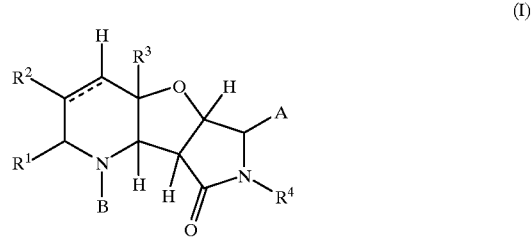

in which
the radicals $R^1$, $R^2$, $R^3$, $R^4$, B and A are each as defined in the description, to processes for their preparation and to their use for controlling endoparasites.

8 Claims, No Drawings

6-SUBSTITUTED 1,2,4A,5A,8A,8B-HEXAHYDRO- AND 1,2,3,4,4A,5A,8A,8B-OCTAHYDRO-6H-PYRROLO[3',4':4,5]FURO[3,2-B]PYRID-8(7H)-ONE DERIVATIVES AND THEIR USE IN COMBATTING ENDOPARASITES

This application is the national phase of PCT/EP98/02511, filed Apr. 29, 1998.

The present invention relates to 6-substituted 1,2,4a,5a, 8a,8b-hexahydro- and 1,2,3,4,4a,5a,8a,8b-octahydro-6H-pyrrolo[3',4':4,5]furo[3,2-b]pyrid-8(7H)-one derivatives, to their preparation and to their use for controlling endoparasites.

4a,5a,8a,8b-Tetrahydro-6H-pyrrolo[3',4':4,5]furo[3,2-b]pyrid-6,4(7H)-dione derivatives, their preparation and their use for controlling endoparasites is the subject matter of the earlier, published patent application German Offenlegungsschrift 19 538 960A1.

However, the novel 6-substituted 1,2,4a,5a,8a,8b-hexahydro- and 1,2,3,4,4a,5a,8a,8b-octahydro-6H-pyrrolo[3',4':4,5] furo[3,2-b]pyrid-8(7H)-one derivatives have hitherto not been disclosed.

The present invention relates to:
6-Substituted 1,2,4a,5a,8a,8b-hexahydro- and 1,2,3,4,4a, 5a,8a,8b-octahydro-6H-pyrrolo[3',4':4,5]furo[3,2-b] pyrid-8(7H)-one derivatives of the general formula (I) and their salts

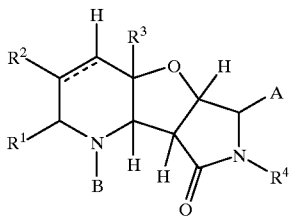

(I)

in which
R¹ represents hydrogen, straight-chain or branched alkyl, cycloalkyl, arylalkyl, aryl, heteroaryl, hetarylalkyl, which are optionally substituted,
R² represents hydrogen, straight-chain or branched alkyl, cycloalkyl, alkoxycarbonyl, which are optionally substituted,
R¹ and R² together with the atoms to which they are attached represent a 5- or 6-membered ring which may optionally be interrupted by oxygen, sulphur, sulphoxyl or sulphonyl and which is optionally substituted,
R³ represents hydrogen, straight-chain or branched alkyl, cycloalkyl or alkoxycarbonyl, which are optionally substituted,
R⁴ represents hydrogen, straight-chain or branched alkyl, alkenyl, alkinyl, cycloalkyl, cycloalkylalkyl, aryl, arylalkyl, hetaryl, hetarylalkyl, amino, alkylamino, dialkylamino, cycloalkylamino, which are optionally substituted,
A represents hydroxyl, alkoxy, alkenyloxy, alkinyloxy, arylalkyloxy, formyloxy, azido, halogen, aryloxy, hetarylalkyloxy, hetaryloxy, mercapto, alkylthio, alkylsulphonyl, alkenylthio, alkenylsulphonyl, alkinylthio, alkinylsulphonyl, arylalkylthio, arylalkylsulphonyl, hetarylalkylthio, hetarylalkylsulphonyl, arylthio, arylsulphonyl, alkyl, alkenyl, alkinyl, aryl, arylalkyl, hetaryl, hetarylalkyl, alkoxycarbonyl, which are optionally substituted, cyano, carbamoyl, thiocarbamoyl, or optionally represents a radical from the group consisting of A¹, A² and A³

(A¹)

(A²)

(A³)

in which
X represents oxygen or sulphur,

represents carboxyl, thiocarboxyl, sulphoxyl, sulphonyl, —P(O)—O—R⁵or —P(S)—O—R⁵, Q represents straight-chain or branched alkyl, alkenyl, alkinyl, cycloalkyl, alkoxy, alkenyloxy, alkinyloxy, aryl, arylalkyl, cycloalkoxy, hetaryl, hetarylalkyl, a cyclic amino group which is attached via nitrogen and which is optionally substituted, R⁵ represents alkyl, R⁶ represents hydrogen, alkyl, alkoxy, arylalkoxy, alkylthio, cycloalkylthio, arylthio, hetarylalkylthio, R⁷ represents alkyl, alkenyl, cycloalkyl, alkylthio, arylthio, aryl, arylalkyl, hetaryl or hetarylalkyl, which are optionally substituted, R⁶ and R⁷ together with the atoms to which they are attached represent a 5-, 6- or 7-membered carbocyclic ring, which may optionally be substituted, B represents hydrogen, straight-chain or branched alkyl, alkenyl, alkinyl, cycloalkyl, cycloalkylalkyl, aryl, arylalkyl, hetaryl, hetarylalkyl, which are optionally substituted, formyl, alkoxydicarbonyl or optionally represents a radical from the group consisting of B¹, B² B³ and B⁴

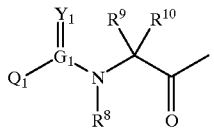

(B¹)

-continued

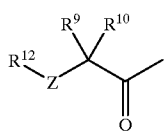
(B²)

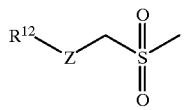
(B³)

(B⁴)

in which

R⁸ represents hydrogen, straight-chain or branched alkyl, cycloalkyl, aryl, arylalkyl, heteroaryl, heteroarylalkyl, which are optionally substituted, R⁸ and R⁹ together with the atoms to which they are attached represent a 5- or 6-membered ring which is optionally interrupted by oxygen, sulphur, suiphoxyl or sulphonyl and is optionally substituted, R⁹ and R¹⁰ independently of one another each represent hydrogen, straight-chain or branched alkyl alkenyl, cycloalkyl, and also represent optionally substituted aryl, arylalkyl, hetaryl, hetarylalkyl, or R⁹ and R¹⁰ together represent a spirocyclic ring, which is optionally substituted,

represents carboxyl, thiocarboxyl, —C=CH—NO₂, —C=CH—CN, —C=N—R¹¹ sulphoxyl, sulphonyl, —P(O)—O—R⁵ or —P(S)—O—R⁵, R¹¹ represents hydrogen, hydroxyl, alkoxy, alkylcarbonyl, alkoxycarbonyl, halogenoalkylcarbonyl, alkylsulphonyl, nitro or cyano, and Q¹ represents straight-chain or branched alkyl, alkenyl, alkinyl, cycloalkyl, aryl, arylalkyl, hetaryl or hetarylalkyl, which are optionally substituted, or optionally represents a radical from the group consisting of G¹ and G²

(G¹)

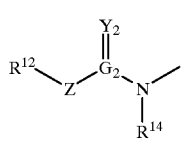
(G²)

in which

may represent carboxyl, thiocarboxyl or sulphonyl,

Z represents oxygen, sulphur or —R¹³,

R¹² may, if Z is nitrogen, represent a cyclic amino group which is attached via a nitrogen atom, R¹² and R¹³ independently of one another represent hydrogen, straight-chain or branched alkyl, alkenyl, alkinyl, cycloalkyl, cycloalkylalkyl, alkoxycarbonyl, aryl, arylalkyl, hetaryl, hetarylalkyl, which are optionally substituted, or R¹² and R¹³ together with the adjacent N atom represent a heterocyclic 5-, 6- or 7-membered ring system or represent a 7- to 10-membered bicyclic ring system, which may optionally also be interrupted by oxygen, sulphur, sulphoxyl, sulphonyl, carbonyl, —N—O, —N=, —NR¹⁵— or by quarternized nitrogen and which is optionally substituted, R¹⁴ represents hydrogen or alkyl, R¹⁵ represents hydrogen, straight-chain or branched alkyl, alkenyl, alkinyl, cycloalkyl, cycloalkylalkyl, alkoxycarbonyl, alkylcarbonyl, cycloalkylcarbonyl, cyano, aryl, arylalkyl, hetaryl, hetarylalkyl, which are optionally substituted.

Depending on the nature of the substituents, the compounds of the formula (1) can be present as geometrical and/or optical isomers or isomer mixtures of varying composition. The invention relates both to the pure isomers and to the isomer mixtures.

In the formula (I), the interrupted line together with the parallel bond may represent a single bond or a double bond between the carbon atom that carries the substituent R² and the adjacent carbon atom.

2. Process for preparing the novel 6-hydroxy-1,2,4a,5a, 8a,8b-hexahydro-6H-pyrrolo[3',4':4,5]furo[3,2-b] pyrid-8(7H)-one and/or 6-hydroxy-1,2,3,4,4a,5a,-8a, 8b-octahydro- 6H-pyrrolo[3',4':4,5]furo[3,2-b)pyrid-8 (7H)-one derivatives of the general formulae (Ia) and (Ib) and their salts

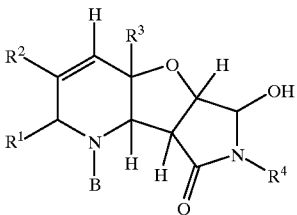
(Ia)

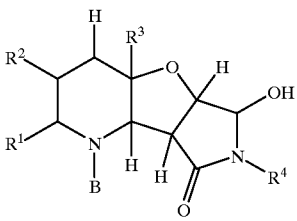
(Ib)

in which

R¹, R², R³, R⁴ and B are each as defined under 1, characterized in that the 1,2,4a,5a,8a,8b-hexahydro-6H-pyrrolo[3',4':4,5]furo[3,2-b]pyridine-6,8(7H)-dione and/or 1,2,3,4,4a,5a,8a,8b-octahydro-6H-pyrrolo[3',4':4,5]furo[3,2-b]-pyridine-6,8(7H)-dione derivatives of the general formulae (IIa) and (IIb) and their salts

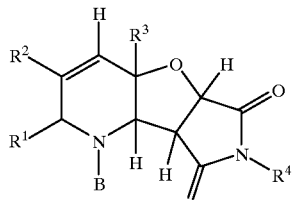
(IIa)

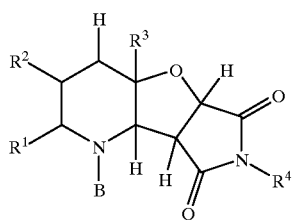
(IIb)

in which
R¹, R², R³, R⁴ and B are each as defined under 1 are hydrogenated in the presence of a suitable diluent, or that, in a first reaction step, the 1,2,4a,5a,8a,8b-hexahydro-6H-pyrrolo[3',4':4,5]furo[3,2-b]pyridine-6,8-(7H)-dione and/or 1,2,3,4,4a,5a,8a,8b-octahydro-6H-pyrrolo[3',4':4,5]furo-[3,2-b]pyridine-6,8(7H)-dione derivatives of the general formulae (IIc) and (IId) and their salts

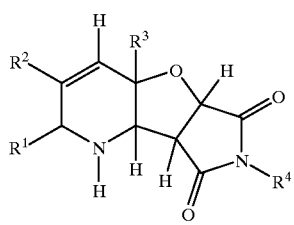
(IIc)

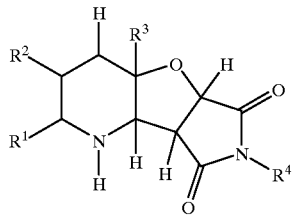
(IId)

in which
R¹, R², R³, R⁴ are each as defined under 1
are hydrogenated in the presence of a suitable diluent to give 6-hydroxy-1,2,4a,5a,8a,8b-hexahydro-6H-pyrrolo[3',4':4,5]furo[3,2-b]pyrid-8(7H)-one and/or 6-hydroxy-1,2,3,4,4a,5a,8a,8b-octahydro-6H-pyrrolo[3',4':4,5]furo[3,2-b]pyrid-8(7H)-one derivatives of the general formulae (Ic) and (Id)

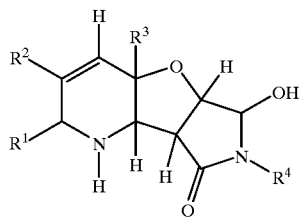
(Ic)

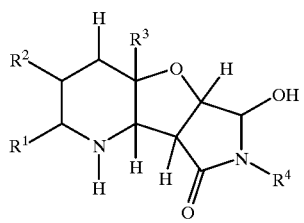
(Id)

in which
R¹, R², R³ and R⁴ are each as defined under 1, or that, for the selective preparation of the novel derivatives of the general formulae (IIa) and their salts, in a first reaction step the 4a,5a,8a,8b-tetrahydro-6H-pyrrolo[3',4':4,5]furo[3,2-b]pyridine-6,8(7H)-dione derivatives of the general formula (III) and their salts

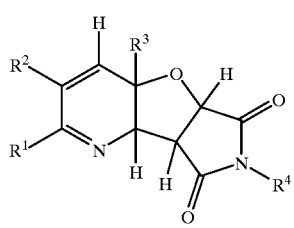
(III)

in which
R¹, R², R³ and R⁴ are each as defined under 1
are hydrogenated in the presence of a suitable diluent to give 6hydroxy-1,2,4a,5a,8a,8b-hexahydro-6H-pyrrolo[3',4':4,5]furo[3,2-b]pyrid-8(7H)-one derivatives of the general formula (Ic)

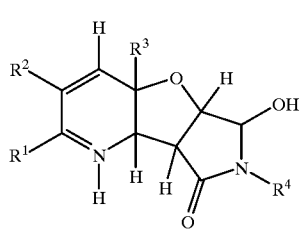
(Ic)

in which
R¹, R², R³ and R⁴ are each as defined under 1,
and, subsequently in a second reaction step, the derivatives of the general formulae (Ic) and (Id)

(Ic)

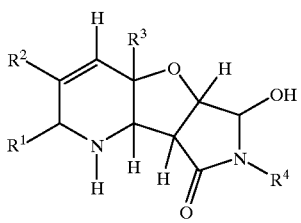

(Id)

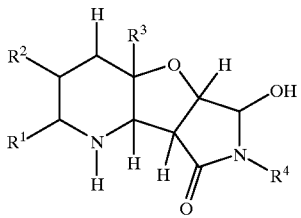

obtained in this manner
in which
R$^1$, R$^2$, R$^3$ and R$^4$ are each as defined under 1,
a) are reacted with compounds of the general formula (IV)

B—E     (IV)

in which
B is as defined above, and
E represents an electron-withdrawing leaving group,
if appropriate in the presence of diluents and if appropriate in the presence of a basic reaction auxiliary, or
b) are reacted with compounds of the general formula (V)

(V)

in which

and Q are each as defined under 1, and
W represents a suitable leaving group, such as, for example, halogen, alkoxy, alkylthio or aryloxy,
if appropriate in the presence of a catalyst, if appropriate in the presence of a basic reaction auxiliary and if appropriate in the presence of diluents, or that, to prepare the novel 6-hydroxy-1,2,4a,5a,8a,8b-hexahydro-6H-pyrrolo[3',4':4,5]furo[3,2-b]pyrid-(7H)-one and/or 6-hydroxy-1,2,3,4,4a,5a,8a,8b-octahydro-6H-pyrrolo-[3',4':4,5]furo[3,2-b]pyrid-(7H)-one derivatives of the general formulae (Ia) and (Ib) and their salts in which the group

represents carboxyl, the compounds of the formula (Ic) or (Id)
c) are reacted with a carboxylic anhydride of the general formula (VI)

(Q—C=O)$_2$O     (VI)

in which
Q is as defined under claim 1,
if appropriate in the presence of a catalyst, if appropriate in the presence of diluents, or that the compounds of the formula (Ic) or (Id)
d) are reacted with amino acid derivatives of the general formula (VII)

(VII)

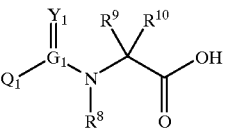

in which

Q$^1$, R$^8$, R$^9$ and R$^{10}$ are as defined under 1,
if appropriate in the presence of coupling agents and if appropriate in the presence of a basic reaction auxiliary, if appropriate in the presence of diluents, or that the compounds of the formula (Ic) or (Id)
e) are reacted with compounds of the general formulae (VIII) or (IX)

R$^{12}$—N=C=Y     (VIII)

(IX)

in which

Z and R$^{12}$ are each as defined under 1,
Y represents oxygen or sulphur,
if appropriate in the presence of a catalyst, if appropriate in the presence of diluents.
The invention furthermore relates to:
3. Process for preparing 6-substituted 1,2,4a,5a,8a,8b-hexahydro-6H-pyrrolo-[3',4':4,5]furo[3,2-b]pyrid-8

(7H)-one and/or 6-substituted 1,2,3,4,4a,5a,8a,8b-octahydro-6H-pyrrolo[3',4':4,5]furo[3,2-b]pyrid-8 (7H)-one derivatives of the general formulae (Ie) and (If) and their salts (Ie)

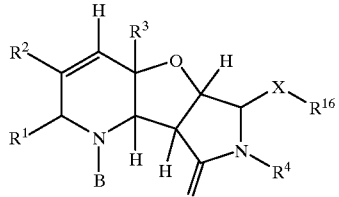

(If)

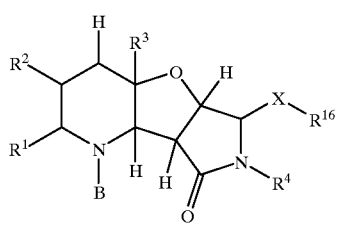

in which
R$^1$, R$^2$, R$^3$, R$^4$ and B are each as defined under 1,
X represents oxygen, sulphur or sulphonyl,
R$^{16}$ represents alkyl, alkenyl, alkinyl, arylalkyl, aryl, hetarylalkyl, hetaryl, which are optionally substituted, or
optionally represents the group

in which
G, Y and Q are each as defined under 1,
and their optical isomers and racemates,
characterized in that
a) the derivatives of the general formulae (Ia) and (Ib) obtainable according to claim 2 and their salts (Ia)

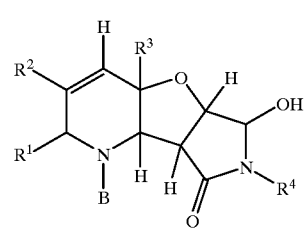

(Ib)

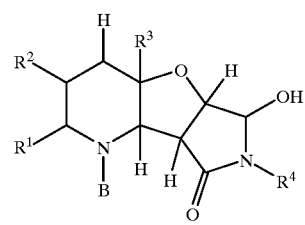

in which
R$^1$, R$^2$, R$^3$, R$^4$ and B are each as defined under 1 are reacted with compounds of the general formula (X)

H-X-R$^{16}$ (X)

in which
R$^{16}$ and X are each as defined above,
if appropriate in the presence of an acid, if appropriate in the presence of diluents, or that
b) to prepare the novel 6-substituted 1,2,4a,5a,8a,8b-hexahydro-6H-pyrrolo[3',4':4,5]furo[3,2-b]pyrid-8 (7H)-one and/or 6-substituted 1,2,3,4,4a,5a,8a,8b-octahydro-6H-pyrrolo[3,4t:4,5]furo[3,2-b]pyrid-8 (7H)-one derivatives of the general formulae (Ie) and (If) and their salts,
in which the radical R$^{16}$ represents the group

in which

and Q are each as defined under 1,
they are reacted with the compounds of the general formula (V)

(V)

in which

and Q are each as defined under 1, and
W is as defined under 3b),
if appropriate in the presence of a catalyst, if appropriate in the presence of a basic reaction auxiliary and if appropriate in the presence of diluents, or that
c) to prepare the novel derivatives of the general formulae (Ie) and (If) and their salts,
in which the group

represents carboxyl,
they are reacted with a carboxylic anhydride of the general formula (VI)

(Q—C=O)$_2$O (VI)

in which

Q is as defined under 1, if appropriate in the presence of a catalyst, if appropriate in the presence of diluents, or that d) they are reacted with compounds of the general formulae (VIII) or (IX)

$$R^{12}-N=C=Y \quad \text{(VIII)}$$

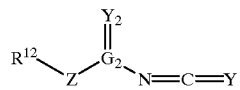
(IX)

in which

Z, Y and $R^{12}$ are each as defined under 1, if appropriate in the presence of a catalyst, if appropriate in the presence of diluents, or that e) to prepare the novel 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one derivatives of the general formulae (Ie) and (If) and their salts

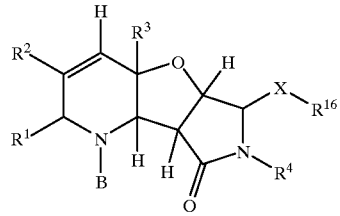
(Ie)

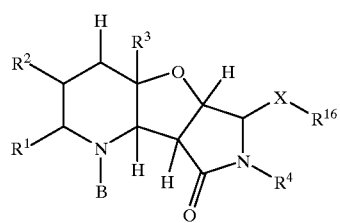
(If)

in which $R^1$, $R^2$, $R^3$, $R^4$, X and B are as defined under 1 and the radicals B and $R^{16}$
represent the same group

in which

and Q are each as defined under 1,
derivatives of the general formulae (Ic) and (Id)

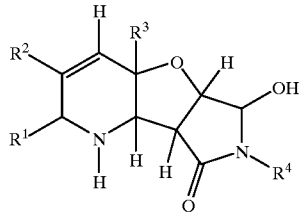
(Ic)

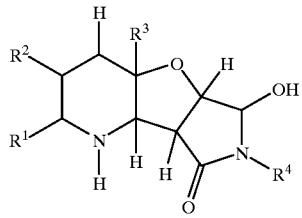
(Id)

in which
$R^1$, $R^2$, $R^3$, $R^4$ are each as defined under 3
are reacted with acylating agents of the formula (IV)

$$\text{E-B} \quad \text{(IV)}$$

and/or $$\text{E-R}^{16}$$

either on the radical —NH— in position 1 or on the radical —OH in position 6 or on both radicals, where E-B and/or E-$R^{16}$ are one of the compounds of the general formulae (V), (VI), (VII) or (IX) below

(V)

$$(Q-C=O)_2O \quad \text{(VI)}$$

$$R^{12}-N=C=Y \quad \text{(VIII)}$$

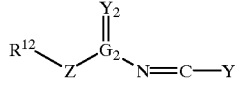
(IX)

in which

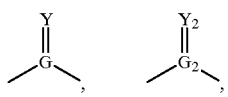

Q, Z, W and $R^2$ are each as defined under 1 and 2;
the reaction being carried out, if appropriate, in the presence of a catalyst, if appropriate in the presence of a basic reaction auxiliary and if appropriate in the presence of diluents, f) to prepare the novel 6-substituted 1,2,4a,5a,8a,8b-hexahydro-6H-pyrrolo[53',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one derivatives of the general formulae (Ie) and (If) and their salts,

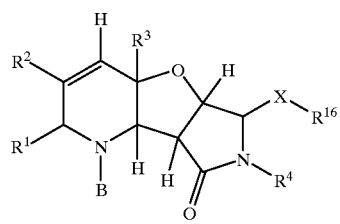

(Ie)

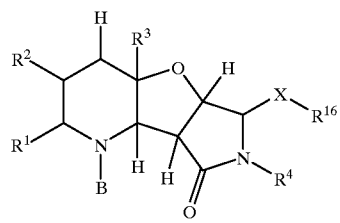

(If)

in which
$R^1, R^2, R^3, R^4$, X and B are each as defined under I and the radical $R^{16}$ represents
the group

in which

and Q are each as defined under 1, derivatives of the general formulae (Ic) and (Id)

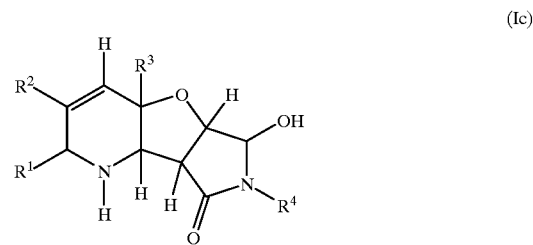

(Ic)

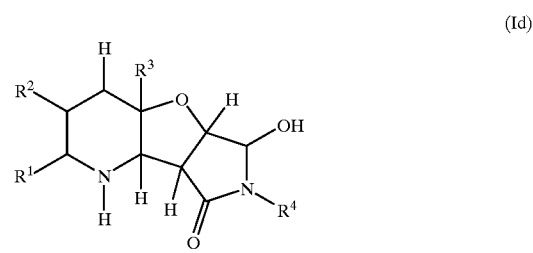

(Id)

in which
$R^1, R^2, R^3, R^4$ are each as defined under 3,
are reacted with an acylating agent of the formula (WV)

$$E-R^6 \qquad (IV)$$

on the radical —OH in position 6, where E—$R^{16}$ represents the compound of the general formula (VII)

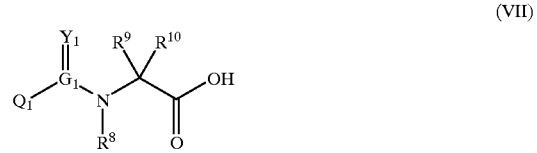

(VII)

in which

$Q^1, R^8, R^9$ and $R^{10}$ are each as defined under 1 and 2; and subsequently, in a second reaction step, the derivatives of the general formulae (Ig) and (Ih)

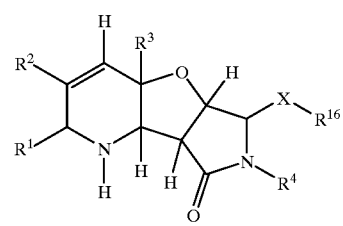

(Ig)

-continued

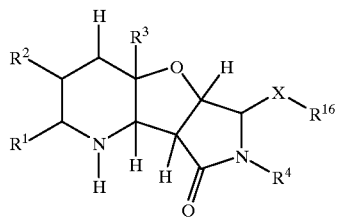
(Ih)

obtained in this manner
in which
$R^1$, $R^2$, $R^3$, $R^4$ and X are each as defined under 1 and
the radical $R^{16}$ represents the group

in which

and Q are each as defined under 1,
are reacted with an acylating agent of the formula (IV)

E—B  (IV)

on the radical —NH— in position 1, where E-B is one
of the compounds of the general formulae (V), (VI),
(VII) or (IX) mentioned under 3e
in which

Q, Z, W, and $R^{12}$ are each as defined under 1 and 2;
the reaction being carried out, if appropriate, in the
presence of a catalyst, if appropriate in the presence
of a basic reaction auxiliary and if appropriate in the
presence of diluents.

4. Process for preparing the 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one derivatives of the general formulae (Ii) and (Ij) and their salts

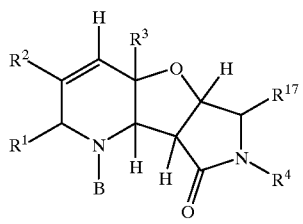
(Ii)

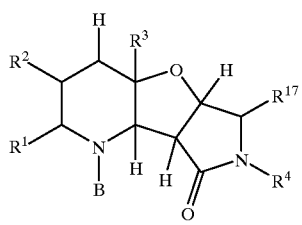
(Ij)

in which
$R^1$, $R^2$, $R^3$, $R^4$ and B are each as defined under 1,
$R^{17}$ represents alkyl, alkenyl, alkinyl, aryl, arylalkyl, hetaryl, hetarylalkyl, cyano, alkoxycarbonyl, carbamoyl, thiocarbamoyl, which are optionally substituted, or optionally represents a radical from the group $A^2$

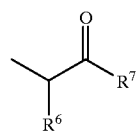
($A^2$)

in which
$R^6$ and $R^7$ are each as defined above under 1,
and their optical isomers and racemates,
characterized in that
either the derivatives of the general formulae (Ia) and (Ib)

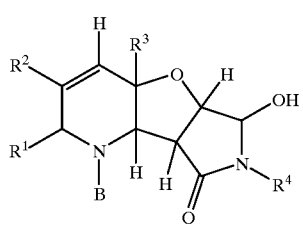
(Ia)

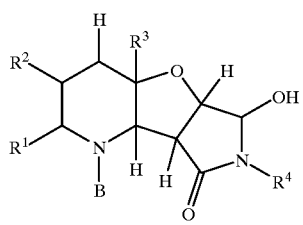
(Ib)

which are obtainable, for example, according to process 2
in which
$R^1$, $R^2$, $R^3$, $R^4$ and B are each as defined under 1, or
particularly preferably the derivatives of the general formulae (Ie) and (If)

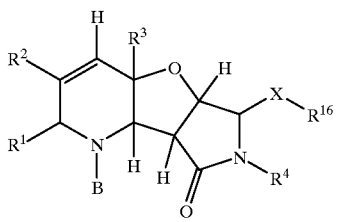
(Ie)

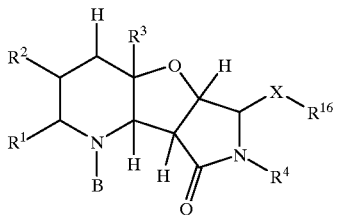
(If)

which are obtainable, for example, according to claim 3 in which

R$^1$, R$^2$, R$^3$, R$^4$ and B are each as defined under 4 and

R$^{16}$ represents alkyl, arylalkyl, aryl or acyl, which are optionally substituted, X represents oxygen, sulphur or sulphonyl, a) are reacted with organometallic compounds of the general formula (XI)

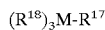
(XI)

in which

R$^{18}$ represents C$_{1-4}$-alkyl,

M represents a metal atom, in particular silicon or tin,

R$^{17}$ represents alkyl, alkenyl, cycloalkenyl, alkinyl, arylalkyl, hetarylalkyl, which are optionally substituted, or represents cyano, if appropriate in the presence of diluents and if appropriate in the presence of a catalyst, or b) are reacted with compounds of the general formula (XII)

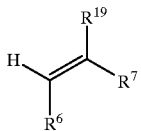
(XII)

in which

R$^6$ and R$^7$ are each as defined above,

R$^{19}$ represents hydrogen, —O-acyl, —O—Sn—O—SO$_2$—CF$_3$, —O—B(CH$_2$—CH$_3$)$_2$, or represents the radicals
—O—M(R$^{18}$)$_3$ and

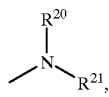

in which

M and R$^{18}$ are each as defined above under 4a), and

R$^{20}$ and R$^{21}$ independently of one another each represent hydrogen, straight-chain or branched alkyl, alkenyl, alkinyl, cycloalkyl, cycloalkylalkyl, arylalkyl, which are optionally substituted, or R$^{20}$ and R$^{21}$ together with the adjacent N atom represent a heterocyclic 5-, 6- or 7-membered ring system, which may optionally also be interrupted by oxygen, sulphur or nitrogen and which is optionally substituted, if appropriate in the presence of a catalyst and if appropriate in the presence of diluents, or c) are reacted with aromatics or heteroaromatics of the general formula (XIII)

 H-R$^{17}$ (XIII)

in which

R$^{17}$ represents aryl or hetaryl, which are optionally substituted, if appropriate in the presence of a catalyst and if appropriate in the presence of diluents.

The general formula (I) provides a general definition of the 6-substituted 1,2,4a,5a,8a,8b-hexahydro- and 1,2,3,4,4a,5a,8a,8b-octahydro-6H-pyrrolo[3',4':4,5]-furo[3,2-b]pyrid-8(7H)-one derivatives according to the invention and their salts.

The 6-substituted 1,2,4a,5a,8a,8b-hexahydro- and 1,2,3,4,4a,5a,8a,8b-octahydro-6H-pyrrolo[3',4':4,5]furo[3,2-b] pyrid-8(7H)-one derivatives according to the invention and their acid addition salts and metal salt complexes have good endoparasiticidal, in particular anthelmintic action and can preferably be employed in the field of veterinary medicine.

Optionally substituted alkyl on its own or as part of a radical in the general formulae means straight-chain or branched alkyl having preferably 1 to 6, in particular 1 to 4, carbon atoms. Examples which may be mentioned are optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl.

Methyl, ethyl, n-propyl, isopropyl, n-butyl, isobutyl, sec-butyl and tert-butyl may be mentioned as being preferred.

Optionally substituted alkenyl on its own or as part of a radical in the general formulae means straight-chain or branched alkenyl having preferably 1 to 6, in particular 1 to 4, carbon atoms. Examples which may be mentioned are optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, I-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4pentenyl, 1,1-dimethyl-2-butenyl, 1,1-dimethyl-3-butenyl, 1,2-dimethyl-2-butenyl, 1,2-dimethyl-3-butenyl, 1 ,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1-trimethyl-2- propenyl, 1-ethyl-1-methyl-2-propenyl and 1-ethyl-2-methyl-2-propenyl.

Ethenyl, 2-propenyl, 2-butenyl and 1-methyl-2-propenyl may be mentioned as being preferred.

Optionally substituted alkinyl on its own or as part of a radical in the general formulae is straight-chain or branched alkinyl having preferably 1 to 6, in particular 1 to 4, carbon atoms. Examples which may be mentioned are ethinyl, 2-propinyl, 2-butinyl, 3-butinyl, 1-methyl-2-propinyl, 2-pentinyl, 3-pentinyl, 4-pentinyl, 1-methyl-3-butinyl, 2-methyl-3-butinyl, 1-methyl-2-butinyl, 11-dimethyl-2-propinyl, 1-ethyl-2-propinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-4-pentinyl, 4-methyl-2-pentinyl, 1,1-dimethyl-3-butinyl, 1,2-dimethyl-3-butinyl, 2,2-dimethyl-3-butinyl, 1-ethyl-3-butinyl, 2-ethyl-3-butinyl and 1-ethyl-i-methyl-2-propinyl.

Ethinyl, 2-propinyl and 2-butinyl may be mentioned as being preferred.

Optionally substituted cycloalkyl on its own or as part of a radical in the general formulae means mono-, bi- and tricyclic cycloalkyl having preferably 3 to 10, in particular 3, 5 or 7, carbon atoms. Examples which may be mentioned are optionally substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Halogenoalkyl on its own or as part of a radical in the general formulae contains 1 to 4, in particular 1 or 2, carbon atoms having preferably 1 to 9, in particular 1 to 5, identical or different halogen atoms, preferably fluorine, chlorine or bromine, in particular fluorine and chlorine. Examples which may be mentioned are trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl.

Optionally substituted alkoxy on its own or as part of a radical in the general formulae means straight-chain or branched alkoxy having preferably I to 6, in particular 1 to 4, carbon atoms. Examples which may be mentioned are optionally substituted methoxy, ethoxy, n-propoxy, isopropoxy, n-butoxy, isobutoxy, sec-butoxy und tert-butoxy.

Optionally substituted halogenoalkoxy on its own or as part of a radical in the general formula means straight-chain or branched halogenoalkoxy having preferably 1 to 6, in particular 1 to 4, carbon atoms. Examples which may be mentioned are optionally substituted difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy.

Optionally substituted alkylthio on its own or as part of a radical in the general formulae means straight-chain or branched alkylthio having preferably 1 to 6, in particular 1 to 4, carbon atoms. Examples which may be mentioned are optionally substituted methylthio, ethylthio, n-propylthio, isopropylthio, n-butylthio, isobutylthio, sec-butylthio and tert-butylthio.

Optionally substituted halogenoalkylthio on its own or as part of a radical in the general formulae means straight-chain or branched halogenoalkylthio having preferably 1 to 6, in particular 1 to 4, carbon atoms. Examples which may be mentioned are optionally substituted difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio and 2-chloro-1,1,2-trifluoroethylthio.

Optionally substituted alkylcarbonyl on its own or as part of a radical in the general formulae means straight-chain or branched alkylcarbonyl having preferably 1 to 6, in particular 1 to 4, carbon atoms. Examples which may be mentioned are optionally substituted methylcarbonyl) ethylcarbonyl, n-propylcarbonyl, isopropylcarbonyl, sec-butylcarbonyl and tert-butylcarbonyl.

Optionally substituted cycloalkylcarbonyl on its own or as part of a radical in the general formulae means mono-, bi- and tricyclic cycloalkylcarbonyl having preferably 3 to 10, in particular 3, 5 or 7, carbon atoms. Examples which may be mentioned are optionally substituted cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl and adamantylcarbonyl.

Optionally substituted alkoxycarbonyl on its own or as part of a radical in the general formulae means straight-chain or branched alkoxy having preferably I to 6, in particular 1 to 4, carbon atoms. Examples which may be mentioned are optionally substituted methoxycarbonyl, ethoxycarbonyl, n-propoxycarbonyl, iso-propoxycarbonyl, n-butoxycarbonyl, isobutoxycarbonyl, sec-butoxycarbonyl and tert-butoxycarbonyl.

Aryl is, for example, a mono-, di- or polycyclic aromatic radical, such as phenyl, naphthyl, tetrahydronaphthyl, indanyl, fluorenyl and the like, but preferably phenyl or naphthyl.

Optionally substituted aryl in the general formulae preferably means optionally substituted phenyl or naphthyl, in particular phenyl.

Optionally substituted arylalkyl in the general formulae preferably means arylalkyl having preferably 6 or 10, in particular 8, carbon atoms in the aryl moiety (preferably phenyl or naphthyl, in particular phenyl) and preferably 1 to 4, in particular 1 or 2, carbon atoms in the alkyl moiety, where the alkyl moiety may be straight-chain or branched, which is optionally substituted in the aryl and/or alkyl moiety. Optionally substituted benzyl and phenylethyl may be mentioned by way of example and as being preferred.

The optionally substituted radicals of the general formulae may carry one or more, preferably 1 to 3, in particular 1 to 2, identical or different substituents. The following substituents may be mentioned by way of example and as being preferred: alkyl having preferably 1 to 4, in particular 1 to 2, carbon atoms, such as methyl, ethyl, n-propyl, isopropyl, n-butyl, isobutyl, sec-butyl and tert butyl; alkoxy having preferably 1 to 4, in particular 1 to 2, carbon atoms, such as methoxy, ethoxy, n-propoxy, isopropoxy, n-butoxy, isobutoxy, sec-butoxy and tert-butoxy; alkylthio, such as methylthio, ethylthio, n-propylthio, isopropylthio, n-butylthio, isobutylthio, sec-butylthio; halogenoalkyl having preferably 1 to 5, in particular 1 to 3, halogen atoms, where the halogen atoms are identical or different and are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkyl- and dialkylamino having preferably 1 to 4, in particular 1 or 2, carbon atoms per alkyl group, such as methylamino, methylethylamino, dimethylamino, n-propylamino, isopropylamino, methyl-n- butylamino; alkylcarbonyl radicals, such as methylcarbonyl; alkoxycarbonyl having preferably 2 to 4, in particular 2 to 3, carbon atoms, such as methoxycarbonyl and ethoxycarbonyl; alkylsulphinyl having 1 to 4, in particular 1 or 2, carbon atoms; halogenoalkylsulphinyl having 1 to 4, in particular 1 or 2, carbon atoms and 1 to 5 halogen atoms, such as trifluoromethylsulphinyl; halogenoalkylsulphonyl having 1 to 4, in particular 1 or 2, carbon atoms and 1 to 5 halogen atoms, such as trifluoromethylsulphonyl, perfluoro-n-butylsulphonyl, perfluoroisobutylsulphonyl; arylsulphonyl having preferably 6 or 10 aryl carbon atoms, such as phenylsulphonyl; trialkylsilyl having 1 to 4, in particular 1 or 2, carbon atoms, such as trimethfysilyl or triethylsilyl, acyl, aryl, aryloxy, which for their part may carry one of the abovementioned substituents, and the formimino radical (—HC=N—O-alkyl).

Suitable cyclic amino groups are heteroaromatic or aliphatic ring systems having one or more nitrogen atoms as heteroatoms, where the heterocycles may be saturated or unsaturated and may be one ring system or a plurality of fused ring systems, and optionally contain further heteroatoms, such as nitrogen, oxygen and sulphur, etc. Moreover, cyclic amino groups may also mean a spiral ring or bridged ring system. The number of atoms which form the cyclic amino groups is not limited, in the case of a one-ring system, for example, it is from 3 to 8 atoms and in the case of a three-ring system, it is from 7 to 11 atoms.

Examples of cyclic amino groups having saturated and unsaturated monocyclic groups with a nitrogen atom as heteroatom which may be mentioned are 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl, homopiperidino; examples of cyclic amino groups having saturated and unsaturated monocyclic groups having 2 or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl, 1,4-diaza-cyclo-heptan-1-yl; examples of cyclic amino groups having saturated and unsaturated monocyclic groups having 1 to 3 nitrogen atoms and 1 to 2 sulphur atoms as heteroatoms which may be mentioned are thiazolidin-3-yl, isothiazolin-2-yl, thiomorpholino, or dioxothiomorpholino; examples of cyclic amino groups having saturated and unsaturated fused cyclic groups which may be mentioned are indol-1-yl, 1,2-dihydrobenzimidazol-1-yl, perhydropyrrolo[1,2-a]pyrazin-2-yl; examples of cyclic amino groups having spirocyclic groups which may be mentioned are 2-azaspiro[4,5]decan-2-yl; examples of cyclic amino groups having bridged heterocyclic groups which may be mentioned are 2-azabicyclo[2,2,1]heptan-7-yl.

Preference is given to compounds: of the general formula (I) and their salts

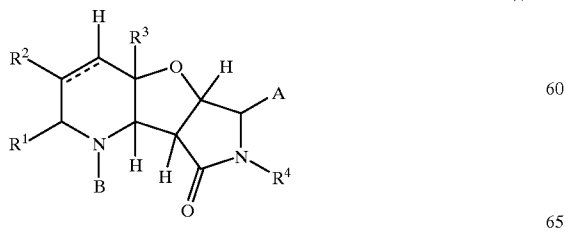

(I)

in which $R^1$ represents hydrogen, straight-chain or branched $C_{1-4}$-alkyl, in particular methyl, ethyl, propyl, isopropyl, isobutyl, sec-butyl, tert-butyl, $C_{3-6}$-cycloalkyl, in particular cyclopropyl, cyclobutyl, cyclopentyl, cyclohexyl, aryl or heteroaryl, which are optionally substituted, aryl-$C_{1-2}$-alkyl or hetaryl-$C_{1-2}$-alkyl, which are optionally substituted, $R^1$ and $R^2$ together with the atoms to which they are attached represent a 5- or 6-membered ring, which is optionally substituted, $R^2$ and $R^3$ independently of one another each represent hydrogen, straight-chain or branched $C_{1-4}$-alkyl, in particular methyl, ethyl, propyl, isopropyl, isobutyl, sec-butyl, tert-butyl, halogeno-$C_{1-4}$-alkyl, in particular bromomethyl, chloromethyl, difluoromethyl, trichloromethyl or trifluoromethyl, hydroxy-$C_{1-4}$-alkyl, in particular hydroxymethyl, $C_{1-4}$-alkanoyloxy-$C_{1-4}$-alkyl, in particular acetoxymethyl, $C_{1-2}$-alkoxy-$C_{1-4}$-alkyl, in particular methoxymethyl, $C_{1-2}$-alkylthio-$C_{1-4}$-alkyl, in particular methylthiomethyl, $C_{1-2}$-alkylsulphinyl-$C_{1-4}$-alkyl, in particular methylsulphinylmethyl, $C_{1-2}$-alkylsulphonylalkyl, in particular methylsulphonylmethyl, amino-$C_{1-2}$-alkyl, in particular aminomethyl, $C_{1-6}$-alkylamino-$C_{1-6}$-alkyl, in particular N-methylaminomethyl, $C_{1-6}$-dialkylamino-$C_{1-6}$-alkyl, heterocyclyl-$C_{1-6}$-alkyl, in particular N,N-dimethylaminomethyl, $C_3$6-cycloalkylaminoalkyl, in particular $C_{3-6}$-cycloalkyl, in particular cyclopropyl, cyclobutyl, $C_{1-4}$-alkoxycarbonyl, in particular methoxycarbonyl, ethoxycarbonyl, $R^4$ represents hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, halogeno-$C_{1-6}$-alkyl, in particular fluoromethyl, difluoromethyl, difluorochloromethyl, trifluoromethyl, trichloromethyl, 1-fluoroethyl, trifluoroethyl, 2-chloro-1,1,2-trifluoroethyl, hydroxy-$C_{1-4}$-alkyl, in particular hydroxymethyl, hydroxyethyl, $C_{1-4}$-alkanoyloxy-$C_{1-4}$-alkyl, in particular acetoxymethyl, acetoxyethyl, 2-acetoxypropyl, $C_{1-2}$-alkoxy-$C_{1-4}$-alkyl, in particular methoxymethyl, methoxyethyl, 2-methoxypropyl, $C_{1-4}$-alkoxycarbonyl-$C_{1-4}$-alkyl, in particular methoxycarbonylmethyl, ethoxycarbonylmethyl, tert-butyloxycarbonylmethyl, amino, amino-$C_{1-6}$-alkyl, in particular aminomethyl, aminoethyl, 2-aminopropyl, $C_{1-6}$-alkylamino-$C_{1-6}$-alkyl, in particular N-methylaminomethyl, N-methylaminoethyl, $C_{1-6}$-dialkylamino-$C_{1-6}$-alkyl, in particular N,N-dimethylaminomethyl, N,N-dimethylaminoethyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_2$6-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, $C_{3-6}$-cycloalkyl, in particular cyclopropyl, cyclobutyl, cyclopentyl, cyclohexyl, $C_{3-6}$-cycloalkyl-$C_{1-2}$-alkyl, in particular cyclopropylmethyl, cyclobutylmethyl, cyclopentylmethyl, cyclohexylmethyl, aryl, in particular phenyl, aryl-$C_{1-2}$-alkyl, in particular benzyl, 1-phenylethyl, 2-phenylethyl, hetaryl, in particular pyridyl, thiazolyl, N-morpholinyl, hetaryl-$C_{1-2}$-alkyl, in particular pyridylmethyl, indolylethyl and thiazolylmethyl, which are optionally substituted by radicals from the group consisting of halogen, in particular fluorine, chlorine, bromine or iodine, $C_{1-4}$-alkyl, in particular methyl, ethyl, isopropyl, sec-butyl, tert-butyl, halogeno-$C_{1-4}$-alkyl, in particular trifluoromethyl, trichloromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl; $R^4$ may furthermore represent $C_{1-4}$-alkylamino, di($C_{1-4}$)-alkylamino or $C_{3-7}$-cycloalkylamino;

A represents hydroxyl, $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_2$6-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_2$-6-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, $C_3$6-cycloalkyl, in particular cyclopropyl, cyclobutyl, cyclopentyl, cyclohexyl, $C_{3-6}$-cycloalkyl-$C_{1-2}$-alkyl, in particular cyclopropylmethyl, cyclobutylmethyl, cyclopentylmethyl, cyclohexylmethyl, $C_{1-6}$-alkoxy, in particular methoxy, ethoxy, propoxy, isopropoxy, isobutoxy, sec-butoxy, tert-butoxy, pentoxy, 1-methylbutoxy, 2-methylbutoxy, 3-methylbutoxy, 1,2dimethylpropoxy, 1,1-dimethylpropoxy, 2,2-dimethylpropoxy, 1-ethylpropoxy, hexoxy, 1l-methylpentoxy, $C_{2-6}$-alkenyloxy, in particular vinyloxy, 2-propenyloxy, 2-butenyloxy, 3-butenyloxy, 1-methyl-2-propenyloxy, 2-methyl-2-propenyloxy, 2-pentenyloxy, 1-methylbutenyloxy, 2-methyl-2-butenyloxy, 3-methyl-2-butenyloxy, 1-methyl-3-butenyloxy, 1,1-dimethyl-2-propenyloxy, 1,2-dimethyl-2-propenyloxy, 1-ethyl-2-propenyloxy, 2-hexenyloxy, $C_{2-4}$-alkinyloxy, in particular ethinyloxy, 2-propinyloxy, 2-butinyloxy, 3-butinyloxy, 1-methyl-2-propinyloxy, 2-pentinyloxy, 1-methyl-3-butinyloxy, 2-methyl-3-butinyloxy, 1,1-dimethyl-2-propinyloxy, $C_{1-4}$-alkoxycarbonyl, in particular methoxycarbonyl, ethoxycarbonyl, isopropyloxycarbonyl, tert-butyloxycarbonyl, mercapto, $C_{1-4}$-alkylthio, in particular methylthio, ethylthio, propylthio, isopropylthio, isobutylthio, sec-butylthio, tert-butylthio, $C_{2-4}$-alkenylthio, in particular vinylthio, 2-propenylthio, 2-butenylthio, 3-butenylthio, 1-methyl-2-propenylthio, 2-methyl-2-propenylthio, $C_{2-6}$-alkinylthio, in particular ethinylthio, 2-propinylthio, 2-butinylthio, 3-butinylthio, cyano, carbamoyl, thiocarbamoyl, aryl-$C_{1-2}$-alkyloxy, in particular benzyloxy, 1-phenylethyloxy, 2-phenylethyloxy, aryloxy, in particular phenoxy, hetaryl-$C_{1-2}$-alkyloxy, in particular pyridylmethoxy and thiazolylmethoxy, hetaryloxy, aryl-$C_{1-2}$-alkylthio, in particular benzylthio, 1-phenylethylthio, 2-phenylethylthio, hetaryl-$C_{1-2}$-alkylthio, in particular pyridylmethylthio and thiazolylmethylthio, aryl, in particular phenyl, aryl-$C_{1-2}$-alkyl, in particular benzyl, 1-phenylethyl, 2-phenylethyl, hetaryl, in particular pyridyl, furyl, thienyl, thiazolyl, N-morpholinyl, hetaryl-$C_{1-2}$-alkyl, in particular pyridylmethyl and thiazolylmethyl, which may optionally be substituted by radicals from a group consisting of halogen, in particular fluorine, chlorine, bromine or iodine, $C_{1-4}$-alkyl, in particular methyl, ethyl, isopropyl, sec-butyl, tert-butyl, halogeno-$CI_4$-alkyl, in particular trifluoromethyl, trichloromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C]A$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl, trialkylsilyl, in particular trimethylsilyl, or optionally represents a radical from the group consisting of $A^1$, $A^2$ and $A^3$

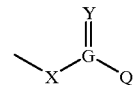

(A¹)

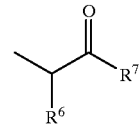

(A²)

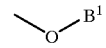

(A³)

in which

X represents oxygen or sulphur,

represents carboxyl, thiocarboxyl, sulphoxyl, sulphonyl, —P(O)—O—$R^5$ or —P(S)—O—$R^5$, Q represents straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_2$4-alkinyl, in particular ethinyl, 2-propinyl, 2-butinyl, 3-butinyl, I-methyl-2-propinyl, 2-pentinyl, 1-methyl-3-butinyl, 2-methyl-3-butinyl, 1,1-dimethyl-2-propinyl, $C_{3-6}$-cycloalkyl, in particular cyclopropyl, cyclobutyl, cyclopentyl, cyclohexyl, $C_{3-6}$-cycloalkoxy, in particular cyclopropyloxy, cyclobutyloxy, cyclopentyloxy, cyclohexyloxy, $C_{1-6}$-alkoxy, $C_{2-6}$-alkenyloxy, in particular methoxy, ethoxy, propoxy, isopropoxy, isobutoxy, sec-butoxy, tert-butoxy, pentoxy, 1-methylbutoxy, 2-methylbutoxy, 3-methylbutoxy, 1,2-dimethylpropoxy, 1,1-dimethylpropoxy, 2,2-dimethylpropoxy, 1-ethylpropoxy, hexoxy, I -methylpentoxy, $C_{2-6}$-alkinyloxy, in particular vinyloxy, 2-propenyloxy, 2-butenyloxy, 3-butenyloxy, 1-methyl-2-propenyloxy, 2-methyl-2-propenyloxy, 2-pentenyloxy, 1-methyl-2-butenyloxy, 2-methyl-2-butenyloxy, 3-methyl-2-butenyloxy, 1-methyl-3-butenyloxy, 1,1-dimethyl-2-propenyloxy, 1,2-dimethyl-2-propenyloxy, 1-ethyl-2-propenyloxy, 2-hexenyloxy, $C_{2-6}$-alkinyloxy, in particular ethinyloxy, 2-propinyloxy, 2-butinyloxy, 3-butinyloxy, 1-methyl-2-propinyloxy, 2-pentinyloxy, 1-methyl-3-butinyloxy, 2-methyl-3-butinyloxy, 1,1-dimethyl-2-propinyloxy, $C_{14}$-alkylamino, in particular N-methylamino, N-ethylamino, $C_{1-4}$-dialkylamino, in particular N,N-dimethylamino, N,N-diethylamino, a cyclic amino group which is attached via nitrogen, in particular morpholino, thiomorpholino, piperazino, piperidino, pyrrolidino, aryl, in particular phenyl, aryloxy, in particular phenoxy, aryl-$C_{1-2}$-alkyl, in particular benzyl, 1-phenylethyl, 2-phenylethyl, aryl-$C_{1-2}$-alkyloxy, in particular benzyloxy, 1-phenylethyloxy, 2-phenylethyloxy, hetaryl, in particular pyridyl, thiazolyl, hetaryl-$C_{1-2}$-alkyl, in particular pyridylmethyl or thiazolylmethyl, which are optionally substituted, $R^5$ represents $C_{1-4}$-alkyl, in particular methyl or ethyl, $R^6$ represents hydrogen or $C_{1-4}$-alkyl, in particular methyl, $R^7$ represents straight-chain or branched $C_{1-6}$alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methyl-pentyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_{3-6}$-cycloalkyl, in particular cyclopropyl, cyclobutyl, cyclopentyl, cyclohexyl, aryl, in particular phenyl, or hetaryl, which are optionally substituted, $R^6$ and $R^7$ together with the atoms to which they are attached represent a 5-, 6- or 7-membered carbocyclic ring, which may optionally be substituted by $C_{14}$-alkyl, in particular methyl, B represents hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, halogeno-$C_{1-6}$-alkyl, in particular fluoromethyl, difluoromethyl, difluorochloromethyl, trifluoromethyl, trichloromethyl, 1-fluoroethyl, trifluoroethyl, 2-chloro-1,1,2-trifluoroethyl, hydroxy-$C_{1-6}$-alkyl, in particular hydroxymethyl, hydroxyethyl, $C_{1-4}$-alkanoyloxyalkyl, in particular acetoxymethyl, acetoxyethyl, 2-acetoxypropyl, $C_{1-2}$-alkoxyalkyl, amino-$C_{1-6}$-alkyl, in particular aminomethyl, aminoethyl, $C_{1-6}$-alkylamino-$C_{1-6}$-alkyl, in particular N-methylaminomethyl, $C_{1-6}$dialkylamino-$C_{1-6}$-alkyl, in particular N,N-dimethylaminomethyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_2 6$-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, $C_{3-6}$-cycloalkyl, in particular cyclopropyl, cyclobutyl, cyclopentyl, cyclohexyl, $C_3$-cycloalkyl-$C_{1-2}$-alkyl, in particular cyclopropylmethyl, carbamoyl-$C_{1-4}$-alkyl, in particular carbamoylmethyl, carboxyl-$C_{1-4}$-alkyl, in particular carboxylmethyl, formyl, $C_{1-4}$-alkoxy-dicarbonyl, in particular methoxydicarbonyl, aryl, in particular phenyl, aryl-$C_{1-2}$-alkyl, in particular benzyl, 1-phenylethyl, 2-phenylethyl, hetaryl, in particular pyridyl, pyrimidyl, pyrrolidyl, imidazolyl, thiazolyl, N-morpholinyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, ethyl, isopropyl, sec-butyl, tert-butyl, halogeno-$C_{1-4}$-alkyl, in particular trifluoromethyl, trichloromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl, or optionally represents a radical from a group consisting of $B^1$, $B^2$, $B^3$ and $B^4$

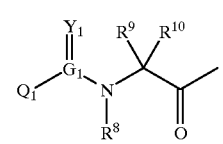

(B¹)

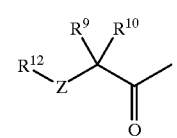

(B²)

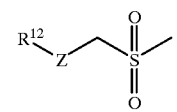

(B³)

-continued

(B⁴)

in which
R⁸ represents hydrogen, straight-chain or branched $C_{1-6}$-alkyl, in particular methyl, ethyl, propyl, isopropyl, isobutyl, sec-butyl, tert-butyl, $C_{3-6}$-cycloalkyl, in particular cyclopropyl, cyclobutyl, aryl-$C_{1-2}$-alkyl, in particular benzyl, heteroaryl-$C_{1-2}$-alkyl, in particular pyridylmethyl or thiazolylmethyl, which are optionally substituted,
R⁸ and R⁹ together with the atoms to which they are attached represent a 5- or 6-membered ring which may optionally be interrupted by oxygen, sulphur, sulphoxyl or sulphonyl and which may optionally be substituted by hydroxyl, $C_{1-4}$-alkoxy, aryl-$C_{1-2}$-alkoxy or amino,
R⁹ represents hydrogen, straight-chain or branched $C_{1-6}$-alkyl, in particular methyl, ethyl, propyl, isopropyl, sec-butyl, hydroxy-$C_{1-6}$-alkyl, in particular hydroxymethyl, 1-hydroxyethyl, $C_{1-4}$-alkanoyloxy-$C_{1-6}$-alkyl, in particular acetoxymethyl, 1-acetoxyethyl, aryl-$C_{1-4}$-alkoxy-$C_{1-4}$-alkyl, in particular benzyloxymethyl, 1-benzyloxyethyl, mercapto-$C_{1-4}$-alkyl, in particular mercaptomethyl, $C_{1-2}$-alkylthio-$C_{1-4}$-alkyl, in particular methylthiomethyl, $C_{1-2}$-alkylsulphonyl-$C_{1-4}$-alkyl, in particular methylsulphonylmethyl, carboxy-$C_{1-6}$-alkyl, in particular carboxymethyl, carboxyethyl, $C_{1-4}$-alkoxycarbonyl-$C_{1-4}$-alkyl, in particular methoxycarbonylmethyl, ethoxycarbonylmethyl, aryl-$C_{1-4}$-alkoxycarbonyl-$C_{1-4}$-alkyl, in particular benzyloxycarbonylmethyl, carbamoyl-$C_{1-6}$-alkyl, in particular carbamoylmethyl, carbamoylethyl, $C_{1-2}$-alkoxy-$C_{1-6}$-alkyl, in particular methoxymethyl, amino-$C_{1-6}$-alkyl, in particular aminopropyl, aminobutyl, $C_{1-6}$alkylamino-$C_{1-4}$-alkyl, in particular N-methylaminopropyl, N-methylaminobutyl, $C_{1-6}$-dialkylamino-$C_{1-6}$-alkyl, in particular N,N-dimethyl-aminopropyl, N,N-dimethylaminobutyl, guanidino-$C_{1-4}$-alkyl, in particular guanidopropyl, $C_{1-4}$-alkoxycarbonylamino-$C_{1-6}$-alkyl, in particular tert-butylcarbonylaminopropyl, tert-butyl-carbonylaminobutyl, $C_{2-6}$-alkenyl, in particular vinyl, 2-propenyl, 2-butenyl, 1-methyl-2-propenyl, $C_{3-6}$-cyclo-$C_{1-2}$-alkyl, in particular cyclopropylmethyl, cyclobutylmethyl, cyclohexylmethyl, hetaryl-$C_{1-2}$-alkyl, in particular pyridylmethyl, furylmethyl, thienylmethyl, indolylmethyl, N-methylindolylmethyl, imidazolylmethyl, N-methylimidazolylmethyl, aryl-$C_{1-2}$-alkyl, in particular benzyl, which may optionally be substituted by radicals from the group consisting of halogen, in particular fluorine, chlorine, bromine or iodine, $C_{1-4}$-alkyl, in particular methyl, ethyl, isopropyl, sec-butyl, tert-butyl, halogeno-$C_{1-4}$-alkyl, in particular trifluoromethyl, trichloromethyl, amino, hydroxyl, nitro, cyano, $C_{1-4}$-alkoxy, in particular methoxy, ethoxy or tert-butoxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-2}$-alkylenedioxy, in particular methylenedioxy or ethylenedioxy, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{3-6}$-cycloalkylainino, in particular pyrrolidino, piperidino, morpholino, thiomorpholino and dioxothiomorpholino, N-methylpiperazino, and
R⁸ represents hydrogen or methyl,

represents carboxyl, thiocarboxyl, —C=CH—NO₂, —C=CH—CN, —C=N—R¹¹, sulphoxyl, sulphonyl, —P(O)—O—R⁵ or —P(S)—O—R⁵,
R¹¹ represents hydrogen, hydroxyl, $C_{1-4}$-alkoxy, in particular methoxy, ethoxy, sec-butyloxy, $C_{1-4}$-alkylcarbonyl, in particular methylcarbonyl, ethylcarbonyl, halogeno-$C_{1-4}$-alkylcarbonyl, in particular trifluoromethylcarbonyl, trichloromethylcarbonyl, $C_{1-4}$-alkylsulphonyl, in particular methylsulphonyl, ethylsulphonyl, propylsulphonyl, nitro or cyano, and
Q¹ represents straight-chain or branched $C_{1-6}$-alkyl, in particular methyl, ethyl, propyl, isopropyl, sec-butyl, tert-butyl, halogeno-$C_{1-4}$-alkyl, in particular trifluoromethyl, trichloromethyl, chlorodifluoromethyl, dichlorofluoromethyl, 1-fluoroethyl, chloromethyl, bromomethyl, 2,2,2-trifluoroethyl, 2,2,2-trichloroethyl, $C_{2-6}$-alkenyl, in particular vinyl, 2-propenyl, 1-methyl-2-propenyl and 2-butenyl, $C_{3-6}$-cycloalkyl, in particular cyclopropyl, cyclobutyl, cyclopentyl and cyclohexyl, hetaryl-$C_{1-2}$-alkyl, in particular pyridylmethyl and thiazolylmethyl, aryl, in particular phenyl, hetaryl, in particular furyl, thienyl, pyrrolyl, thiazolyl, oxadiazolyl, oxazolyl, imidazolyl, pyridyl or pyrimidyl, which may optionally be substituted by radicals from the group consisting of halogen, in particular fluorine, chlorine, bromine or iodine, $C_{1-4}$-alkyl, in particular methyl, tert-butyl, halogeno-$C_{1-4}$-alkyl, in particular trifluoromethyl, difluoromethyl or trichloromethyl, amino, hydroxyl, nitro, $C_{1-4}$-alkoxy, in particular methoxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylamino, in particular N-methylamino, $C_{1-4}$-dialkylamino, in particular N,N-dimethylamino, or optionally represents a radical from the group consisting of G¹ and G²

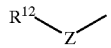
(G¹)

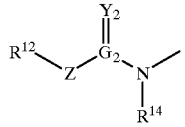
(G²)

in which

may represent carboxyl, thiocarboxyl or sulphonyl,

Z represents oxygen, sulphur or —$NR^{13}$, $R^{12}$ represents, if Z represents nitrogen, a cyclic amino group which is attached via a nitrogen atom, in particular 1-azetidinyl, pyrrolidino, 2-pyrrolin-2-yl, 1-pyrrolyl, piperidino, 1,4-dihydropyridin-1-yl, 1-imidazolidinyl, 1-homopiperazinyl, 1,2-dihydropyridazin-1-yl, 1,2-dihydropyrimidin-1-yl, perhydropyrimidin-1-yl, 1,4-diazacycloheptan-1-yl, thiazolidin-3-yl, isothiazolin-2-yl, morpholino, thiomorpholino, dioxothiomorpholino, which may optionally be substituted by radicals from the group consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkylamino-$C_{1-4}$-alkyl, in particular N-methylaminomethyl, N-methylaminoethyl, $C_{1-4}$dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, $R^{12}$ and $R^{13}$ independently of one another each represent hydrogen, straight-chain or branched $C_{1-6}$-alkyl, in particular methyl, ethyl, propyl, isopropyl, sec-butyl, iso-butyl, tert-butyl, $C_{2-6}$-alkenyl, in particular vinyl, 2-propenyl, 2-butenyl, 1-methyl-2-propenyl, $C_{2-6}$-alkinyl, in particular ethinyl, 2-propinyl, 2-butinyl, 3-butinyl, 2-methyl-2-propinyl, 2-pentinyl, 1-methyl-3-butinyl, 2-methyl-3-butinyl, 1,1-dimethyl-2-propinyl, $C_{3-6}$-cycloalkyl, in particular cyclopropyl, phenylcyclopropyl, cyclobutyl, cyclopentyl and cyclohexyl, $C_{3-6}$-cycloalkyl-$C_{1-2}$-alkyl, in particular cyclopropylmethyl, cyclobutylmethyl, cyclopentylmethyl and cyclohexylmethyl, $C_{1-4}$-alkoxy-$C_{1-2}$-alkyl, in particular methoxyethyl, hetaryl, in particular pyridyl and thiazolyl, hetaryl-$C_{1-2}$-alkyl, in particular pyridylmethyl and thiazolylmethyl and tetrahydrofurylmethyl, N-morpholinoethyl, which may optionally be substituted by radicals from the group consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkylamino-$C_{1-4}$-alkyl, in particular N-methylaminomethyl, N-methylaminoethyl, $C_{1-4}$-dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, or $R^{12}$ and $R^{13}$ together with the adjacent N atom represent a heterocyclic 5-, 6- or 7-membered ring system or represent a 7- to 10-membered bicyclic ring system, which may optionally also be interrupted by oxygen, sulphur, sulphoxyl, sulphonyl, carbonyl, —N—O, —N=, —$NR^{15}$— or by quaternized nitrogen and which is optionally substituted by $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkyl-amino-$C_{1-4}$-alkyl, in particular N-methylaminomethyl, N-methylaminoethyl, $C_{1-4}$-dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, $R^{14}$ represents hydrogen or $C_{1-4}$-alkyl, in particular methyl, ethyl, isopropyl, sec-butyl or tert-butyl, $R^{15}$ represents hydrogen, straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, $C_{2-6}$-alkenyl, in particular vinyl, 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 1,1-dimethyl-2-butenyl, 1,2-dimethyl-2-butenyl, 1-ethyl-2-propenyl, 2-hexenyl, $C_2$-6-alkinyl, in particular ethinyl, 2-propinyl, 2-butinyl, 3-butinyl, 1-methyl-2-propinyl, 2-pentinyl, 1-methyl-3-butinyl, 2-methyl-3-butinyl, 1,1-dimethyl-2-propinyl, $C_{3-6}$-cycloalkyl, in particular cyclopropyl, cyclobutyl, cyclopentyl, cyclohexyl, $C_{3-6}$-cycloalkyl-$C_{1-2}$-alkyl, in particular cyclopropylmethyl, $C_{1-4}$-alkoxycarbonyl, in particular methoxycarbonyl, ethoxycarbonyl, n-propoxycarbonyl, isopropoxycarbonyl, sec-butyloxycarbonyl and tert-butyloxycarbonyl, $C_{1-4}$-alkylcarbonyl, in particular methylcarbonyl, ethylcarbonyl, isopropylcarbonyl, sec-butylcarbonyl, tert-butylcarbonyl, $C_{3-6}$-cycloalkylcarbonyl, in particular cyclopropylcarbonyl, cyclobutylcarbonyl, cyclopentylcarbonyl, cyclohexylcarbonyl, cyano, aryl, in particular phenyl, aryl-$C_{1-2}$-alkyl, in particular benzyl, hetaryl, in particular pyridyl and thiazolyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, trichloromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylarnino, in particular N-methylamino, $C_{1-4}$-dialkylamino, in particular N,N-dimethylamino, $C_{1-4}$-alkylcarbonyl, in particular methylcarbonyl, C14-alkoxycarbonyl, in particular methoxycarbonyl, and also their optical isomers and racemates.

Particular preference is given to compounds of the general formula (I) and their salts

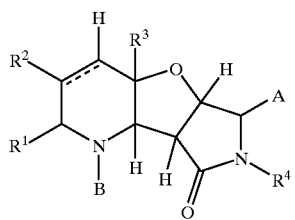

(I)

in which

R¹ represents hydrogen, straight-chain or branched $C_{1-4}$-alkyl, in particular methyl, ethyl, propyl, isopropyl, isobutyl, sec-butyl; C3-6-cycloalkyl, in particular cyclopropyl, R² represents hydrogen, straight-chain or branched $C_{1-4}$-alkyl, in particular methyl, ethyl, propyl, isopropyl, isobutyl, sec-butyl, tert-butyl, halogeno-$C_{1-4}$-alkyl, in particular bromomethyl, chloromethyl, hydroxy-$C_{1-4}$-alkyl, in particular hydroxymethyl, $C_{1-4}$-alkanoyloxy-$C_{1-4}$-alkyl, in particular acetoxymethyl, $C_{1-2}$-alkoxyalkyl, in particular methoxymethyl, $C_{1-2}$-alkylthioalkyl, in particular methylthiomethyl, $C_{1-2}$-alkylsulphinylalkyl, in particular methylsulphinylmethyl, $C_{1-2}$-alkyl-sulphonylalkyl, in particular methylsulphonylmethyl, amino-$C_{1-2}$-alkyl, in particular aminomethyl, $C_{1-6}$-alkylaminoalkyl, in particular N-methylaminomethyl, $C_{1-6}$-dialkylaminoalkyl, in particular N,N-dimethylaminomethyl, $C_{3-6}$cycloalkylaminoalkyl, in particular morpholinomethyl, thiomorpholinomethyl, $C_{3-6}$-cycloalkyl, in particular cyclopropyl, $C_{1-4}$-alkoxycarbonyl, in particular methoxycarbonyl, ethoxycarbonyl, R³ represents hydrogen, straight-chain or branched $C_{1-4}$-alkyl, in particular methyl, ethyl, propyl, isopropyl, isobutyl, sec-butyl, tert-butyl, R⁴ represents straight-chain or branched $C_{1-6}$-alkyl, in particular methyl, ethyl, propyl, isopropyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, halogeno-$C_{1-6}$-alkyl, in particular fluoromethyl, difluoromethyl, difluorochloromethyl, 1-fluoroethyl, $C_{1-4}$-alkoxycarbonyl-$C_{1-4}$-alkyl, in particular methoxycarbonylmethyl, $C_{2-6}$-alkenyl, in particular 2-propenyl, $C_{3-6}$-cycloalkyl, in particular cyclopropyl, cyclobutyl, cyclopentyl, cyclohexyl, $C_{3-6}$-cycloalkyl-$C_{1-2}$-alkyl, in particular cyclopropylmethyl, cyclobutylmethyl, aryl, in particular phenyl, aryl-$C_{1-2}$-alkyl, in particular benzyl, 1-phenylethyl, 2-phenylethyl, hetaryl, in particular pyridyl, thiazolyl, N-morpholinyl, hetaryl-$C_{1-2}$-alkyl, in particular 2-chlorpyrid-5-yl-methyl and chlorothiazol-5-yl-methyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, trichloromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl, A represents hydroxyl, $C_{1-6}$-alkyl, in particular methyl, ethyl, propyl, isopropyl, isobutyl, sec-butyl, tert-butyl, $C_{2-6}$-alkenyl, in particular vinyl, 2-propenyl, 2-butenyl, 3-butenyl, 1-methyl-2-propenyl, $C_{2-6}$-alkinyl, in particular ethinyl, 2-propinyl, 2-butinyl, 3-butinyl, $C_3$-cycloalkyl, in particular cyclopropyl, cyclobutyl, cyclopentyl, cyclohexyl, $C_3$-cycloalkyl-$C_{1-2}$-alkyl, in particular cyclopropylmethyl, $C_{1-6}$-alkoxy, in particular methoxy, ethoxy, propoxy, isopropoxy, isobutoxy, sec-butoxy, $C_{2-6}$-alkenyloxy, in particular 2-propenyloxy, 2-butenyloxy, 3-butenyloxy, $C_{2-6}$-alkinyloxy, in particular 2-propinyloxy, 2-butinyloxy, 3-butinyloxy, $C_{1-4}$-alkoxycarbonyl, in particular methoxycarbonyl, mercapto, $C_{1-4}$-alkylthio, in particular methylthio, ethylthio, propylthio, isopropylthio, cyano, carbamoyl, thiocarbamoyl, aryl-$C_{1-2}$-alkyloxy, in particular benzyloxy, hetaryl, in particular furyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, amino, hydroxyl, nitro, cyano, $C_{1-4}$-alkoxy, in particular methoxy, $C_{1-2}$-alkylenedioxy, in particular methylenedioxy, halogeno-$C_{1-4}$-alkoxy, in particular trifluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{14}$-alkylamino, in particular N-methylamino, $C_{1-4}$-dialkylamino, in particular N,N-dimethylamino, or optionally represents a radical from the group consisting of A¹, A² and A³

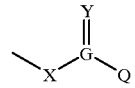

(A¹)

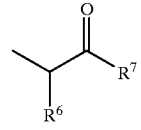

(A²)

(A³)

in which

X represents oxygen,

represents carboxyl or sulphonyl,

Q represents straight-chain or branched $C_{1-6}$-alkyl, in particular methyl, ethyl, propyl, isopropyl, isobutyl, sec-butyl, tert-butyl, $C_{2-6}$-alkenyl, in particular vinyl, 2-propenyl, 2-butenyl, 3-butenyl, 1-methyl- 2-propenyl, 2-methyl-2-propenyl, $C_{2-4}$-alkinyl, in particular 2-propinyl, 2-butinyl, 3-butinyl, $C_{3-6}$-cycloalkyl, in particular cyclopropyl, cyclobutyl, cyclopentyl, cyclohexyl, $C_{3-6}$-cycloalkoxy, in particular cyclopropyloxy, $C_{1-6}$-alkoxy, in particular methoxy, ethoxy, propoxy, isopropoxy, isobutoxy, sec-butoxy, tert-butoxy, $C_{2-4}$-alkenyloxy, in particular vinyloxy, 2-propenyloxy, 2-butenyloxy, 3-butenyloxy, 1-methyl-2-propenyloxy, 2-methyl-2-propenyloxy, $C_{2-6}$-alkinyloxy, in particular 2-propinyloxy, 2-butinyloxy, $C_{1-4}$-alkylamino, in particular N-methylamino, N-ethylamino, $C_{1-4}$-dialkylamino, in particular N,N-dimethylamino, N,N-diethylamino, a cyclic amino group which is attached via nitrogen, in particular morpholino, thiomorpholino, piperazino, piperidino, pyrrolidino, aryl, in particular phenyl, aryl-$C_{1-2}$-alkyl, in particular benzyl, aryl-$C_{1-2}$-alkyloxy, in particular benzyloxy, which may optionally be substituted, $R^6$ represents hydrogen or methyl, $R^7$ represents straight-chain or branched $C_{1-6}$alkyl, in particular methyl, ethyl, propyl, isopropyl, isobutyl, sec-butyl, tert-butyl, $C_{2-6}$-alkenyl, in particular vinyl, 2-propenyl, 2-butenyl, 3-butenyl, $C_{3-6}$-cycloalkyl, in particular cyclopropyl, cyclobutyl, cyclopentyl, aryl, in particular phenyl, or hetaryl, which are optionally substituted, $R^6$ and $R^7$ together with the atoms to which they are attached represent a 5-, 6- or 7-membered carbocyclic ring which may optionally be substituted by $C_{1-4}$-alkyl, in particular methyl, B represents hydrogen, straight-chain or branched $C_{1-6}$-alkyl, in particular methyl, ethyl, propyl, isopropyl, isobutyl, sec-butyl, $C_{1-4}$-alkanoyloxyalkyl, in particular acetoxymethyl, acetoxyethyl, 2-acetoxypropyl, $C_{1-2}$-alkoxyalkyl, in particular methoxymethyl, amino-$C_{1-6}$-alkyl, in particular aminomethyl, aminoethyl, $C_{1-6}$-alkylamino-$C_{1-6}$-alkyl, in particular N-methylaminomethyl, $C_{1-6}$-dialkylamino-$C_{1-6}$-alkyl, in particular N,N-dimethylaminomethyl, $C_{2-6}$-alkenyl, in particular vinyl, 2-propenyl, 2-butenyl, $C_{2-6}$-alkinyl, in particular 2-propinyl, carbamoyl-$C_{1-4}$-alkyl, in particular carbamoylmethyl, carboxy-$C_{1-4}$-alkyl, in particular carboxylmethyl, $C_{1-4}$-alkoxydicarbonyl, in particular methoxydicarbonyl, aryl, in particular phenyl, aryl-$C_{1-2}$-alkyl, in particular benzyl, 1-phenylethyl, 2-phenylethyl, hetaryl, in particular pyridyl, pyrimidyl, pyrrolidyl, imidazolyl, thiazolyl, N-morpholinyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, amino, hydroxyl, nitro, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, difluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl, or optionally represents a radical from the group consisting of $B^1$, $B^2$, $B^3$ and $B^4$

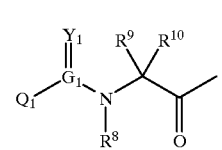 (B$^1$)

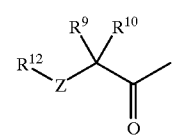 (B$^2$)

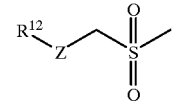 (B$^3$)

 (B$^4$)

in which $R^8$ represents hydrogen, straight-chain or branched $C_{1-6}$-alkyl, in particular methyl, ethyl, $C_{3-6}$-cycloalkyl, in particular cyclopropyl, $R^8$ and $R^9$ together with the atoms to which they are attached represent a 5- or 6-membered ring, which may optionally be interrupted by sulphur and is optionally substituted by hydroxyl, tert-butoxy, benzyloxy, $R^9$ represents hydrogen, straight-chain or branched $C_{1-6}$-alkyl, in particular methyl, ethyl, propyl, isopropyl, sec-butyl, $R^{10}$ represents hydrogen or methyl,

represents carboxyl, —C=CH—NO$_2$, —C=CH—CN, —C=N—R$^{11}$, sulphonyl, $R^{11}$ represents halogeno-$C_{1-4}$alkylcarbonyl, in particular trifluoromethylcarbonyl, trichloromethylcarbonyl, $C_{1-4}$-alkylsulphonyl, in particular methylsulphonyl, ethylsulphonyl, nitro or cyano, and $Q^1$ represents a radical from the group consisting of $G^1$ and $G^2$

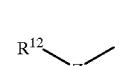 (G$^1$)

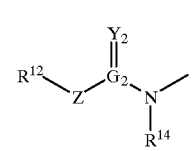 (G$^2$)

in which

may represent carboxyl or sulphonyl,

Z represents oxygen or $R^{12}$ represents, if Z is nitrogen, a cyclic amino group which is attached via a nitrogen atom, in particular pyrrolidino, 2-pyrrolin-2-yl, 1-pyrrolyl, piperidino, 1,4-dihydropyridin-1-yl, 1-homopiperazinyl, morpholino, thiomorpholino, dioxothiomorpholino, which may optionally be substituted by radicals from the group consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkylamino-$C_{1-4}$-alkyl, in particular N-methylaminomethyl, N-methylaminoethyl, $C_{1-4}$-dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, $R^{12}$ and $R^{13}$ independently of one another each represent hydrogen, straight-chain or branched $C_{1-6}$alkyl, in particular methyl, ethyl, propyl, isopropyl, sec-butyl, $C_{2-4}$-alkenyl, in particular vinyl, 2-propenyl, 2-butenyl, 1-methyl-2-propenyl, $C_{2-4}$-alkinyl, in particular ethinyl, 2-propinyl, 2-butinyl, $C_{3-6}$-cycloalkyl, in particular cyclopropyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkylamino-$C_{1-4}$-alkyl, in particular N-methylaminomethyl, N-methylaminoethyl, $C_{1-4}$-dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{,4}$-alkylcarbonyl, in particular methylcarbonyl, $C_{1-4}$-alkoxycarbonyl, in particular methoxycarbonyl, or $R^{12}$ and $R^{13}$ together with the adjacent N atom represent a heterocyclic 5-, 6- or 7-membered ring system or represent a 7- to 10-membered bicyclic ring system, which may optionally also be interrupted by oxygen, sulphur, sulphoxyl, sulphonyl, carbonyl, —N—O, —N=, —$NR^{15}$- or by quarternized nitrogen and which is optionally substituted by $C_{1-4}$-alkyl, in particular methyl, hydroxy-$C_{1-4}$-alkyl, in particular hydroxymethyl, amino-$C_{1-4}$-alkyl, in particular aminomethyl, aminoethyl, $C_{1-4}$-alkylamino-$C_{1-4}$-alkyl, in particular N-methylaminomethyl, N-methylaminoethyl, $C_{1-4}$-dialkylamino-$C_{1-4}$-alkyl, in particular N,N-dimethylaminomethyl, N,N-dimethylaminoethyl, amino, hydroxyl, $C_{1-4}$-alkoxy, in particular methoxy, $C_{1-4}$-alkylcarbonyl, in particular methylcarbonyl, $C_{1-4}$-alkoxycarbonyl, in particular methoxycarbonyl, halogen, in particular fluorine, chlorine, bromine or iodine, $R^{14}$ represents hydrogen or $C_{1-4}$-alkyl, in particular methyl, ethyl, $R^{15}$ represents hydrogen, straight-chain or branched $C_{1-6}$-alkyl, in particular methyl, ethyl, $C_{2-6}$-alkenyl, in particular vinyl, 2-propenyl, $C_{2-6}$-alkinyl, in particular 2-propinyl, $C_{3-6}$-cycloalkyl, in particular cyclopropyl, $C_{1-4}$-alkoxycarbonyl, in particular methoxycarbonyl, ethoxycarbonyl, $C_{1-4}$-alkylcarbonyl, methylcarbonyl, $C_{3-6}$-cycloalkylcarbonyl, in particular cyclopropylcarbonyl, cyano, aryl, in particular phenyl, aryl-$C_{1-2}$-alkyl, in particular benzyl, hetaryl, in particular pyridyl and thiazolyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, trichloromethyl, amino, hydroxyl, cyano, $C_{1-4}$-alkoxy, in particular methoxy, $C_{1-2}$-alkylenedioxy, in particular methylenedioxy or ethylenedioxy, halogeno-$C_{1-4}$-alkoxy, in particular trifluoromethoxy, $C_{1-4}$-alkylthio, in particular methylthio, halogeno-$C_{1-4}$-alkylthio, in particular trifluoromethylthio, $C_{1-4}$-alkylsulphonyl, in particular methylsulphonyl, $C_{1-4}$-alkylamino, in particular N-methylamino, $C_{1-4}$-dialkylamino, in particular N,N-dimethylamino, $C_{1-4}$-alkylcarbonyl, in particular methylcarbonyl, $C_{1-4}$-alkoxycarbonyl, in particular methoxycarbonyl, and also their optical isomers and racemates.

Very particular preference is given to compounds of the general formula (I) and their salts

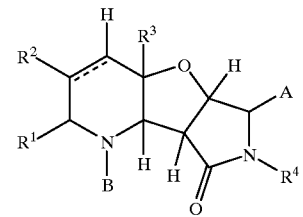

(I)

in which $R^1$ represents hydrogen, $R^2$ represents straight-chain or branched $C_{1-4}$-alkyl, in particular methyl or ethyl, $R^3$ represents straight-chain or branched $C_{1-4}$-alkyl, in particular methyl or ethyl, $R^4$ represents straight-chain or branched $C_{1-6}$-alkyl, in particular methyl, ethyl, propyl, isopropyl, isobutyl, sec-butyl, n-butyl, tert-butyl, $C_{2-6}$-alkenyl, in particular 2-propenyl, $C_{3-6}$-cycloalkyl, in particular cyclopropyl, cyclobutyl, cyclopentyl, cyclohexyl, $C_{3-6}$-cycloalkyl-$C_{1-2}$-alkyl, in particular cyclopropylmethyl, aryl, in particular phenyl, aryl-$C_{1-2}$-alkyl, in particular benzyl, 1-phenylethyl, 2-phenylethyl, hetaryl-$C_{1-2}$-alkyl, in particular 2-chloropyrid-5-yl-methyl and chlorothiazol-5-yl-methyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, in particular trifluoromethyl, trichloromethyl, amino, hydroxyl, nitro, cyano, $C_{1-4}$-alkoxy, in particular methoxy, halogeno-$C_{1-4}$-alkoxy, in particular trifluoromethoxy, difluoromethoxy, $C_{1-4}$-alkylamino, in particular N-methylamino, $C_{1-4}$dialkylamino, in particular N,N-dimethylamino, A represents hydroxyl, $C_{1-6}$-alkyl, in particular propyl, sec-butyl, $C_{2-6}$-alkenyl, in particular vinyl, 2-propenyl, 2-butenyl, 3-butenyl, $C_{2-6}$-alkinyl, in particular 2-propinyl, 2-butinyl, 3-butinyl, $C_36$-cycloalkyl, in particular cyclopropyl, $C_{3-6}$-cycloalkyl-$C_{1-2}$-alkyl, in particular cyclopropylmethyl, $C_{1-6}$-alkoxy, in particular methoxy, ethoxy, propoxy, isopropoxy, sec-butoxy, $C_{2-6}$-alkenyloxy, in particular 2-propenyloxy, $C_{2-6}$-alkinyloxy, in particular 2-propinyloxy, $C_{1-4}$-alkoxycarbonyl, in particular methoxycarbonyl, cyano, aryl-$C_{1-2}$-alkyloxy, in particular benzyloxy, hetaryl, in particular furyl, which may optionally be substituted by radicals from the group consisting of halogen, in particular fluorine, chlorine, bromine or iodine, $C_{1-4}$-alkyl, in particular methyl, amino, hydroxyl, nitro, cyano, $C_{1-4}$-alkoxy, in particular methoxy, halogeno-$C_{1-4}$-alkoxy, in particular trifluoromethoxy, $C_{1-4}$-alkylamino, in particular N-methylamino, $C_{1-4}$-dialkylamino, in particular N,N-dimethylamino, or optionally represents a radical from the group consisting of $A^1$, $A^2$ and $A^3$

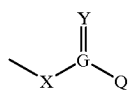 (A¹)

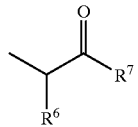 (A²)

 (A³)

in which

X represents oxygen,

represents carboxyl or sulphonyl,

Q represents straight-chain or branched $C_{1-6}$-alkyl, in particular methyl, ethyl, propyl, isopropyl, isobutyl, sec-butyl, $C_{2-6}$-alkenyl, in particular vinyl, 2-propenyl, $C_{3-6}$-cycloalkyl, in particular cyclopropyl, $C_{3-6}$-cycloalkoxy, in particular cyclopropyloxy, $C_{1-6}$-alkoxy, in particular methoxy, ethoxy, propoxy, isopropoxy, isobutoxy, sec-butoxy, $C_{2-6}$-alkenyloxy, in particular 2-propenyloxy, $C_{1-4}$-alkylamino, in particular N-methylamino, N-ethylamino, $C_{1-4}$-dialkylamino, in particular N,N-dimethylamino, N,N-diethylamino, a cyclic amino group which is attached via nitrogen, in particular morpholino, piperazino, piperidino, pyrrolidino, aryl, in particular phenyl, aryl-$C_{1-2}$-alkyl, in particular benzyl, aryl-$C_{1-2}$-alkyloxy, in particular benzyloxy, which are optionally substituted, $R^6$ represents hydrogen, $R^7$ represents straight-chain or branched $C_{1-6}$-alkyl, in particular methyl, ethyl, propyl, isopropyl, sec-butyl, $C_{2-6}$-alkenyl, in particular vinyl, 2-propenyl, 2-butenyl, $C_{3-6}$-cycloalkyl, in particular cyclopropyl, aryl, in particular phenyl, or hetaryl, which are optionally substituted, $R^6$ and $R^7$ together with the atoms to which they are attached represent a 5-, 6- or 7-membered carbocyclic ring, which may optionally be substituted by $C_{1-4}$-alkyl, in particular methyl, B represents hydrogen, straight-chain or branched $C_{1-6}$-alkyl, in particular methyl, ethyl, $C_{2-4}$-alkenyl, in particular 2-propenyl, 2-butenyl, carbamoyl-$C_{1-4}$-alkyl, in particular carbamoylmethyl, carboxyl-$C_{1-4}$-alkyl, in particular carboxylmethyl, aryl, in particular phenyl, aryl-$C_{1-2}$-alkyl, in particular benzyl, hetaryl, in particular pyridyl, pyrimidyl, pyrrolidyl, imidazolyl, thiazolyl, N-morpholinyl, hetaryl-$C_{1-2}$-alkyl, in particular pyridylmethyl and thiazolylmethyl, which may optionally be substituted by radicals from the group consisting of halogen, in particular fluorine, chlorine, bromine or iodine, $C_{1-4}$-alkyl, in particular methyl, halogeno-$C_{1-4}$-alkyl, inparticular trifluoromethyl, amino, hydroxyl, nitro, cyano, $C_{1-4}$-alkoxy, in particular methoxy, halogeno-$C_{1-4}$-alkoxy, in particular trifluoromethoxy, difluoromethoxy, $C_{1-4}$-alkylamino, in particular N-methylamino, $C_{1-4}$-dialkylamino, in particular N,N-dimethylamino, or optionally represents a radical from the group consisting of $B^1$, $B^2$, $B^3$ and $B^4$

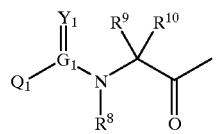 (B¹)

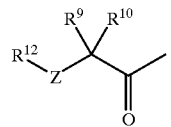 (B²)

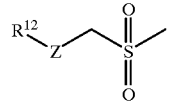 (B³)

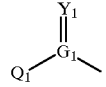 (B⁴)

in which $R^8$ represents hydrogen or methyl, $R^8$ and $R^9$ together with the atoms to which they are attached represent a 5- or 6membered ring, which may optionally be interrupted by sulphur and which is optionally substituted by hydroxyl, tert-butoxy, benzyloxy, $R^9$ represents hydrogen, straight-chain or branched $C_{1-6}$-alkyl, in particular methyl, ethyl, propyl, isopropyl, sec-butyl, $R^{10}$ represents hydrogen,

(G¹)

represents carboxyl or sulphonyl,
Q¹ represents a radical from the group consisting of G¹ and G²

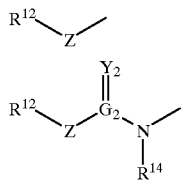
(G²)

in which

may represent carboxyl or sulphonyl,
Z represents oxygen or —$NR^{13}$,
$R^{12}$ represents, in the case that Z represents nitrogen, a cyclic amino group which is attached via a nitrogen atom, in particular pyrrolidino, 1-pyrrolyl, piperidino, morpholino, thiomorpholino or dioxothiomorpholino,
$R^{12}$ and $R^{13}$ independently of one another each represent hydrogen, straight-chain or branched $C_{1-6}$-alkyl, in particular methyl, ethyl, propyl, isopropyl, sec-butyl, $C_{2-4}$-alkenyl, in particular vinyl, 2-propenyl, 1-methyl-2-propenyl, $C_{2-4}$-alkinyl, in particular ethinyl, 2-propinyl, $C_{3-6}$-cycloalkyl, in particular cyclopropyl, hetaryl-$C_{1-2}$-alkyl, in particular 5-chloro-pyridylmethyl and chlorothiazol-5-yl-methyl, or
$R^{12}$ and $R^{13}$ together with the adjacent N atom represent a heterocyclic 5-, 6- or 7-membered ring system or represent a 7- to 10-membered bicyclic ring system, which may optionally also be interrupted by oxygen, sulphur, sulphoxyl, sulphonyl, carbonyl, —N—O, —N=, —$NR^{15}$— or by quaternized nitrogen and which is optionally substituted by $C_{1-4}$-alkyl, in particular methyl, hydroxy-$C_{1-4}$-alkyl, in particular hydroxymethyl, $C_{1-4}$-dialkylamino-$C_{1-4}$-alkyl, in particular N,N-dimethylaminomethyl, N,N-dimethylaminoethyl, $C_{1-4}$-alkoxycarbonyl, in particular methoxycarbonyl,
$R^{14}$ represents $C^{1-4}$-alkyl, in particular methyl,
$R^{15}$ represents straight-chain or branched $C_{1-6}$-alkyl, in particular methyl, $C_{2-6}$-alkenyl, in particular vinyl, 2-propenyl, $C_{2-6}$-alkinyl, in particular 2-propinyl, $C_{3-6}$-cycloalkyl, in particular cyclopropyl, $C_{1-4}$-alkoxycarbonyl, in particular methoxycarbonyl, $C_{1-4}$-alkylcarbonyl, in particular methylcarbonyl, $C_{3-6}$-cycloalkylcarbonyl, in particular cyclopropylcarbonyl,
and also their optical isomers and racemates.

The compounds of the general formula (I) according to the invention and their salts furthermore contain one or more chiral centres, and they can therefore be present as pure stereoisomers or in the form of various enantiomer and diastereo isomer mixtures, which can, if required, be separated in a manner known per se. The invention therefore relates both to the pure enantiomers and diastereomers, and to mixtures thereof. They are employed for controlling endoparasites, in particular in the field of medicine and veterinary medicine.

The present invention also relates to compounds of the general formula (I) in the form of an acid addition salt. Acids which can be used for salt formation are inorganic acids, such as hydrochloric acid, hydrobromic acid, nitric acid, sulphuric acid, phosphoric acid, or organic acids, such as formic acid, acetic acid, propionic acid, malonic acid, oxalic acid, fumaric acid, adipic acid, stearic acid, tartaric acid, oleic acid, methanesulphonic acid, benzenesulphonic acid or toluenesulphonic acid.

Suitable salts of the compounds of the general formula (1) which may be mentioned are customary nontoxic salts, i.e. salts with different bases and salts with added acids. Preference is given to salts with inorganic bases, such as alkali metal salts, for example sodium salts, potassium salts or cesium salts, alkaline earth metal salts, for example calcium salts or magnesium salts, ammonium salts, salts with organic bases and also with organic amines, for example triethylammonium salts, pyridinium salts, picolinium salts, ethanolammonium salts, triethanolammonium salts, dicyclohexylammonium salts or N,N-dibenzylethylenediammonium salts, salts with inorganic acids, for example hydrochlorides, hydrobromides, dihydrosulphates or trihydrophosphates, salts with organic carboxylic acids or organic sulphonic acids, for example formates, acetates, trifluoroacetates, maleates, tartrates, methanesulphonates, benzenesulphonates or para-toluenesulphonates, salts with basic amino acids or acidic amino acids, for example arginates, aspartates or glutamates.

Examples of the novel compounds according to the invention are listed in Tables 1 to 26.

TABLE 1

(I)

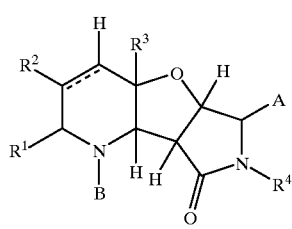

Compounds of Table 1 correspond to the general formula (I-1) in which R¹ = —H; R², R³, R⁴ = -methyl; A = —OH; B = as listed below:

| Comp. No. | B | Comp. No. | B |
|---|---|---|---|
| 1 | —SO₂-Me | 22 | —CO—NH-iPr |
| 2 | —SO₂-iPr | 23 | —CO—NH—CH₂—CH=CH₂ |
| 3 | —CO-Me | 24 | —CO—CH₂—NMe-Z |
| 4 | —CO—CH₂—Cl | 25 | —CO—CH₂—NMe-Boc |
| 5 | —CO—CF₃ | 26 | —CO—CHMe-NH-Me |
| 6 | —CO—CCl₃ | 27 | —CO—CHMe-NMe₂ |
| 7 | —CO-cyclopropyl | 28 | —CO—CHMe-NMe-Z |
| 8 | —CO—O-Me | 29 | —CO—CHMe-NMe-Boc |
| 9 | —CO—NMe-CO—NMe₂ | 30 | —CO—CHEt-NH-Me |
| 10 | —CO—NMe-CO—NEt₂ | 31 | —CO—CHEt-NMe₂ |
| 11 | —CO—O—(CH₂)₂—CF=CF₂ | 32 | —CO—CHEt-NMe-Z |
| 12 | pyrazin-2-yl- | 33 | —CO—CHEt-NMe-Boc |
| 13 | —CS—NH-Me | 34 | —CO—CHiBu-NH-Me |
| 14 | —CS—NH-ipr | 35 | —CO—CHiBu-NMe₂ |
| 15 | —CS—NH-nBu | 36 | —CO—CHiBu-NMe-Z |
| 16 | —CS—NH-sBu | 37 | —CO—CHiBu-NMe-Boc |
| 17 | —CS—NH-Cyclopropyl | 38 | —CO—CHiPr—NMe-Boc |
| 18 | —CS—NH—CH₂—CH=CH₂ | 39 | —CO—CHiPr—NMe-Z |
| 19 | —CS—NMe₂ | 40 | —CO—O—CHMe-CH=CH₂ |
| 20 | —CO—NMe₂ | 41 | —CO—CH₂—CF=CF₂ |
| 21 | —CO—NH-Me | 42 | —CO—CH₂—CH=CH₂ |

49 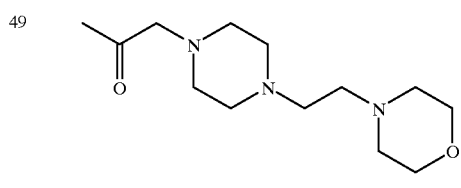
61 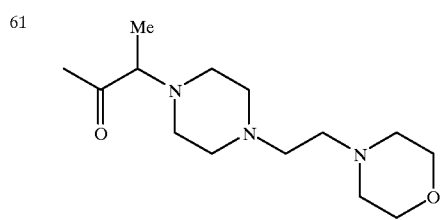
50 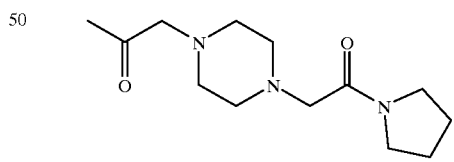
62 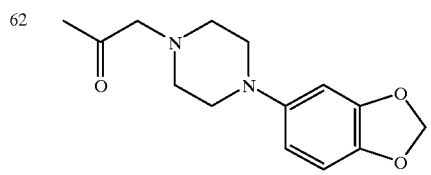
51 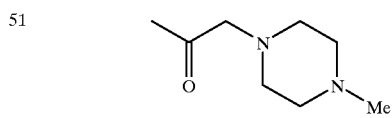
63 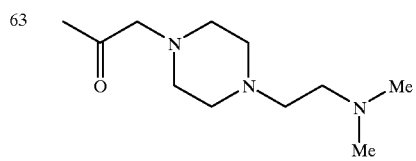
52 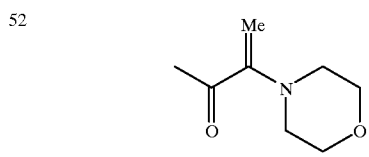
64 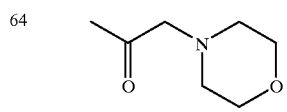
53 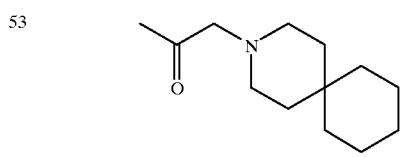
65 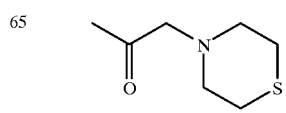
54 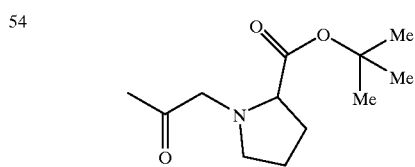
66 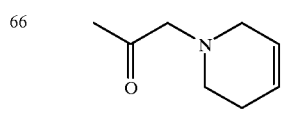
67 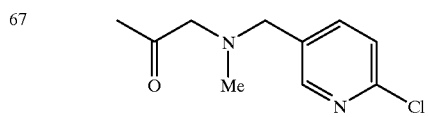
79 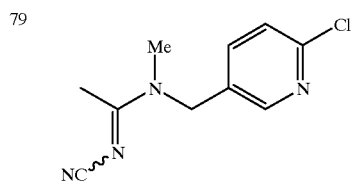
68 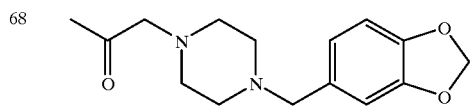
80 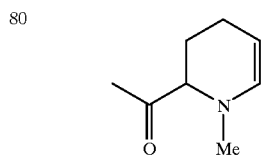
69 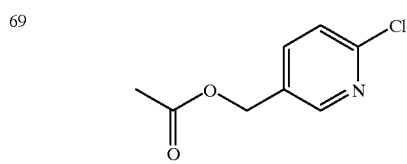
81 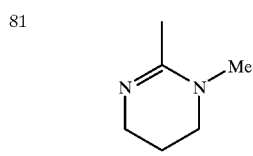

| 70 | 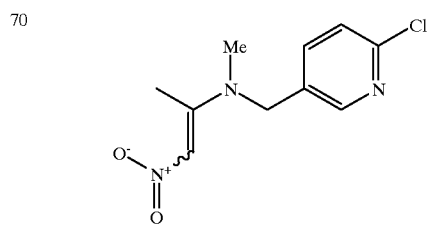 | 82 | 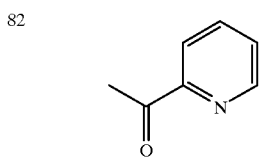 |
| 71 |  | 83 | 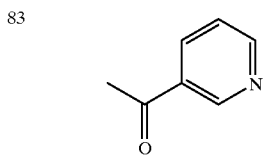 |
| 72 | 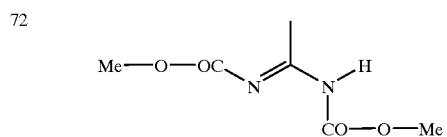 | 84 | 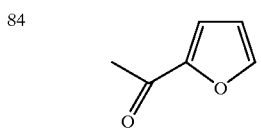 |
| 73 | 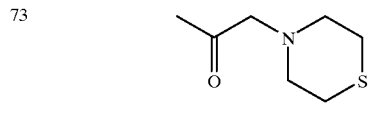 | 85 | 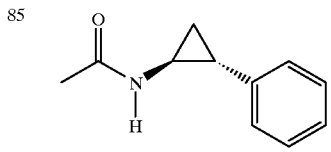 |
| 74 | 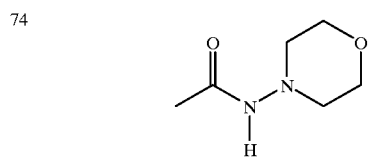 | 86 | 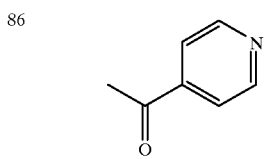 |
| 75 | 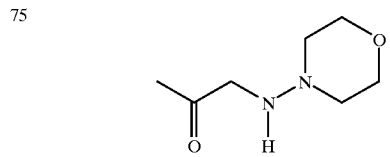 | 87 | 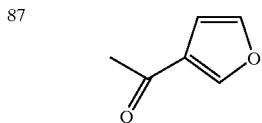 |
| 76 | 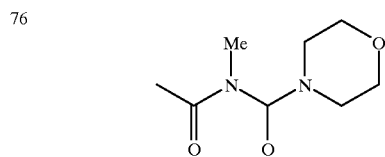 | 88 | 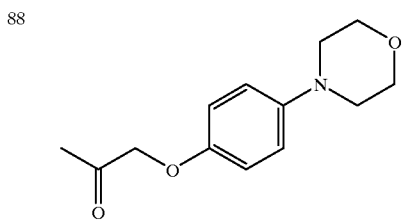 |
| 77 | 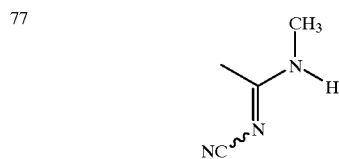 | 89 | 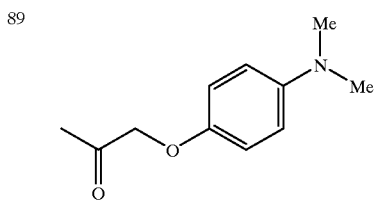 |

Abbreviations: Ac: -acetyl; Bu: -butyl; Me: -methyl; Ph: -phenyl; Pr: -propyl; Et: ethyl; i-, s- and t-: iso-, secondary and tertiary Boc=tert-butoxycarbonyl Z=benzyloxycarbonyl

Table 2

Table 2 contains the compounds of the general formula (I-1), in which $R^1$=—H; $R^2$, $R^3$=-methyl; $R^4$=-ethyl; A=—OH; B has the meanings listed in Table 1.

Table 3

Table 3 contains the compounds of the general formula (I-1), in which $R^1$=—H; $R^2$, $R^3$=-methyl; $R^4$=-n-propyl; A=—OH; B has the meanings listed in Table 1.

Table 4

Table 4 contains the compounds of the general formula (I-1), in which $R^1$=—H; $R^2$, $R^3$=-methyl; $R^4$=-isopropyl; A=—OH; B has the meanings listed in Table 1.

Table 5

Table 5 contains the compounds of the general formula (I-1), in which $R^1$=—H; $R^2$, $R^3$=-methyl; $R^4$=-cyclopropyl; A=—OH; B has the meanings listed in Table 1.

Table 6

Table 6 contains the compounds of the general formula (I-1), in which $R^1$=—H; $R^2$, $R^3$=-methyl; $R^4$=-n-butyl; A=—OH; B has the meanings listed in Table 1.

Table 7

Table 7 contains the compounds of the general formula (I-I), in which $R^1$=—H; $R^2$, $R^3$=-methyl; $R^4$=-sec-butyl; A=—OH; B has the meanings listed in Table 1.

Table 8

Table 8 contains the compounds of the general formula (I-1), in which $R^1$=—H; $R^2$, $R^3$=-methyl; $R^4$=2-phenylethyl; A=—OH; B has the meanings listed in Table 1.

Table 9

Table 9 contains the compounds of the general formula (I-1), in which $R^1$=—H; $R^2$, $R^3$, $R^4$=-methyl; A=—O—Me; B has the meanings listed in Table 1.

Table 10

Table 10 contains the compounds of the general formula (I-1), in which $R^1$=—H; $R^2$, $R^3$=-methyl; $R^4$=-ethyl; A=—O—Me; B has the meanings listed in Table 1.

Table 11

Table 11 contains the compounds of the general formula (I-1), in which $R^1$=—H; $R^2$, $R^3$, $R^4$=-methyl; A=—O-isopropyl; B has the meanings listed in Table 1.

Table 12

Table 12 contains the compounds of the general formula (I-1), in which $R^1$=—H; $R^2$, $R^3$=-methyl; $R^4$=-ethyl; A=—O-isopropyl; B has the meanings listed in Table 1.

Table 13

Table 13 contains the compounds of the general formula (I-1), in which $R^1$=—H; $R^2$, $R^3$, $R^4$=-methyl; A=—O-acetyl; B has the meanings listed in Table 1.

Table 14

Table 14 contains the compounds of the general formula (I-1), in which $R^1$=—H; $R^2$, $R^3$=-methyl; $R^4$=-ethyl; A=—O-acetyl; B has the meanings listed in Table 1.

Table 15

Table 15 contains the compounds of the general formula (I-1), in which $R^1$=—H; $R^2$, $R^3$=-methyl; $R^4$=-cyclopropyl; A=—O-acetyl; B has the meanings listed in Table 1.

Table 16

Table 16 contains the compounds of the general formula (I-1), in which $R^1$=—H; $R^2$, $R^3$, $R^4$=-methyl; A=—CN; B has the meanings listed in Table 1.

Table 17

Table 17 contains the compounds of the general formula (I-1), in which $R^1$=—H; $R^2$, $R^3$=-methyl $R^4$=-ethyl; A=—CN; B has the meanings listed in Table 1.

Table 18

Table 18 contains the compounds of the general formula (I-1), in which $R^1$=-H; $R^2$, $R^3$, $R^4$=-methyl; A=—$CH_2$—CH=$CH_2$; B has the meanings listed in Table 1.

Table 19

Table 19 contains the compounds of the general formula (I-1), in which $R^1$=—H; $R^2$, $R^3$=-methyl $R^4$=-ethyl; A=—$CH_2$—CH=$CH_2$; B has the meanings listed in Table 1.

Table 20

Table 20 contains the compounds of the general formula (I-1), in which $R^1$=—H; $R^2$, $R^3$, $R^4$=-methyl; A=fur-2-yl; B has the meanings listed in Table 1.

Table 21

Table 21 contains the compounds of the general formula (I-1), in which $R^1$=—H; $R^2$, $R^3$=-methyl $R^4$=-ethyl; A=fur-2-yl; B has the meanings listed in Table 1.

TABLE 22

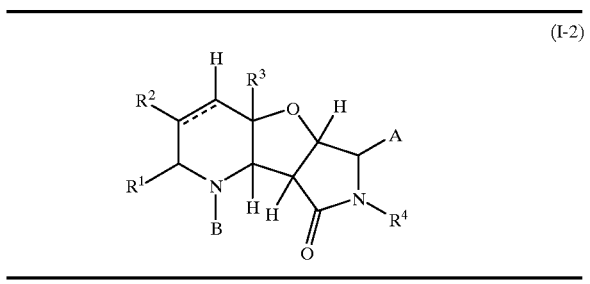

(I-2)

Table 22 contains compounds of the general formula (1-2), in which $R^1$=—H; $R^2$, $R^3$,$R^4$=-methyl; A=—OH; B has the meanings listed in Table 1.

Table 23

Table 23 contains compounds of the general formula (I-2), in which $R^1$=—H; $R^2$, $R^3$=-methyl, $R^4$=-ethyl; A=—OH; B has the meanings listed in Table 1.

Table 24

Table 24 contains compounds of the general formula (1-2), in which $R^1$=—H; $R^2$, $R^3$=-methyl, $R^4$=-cyclopropyl; A=—OH; B has the meanings listed in Table 1.

Table 25

Table 25 contains compounds of the general formula (I-2), in which $R^1$=—H; $R^2$, $R^3$, $R^4$=-methyl; A=—O-acetyl; B has the meanings listed in Table 1.

Table 26

Table 26 contains compounds of the general formula (1-2), in which $R^1$=—H; $R^2$, $R^3$=-methyl, $R^4$=-ethyl; A=—O-acetyl; B has the meanings listed in Table 1.

The compounds of the general formula (I) are novel; they can be prepared, for example, using the processes mentioned above under 3, 5 and 7.

Surprisingly and according to the invention, the novel 6-hydroxy-1,2,4a,5a,8a,8b-hexahydro-6H-pyrrolo[3',4':4,5] furo[3,2-b]pyrid-8(7H)-one and 6-hydroxy-1,2,3,4,4a,5a,8a, 8-octahydro-6H-pyrrolo[3',4':4,5]furo[3,2-b)pyrid-8(7H)-one derivatives of the general formulae (Ia–d) can be formed according to process 2 via regioselective hydrogenation of an imidcarbonyl function in the pyrrolidine moiety from corresponding 1,2,4a,5a,8a,8b-hexahydro- or 1,2,3,4,4a,5a, 8a,8b-octahydro-6H-pyrrolo[3',4':4,5]furo[3,2-b]pyridine-6, 8(7H)-dione derivatives of the general formulae (IIa–d) and be utilised for the subsequent reactions according to processes 2, 3 and 4.

According to expectation, the compounds of the general formulae (Ia–d) can, depending on the substituents, be present in the form of an isomer mixture comprising a 6α-hydroxy isomer and a 6β-hydroxy isomer.

Hereinbelow, the processes 2, 3 and 4 according to the invention are illustrated by selected examples (cf. also Preparation Examples).

Using, for example, 7-(p-tolyl)-4aα, 5aα,8aα,8bα-(+)-tetrahydro-3,4a-dimethyl-6H-pyrrolo[3',4':4,5]furo[3,2-b] pyridine-6,8 (7H)-dione as compound of the general formula (III) for hydrogenation in process 2, the two 6α-hydroxy- and 6β-hydroxy-7-(p-tolyl)-1,2,4aα,5aα,8aα,8bα-(±)-hexahydro-3,4a-dimethyl-6H-pyrrolo[3',4':4,5]furo[3,2-b] pyrid-8(7H)-ones are formed as an isomer mixture (cf. Scheme I).

Scheme I

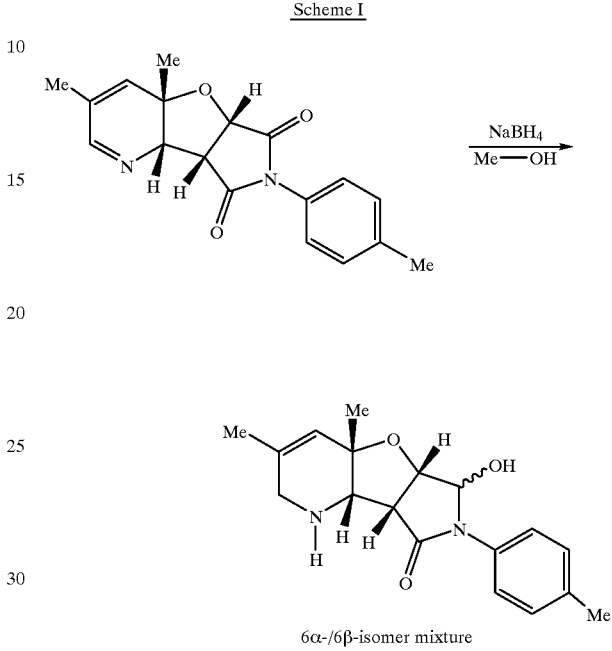

6α-/6β-isomer mixture

Examples for the radio and stereoselective preparation of the 6β-isomers according to the invention which may be mentioned are the hydrogenations of 1-allyloxycarbonyl-7-ethyl- 1,2,4aα,5aα,8aα,8bα-(±)hexahydro-3,4a-dimethyl- and 1-allyloxycarbonyl-1,2,3,4,4aα,5aα,8aα,8bα(+)-octahydro-3β,4a,7-trimethyl-6H-pyrrolo[3',4':4,5]furo[3,2-b]pyridine-6,8(7H)-diones as compounds of the general formulae (IIa) and (IIb) which, according to the abovementioned process, give, in a regio- and stereoselective manner, 1-allyloxycarbonyl-7-ethyl-6β-hydroxy-1,2,4aα,5aα,8aα, 8bα-(±)hexahydro-3,4a-dimethyl- and 1-allyloxycarbonyl-6β-hydroxy-1,2,3,4,4aα,5aα,8aα,8bα-(±)-octahydro-3β,4a, 7-trimethyl-6H-pyrrolo[3',4':4,5]furo[3,2-b]pyrid-8(7H)-one as 6β-hydroxy isomers (cf. Scheme IT):

Scheme II

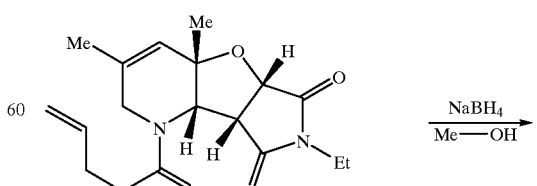

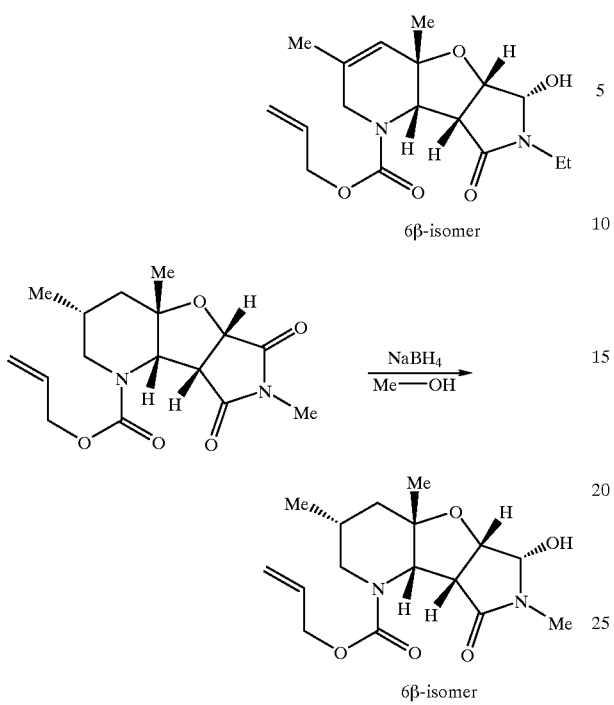

6β-isomer

However, alternatively, the novel 6-hydroxy-1,2,4aα,5aα,8aα,8bα-(±)-hexahydro-6H-pyrrolo[3',4':4,5]furo [3,2-b] pyrid-8(7H)-one derivatives of the general formulae (Ia) can also be obtained, according to process 3, via simultaneous selective hydrogenation of the C═N-double bond in the dihydropyridine moiety and by radio- and stereoselective hydrogenation of an imidcarbonyl function in the pyrrolidine moiety from corresponding 4aα,5aα,8aα,8bα-(±)-tetrahydro-6H-pyrrolo-[3',4':4,5]furo[3,2-b]pyridin-6,8(7H)-dione derivatives of the general formula (III).

Thus, as a further example of the process 2 according to the invention for the radio- and stereoselective preparation of the 6β-isomer of 6-hydroxy-1,2,4aα,5aα,8aα,8bα-(±)-hexahydro-3,4a,7-trimethyl-6H-pyrrolo[3',4':4,5]furo[3,2-b]pyrid-8 (7H)-one of the general formula (Ia) according to the invention, the hydrogenation of 4aα,5aα,8aα, 8bα-(±)-tetrahydrohexahydro-3,4a,7-trimethyl-6H-pyrrolo[3',4':4,5]-furo[3,2-b]pyridine-6,8(7H)-dione is shown (cf. Scheme III).

Scheme III

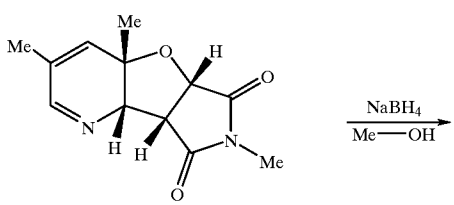

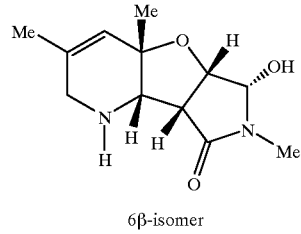

6β-isomer

The formulae (II) and (III) provide general definitions of the compounds required as starting materials for carrying out the process 2 according to the invention. In the formulae, $R^1$, $R^2$, $R^3$, $R^4$, and B preferably represent both radicals which have already been mentioned in connection with the description of the substances of the formula (I) according to the invention as being preferred for these substituents.

Some of the 4aα,5aα,8aα,8bα-(±)-tetrahydro-6H-pyrrolo [3',4':4,5]furo[3,2-b]pyridine-6,8(7H)-dione derivatives to be used as starting materials are already known, and some can be obtained by methods known from the literature (cf., for example: T. Hisano et al. Chem. Pharm. Bull. 35 (3). (1987), p. 1049–1057; Heterocycles 29 (6), (1989), S. 1029–1032; Chem. Pharm. Bull. 38 (3), (1990), S. 605–611; Chem. Pharm. Bull. 39 (1), (1991), S. 10–17 and German Offenlegungsschrift 19 538 960-A1).

Various hydrogenating agents, such as, for example, alkali metal hydrides, in particular sodium borohydride ($NaBH_4$), lithium aluminium hydride ($LiAlH_4$), lithium triethylborohydride ($Li[Et_3 BH]$), lithium tri-sec-borohydride ($Li[sec-Bu_3BH]$), sodium bis(2-methoxyethoxy)aluminium hydride, alkylaluminium hydrides, in particular diisobutylaluminium hydride (DI-BAL-H), or tetramethylammonium triacetoxyborohydride, inter alia, are suitable for hydrogenating the 4a,5a,8a,8b-tetrahydro-6H-pyrrolo[3',4':4,5]furo [3,2-b]pyridine-6,8(7H)-dione derivatives and their salts (cf. H. de Koning, W. N. Speckamp, Houben-Weyl E 21, p. 1953 and the literature cited therein).

It is, of course, also possible to use a "borohydride resin", for example "borohydride on Amberlite® IRA406" for the hydrogenation (cf. Sande A. R. et al. Tetrahedron Lett. 1984, 25, p. 3501).

To carry out the hydrogenation, preference is given to using alkali metal hydrides, in particular sodium borohydride ($NaBH_4$) or lithium aluminium hydride ($LiAlH_4$).

It is generally advantageous to carry out the process 2 according to the invention in the presence of diluents. Diluents are preferably employed in such an amount that the reaction mixture remains stirrable during the entire process. Suitable diluents for carrying out the process 2 according to the invention are all inert organic solvents.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, methyl n-butyl ether, anisole, phenetol, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethyl-, triethyl-, tripropyl-, tributylamine, N-methyl-morpholine, pyridine and tetramethylenediamine, nitrohydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example so-called white spirits containing components having boiling points in the range of, for example, from 40° C. to 250° C., Cymene, benzine fractions within a boiling point range of from 70° C. to 190° C., cyclohexane, methylcyclohexane, petroleum ether, ligroine, octane, benzene, toluene, chlorobenzene, bromobenzene, nitrobenzene, xylene; esters, such as methyl acetate, ethyl acetate, butyl acetate, isobutyl acetate, and dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methyl-caprolactam, 1,3-dimethyl-3,4,5,6-tetrahydro-2(1H)-pyrimidine, octylpyrrolidone, octylcaprolactam, 1,3-dimethyl-2-imidazolinedione, N-formyl-piperidine, N,N'-1,4-diformylpiperazine; ketones, such as acetone, acetophenone, methyl ethyl ketone, methyl butyl ketone.

It is, of course, also possible to employ mixtures of the abovementioned solvents and diluents for the process according to the invention.

Preferred diluents for the hydrogenation are inert organic solvents, such as, for example, alcohols, in particular methanol or ethanol, ethers, in particular tetrahydrofuran and dioxane.

The hydrogenation according to process 2 is carried out by reacting the 4a,5a,8a,8b-tetrahydro-, 1,2,4a,5a,8a,8b-hexahydro- or 1,2,3,4,4a,5a,8a,8b-octahydro- 6H-pyrrolo[3',4':4,5]furo[3,2-b]pyridine-6,8(7H)-dione derivatives of the general formulae (II) and (III) in the presence of a suitable hydrogenating agent, for example sodium borohydride, in one of the diluents mentioned.

The reaction time is from 10 minutes to 48 hours. The reaction is carried out at temperatures between −60° C. and +100° C., preferably between −30° C. and +80° C., particularly preferably at from −10° C. to room temperature. The reaction is carried out under atmospheric pressure and an atmosphere of protective gas (nitrogen or helium).

For carrying out the process 2 according to the invention, generally from 1.0 to 3.0 mol, preferably a slight excess, of hydrogenating agent is employed per mole of the compounds of the general formulae (II) and (III).

After the hydrogenation has ended, the entire reaction mixture is neutralized and concentrated under reduced pressure, and the residue that remains is taken up in a diluent and washed repeatedly. The products obtained can be purified in a customary manner by recrystallization, distillation under reduced pressure or column chromatography (cf. also the Preparation Examples).

As an example of the preparation of suitable salts of compounds of the general formula (Ic), the hydrogen sulphate of 7-ethyl-6β-hydroxy-1,2,4aα,5aα,8aα,8bα-(ž)-hexahydro-3,4a-dimethyl-6H-pyrrolo[3',4':4,5]furo[3,2-b]pyrid-8(7H)-one is shown (cf. Scheme IV):

Scheme IV

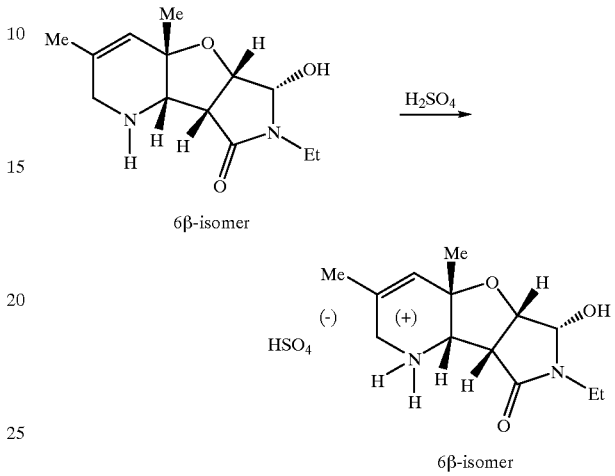

The salt is formed by reacting compounds of the general formula (Ic) in one of the diluents mentioned under process 2 for example in the presence of inorganic acids, such as sulphuric acid.

The reaction time is from 10 minutes to 24 hours. The reaction is carried out at temperatures between −60° C. and +150° C., preferably between −10° C. and +80° C., particularly preferably at from 0° C. to room temperature. The reaction is carried out under atmospheric pressure. To form the salt, generally an excess of acid is employed per mole of the compound of the general formula (Ic).

After the end of the reaction, in most cases the precipitated salt is separated off, washed and dried under reduced pressure (cf. also the Preparation Examples).

Using, for example, in process 2b for preparing the novel 6-hydroxy-1,2,4a,5a,8a,8b-(+/−)-hexahydro-6H-pyrrolo[3',4':4,5]furo[3,2-b]pyrid-8(7H)-ones of the general formula (Ia) the hydrogen sulphate of 7-ethyl-6O-hydroxy-1,2,4aα,5aα,8aα,8bα-(ž)-hexahydro-3,4a-dimethyl-6H-pyrrolo[3',4':4,5]furo[3,2-b]pyrid-8(7H)-one as compound of the general formula (Ic) and allyl chloro
formate as compound of the general formula (V), the process can be represented by the reaction scheme V below:

Scheme V

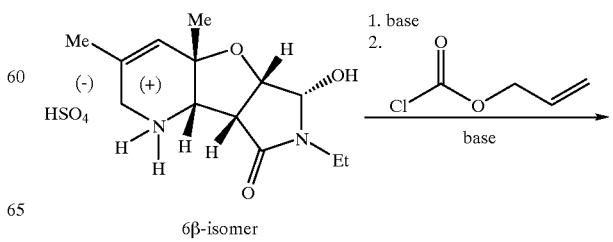

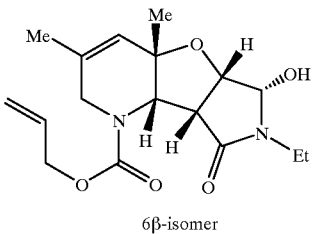

6β-isomer

The formulae (Ic) provide a general definition of the 6-hydroxy-1,2,4a,5a,8a,8b-hexahydro-6H-pyrrolo[3',4':4,5]furo[3,2-b]pyrid-8(7H)-one derivatives and their salts required as starting materials for carrying out the process 2b according to the invention. In these formulae (Ic), $R^1$, $R^2$, $R^3$, $R^4$ preferably represent those radicals which have already been mentioned in connection with the description of the substances of the general formula (I) according to the invention as being preferred for these substituents.

The 6-hydroxy-1,2,4a,5a,8a,8b-hexahydro-6H-pyrrolo[3',4':4,5]furo[3,2-b]pyrid-8(7H)-one derivatives and their salts of the general formula (Ic) used as starting materials are novel, and they can be obtained from the derivatives of the general formulae (III) by the hydrogenation process described further above.

In the formulae (V),

Q and W each have the meaning that has already been mentioned in connection with the description of the substances of the general formula (I) according to the invention as being preferred for these substituents.

The compounds of the formula (V) are generally known compounds of organic chemistry, and/or some of them can be obtained commercially or by methods known from the literature (for example: persubstituted allophanoyl halides: German Offenlegungsschrift 2 008 116; carbamoyl chlorides: Liebigs Ann. 229, p. 85; carbamates: Houben-Weyl, Methoden der organischen Chemie, Volume E 4).

The liberation of the compounds (Ic) from their salts and the subsequent reaction with the compounds of the general formulae (V) is preferably carried out in the presence of a basic reaction auxiliary using diluents.

Suitable diluents for carrying out the process 2b according to the invention are inert aprotic solvents, such as, for example, dioxane, acetonitrile or tetrahydrofuran, and also halogenated hydrocarbons, in particular chlorinated hydrocarbons, such as methylene chloride or chloroform.

Suitable basic reaction auxiliaries for carrying out the process 2b according to the invention are all suitable acid binders, such as amines, in particular tertiary amines, and alkali metal and alkaline earth metal compounds.

Examples which may be mentioned are the hydrides, hydroxides, oxides and carbonates of lithium, sodium, potassium, magnesium, calcium and barium, furthermore other basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2.]octane (DABCO), 1,8-diazabicyclo[5.4.0]undecene (DBU), cyclohexyltetra-butylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyl-toluidine, N,N-dimethyl-p-aminopyridine, N-methyl-pyrrolidine, N-methylpiperidine, N-methylimidazole, N-methylpyrrole, N-methylmorpholine, N-methyl-hexamethylenimine, pyridine, 4-pyrrolidino-pyridine, 4-dimethylamino-pyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine.

Preference is given to using tertiary amines, in particular trialkylamines, such as triethylamine, N,N-diisopropylethylamine, n-propyl-diisopropylamine, N,N'-dimethyl-cyclohexylamine or N-methylmorpholine and also pyridine derivatives, in particular 4-pyrrolidino-pyridine or 4-dimethylaminopyridine.

The process 2b is carried out by initially liberating the compounds of the general formula (Ic) from any salts of the compounds of the general formula (Ic) that may be present, in the presence of a basic reaction auxiliary, and reacting them, in a second reaction step, with compounds of the general formulae (V) in one of the diluents mentioned.

The reaction time is from 4 to 72 hours. The reaction is carried out at temperatures between −10° C. and +150° C., preferably between −5° C. and +80° C., particularly preferably at from 0° C. to room temperature. The reaction is carried out under atmospheric pressure. To carry out the process 2 according to the invention, generally from 1.0 to 3.0 mol, preferably from 1.0 to 1.5 mol, of acylating agent are employed per mole of the compound of the formula (Ic).

After the reaction has ended, the reaction solution is washed and the organic phase is separated off, dried and concentrated under reduced pressure. The resulting products can be purified in a customary manner by recrystallization, vacuum distillation or column chromatography (cf. also the Preparation Examples).

Alternatively, the carbamates can, of course, also be prepared from compounds of the general formulae (Ic) and (Id), carbon dioxide and an alkylating agent of the general formula (IV) in the presence of basic alkali metal, alkaline earth metal or ammonium salts (cf. EP-A 511 948, EP-A 628 542 and literature cited therein, DE-A 19538960.3).

Using, for example, in processes 2d and 2e for preparing the novel 6-hydroxy-1,2,4a,5a,8a,8b-(±)-hexahydro-6H-pyrrolo[3',4':4,5]furo[3,2-b]pyrid-8(7H)-ones of the general formulae (Ia), 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one as compound of the general formula (Ic) and N-benzyloxycarbonylsarkosine (Z-Sar-OH) and methyl isocyanate as compounds of the general formulae (VI) and (VIII), respectively, the processes can be represented by the reaction scheme VI below:

Scheme VI

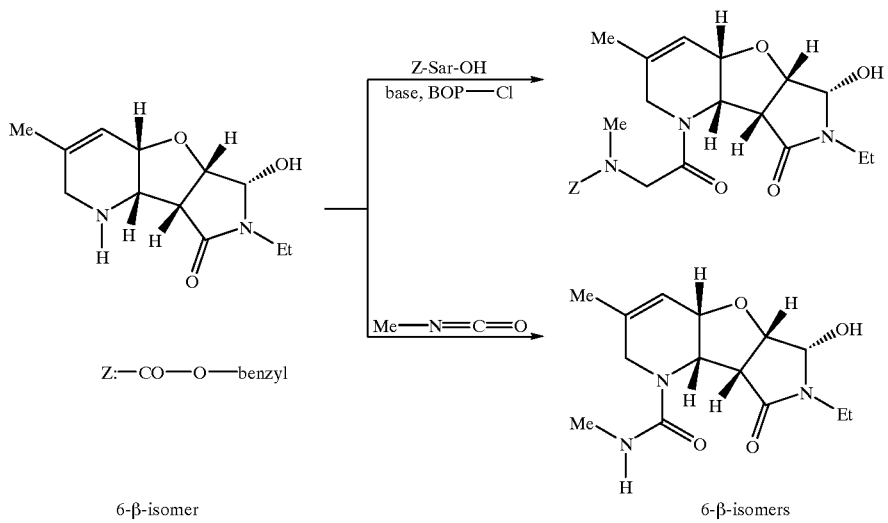

Z:—CO—O—benzyl

6-β-isomer

6-β-isomers

The formulae (Ic) provide a general definition of the 6-hydroxy-1,2,4a,5a,8a,8b-hexahydro-6H-pyrrolo[3',4':4,5]furo[3,2-b]pyrid-8(7H)-one derivatives required as starting materials for carrying out the processes 2d and 2e according to the invention. In these formulae (Ic), $R^1$, $R^2$, $R^3$, $R^4$ each preferably represent those radicals which have already been mentioned in connection with the description of the substances of the general formula (I) according to the invention as being preferred for these substituents.

The formula (VII) provides a general definition of the compounds to be used as starting material in particular for carrying out the process 2d according to the invention.

In this formula (VII), $R^8$, $R^9$, $R^{10}$,

and $Q^1$ each have the meaning which has already been mentioned in connection with the description of the substances of the general formula (I) according to the invention as being preferred for these substituents.

The natural or synthetic amino acids used as starting materials can, if chiral, be present in the (S) or (R) form (or L or D form).

Examples which may be mentioned are:

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gin, Giu, Gly, Guv, hAla, hArg, hCys, hGln, hGlu, His, hule, hIeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ALys, Met, Mim, Min, nArg, Nle, Nva, Oly, Om, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tie, Tly, Trp, Trta, Tyr, Val, Nal, Tbg, Npg, Chg, Thia, (cf., for example, Houben-Weyl, Methoden der Organischen Chemie, Volume XV/1 and 2, Stuttgart, 1974).

Some of the compounds of the general formula (VII) can be obtained commercially or by methods known from the literature (cf., for example: N-methylamino acids: R. Bowmann et al. J. Chem. Soc. (1950) p. 1346; J. R. McDermott et al. Can. J. Chem. 51 (1973) p. 1915; H. Wurziger et al. Kontakte (Merck, Darmstadt) 3 (1987) p. 8).

The reaction of the 6-hydroxy-1,2,4a,5a,8a,8b-hexahydro-6H-pyrrolo(3',4':4,5]furo [3,2-b]pyrid-8(7H)-one derivatives of the general formula (Ic) with amino acid derivatives of the formula (VII) is preferably carried out in the presence of coupling agents and in the presence of a basic reaction auxiliary, using diluents.

Suitable coupling agents for carrying out the process 2d are all those which are suitable for generating an amide bond (cf., for example, Houben-Weyl, Methoden der Organischen Chemie, Volume 1512; Bodansky et al., Peptide Synthesis 2nd ed. (Wiley & Sons, New York 1976) or Gross, Meienhofer, The Peptides: Analysis, Synthesis, Biology (Academic Press, New York 1979). Preference is given to using the following methods: activated ester method using pentachloro- (Pcp) and pentafluorophenol (Pfp), N-hydroxysuccinimide (HOSu), N-hydroxy-5-norbornene-2,3-dicarboxamide (HONB), 1-hydroxy-benzotriazole (HOBt) or 3-hydroxy4-oxo-3,4-dihydro-1,2,3-benzotriazine as alcohol component, coupling with carbodiimides, such as dicyclohexylcarbodiimide (DCCI), by the DCC-additive method, or using n-propanephosphoric anhydride (PPA) and the mixed-anhydride method using pivaloyl chloride, ethyl 1,2-dihydro-2-ethoxy-1-quinolinecarboxylate (EEDQ) and isobutyl 1,2-dihydro-2-isobutoxy-1-quinolinecarboxylate (IIDQ), or coupling with phosphonium reagents, such as benzotriazole-1-yl-oxy-tris(dimethylamino)phosphonium) hexafluorophosphate (BOP), bis(2-oxo-3-oxazolidinyl)-phosphinic chloride (BOP-Cl), benzotriazol-1-yl-tris-pyrrolidino-phosphonium hexafluorophosphate (PyBOP®), bromo-tris-pyrrolidino-phosphonium hexafluorophosphate (PyBroP®, or using phosphonic ester reagents, such as diethyl cyanophosphonate (DEPC) and diphenylphosphoryl azide (DPPA), uronium reagents, such as 2-(1H-benzotriazol-1-yl)1,1,3, 3-tetramethyluronium tetrafluoroborate (TBTU), 2-(5-norbornene-2,3-dicarboxamido)-1,1,3,3-tetramethyluronium tetrafluoroborate (TNTU), 2-(2-oxo-1(2H)-pyridyl)-1,1,3,3-bispentamethylene-tetramethyluronium tetrafluoroborate (TOPPipU), O-(N- succinimidyl)-1,1,3,3-tetramethyluronium tetrafluoroborate (TSTU) or 2-(1H-benzo-triazol-1-yl)- 1,1,3,3-tetramethyluronium hexafluorophosphate (HBTU).

Preference is given to coupling with phosphonium reagents, such as benzotriazol-l-yl-oxy-tris(dimethylamino) phosphonium hexafluorophosphate (BOP), bis(2-oxo-3-oxazolidinyl)-phosphinic chloride (BOP-Cl), benzotriazol-1-yl-tris-pyrrolidino-phosphonium hexafluorophosphate (PyBOP®), bromo-tris-pyrrolidinophosphonium hexafluorophosphate (PyBroP®), and phosphonic acid reagents, such as diethyl cyanophosphonate (DEPC) or diphenylphosphoryl azide (DPPA).

Suitable basic reaction auxiliaries for carrying out the process 2d according to the invention are all acid binders which are also suitable for the process 2b.

Preference is given to using tertiary amines, in particular trialkyl amines, such as triethylamine, N,N-diisopropylethylamine, N-propyldiisopropylamine, N,N'-dimethylcyclohexylamine or N-methylmorpholine.

The solvents used for carrying out the process 2d according to the invention are the solvents mentioned under process 2b, such as, for example, halogenated hydrocarbons, in particular chlorinated hydrocarbons, such as methylene chloride, chloroform, or 1,2-dichloroethane, and mixtures of these with other diluents mentioned.

The process 2d is generally carried out by reacting compounds of the general formula (Ic) in the presence of one of the coupling agents mentioned and in the presence of one of the basic reaction auxiliaries mentioned with compounds of the general formulae (VII), in one of the diluents mentioned.

The reaction time is from 4 to 72 hours. The reaction is carried out at temperatures between –10° C. and +120° C., preferably between –5° C. and +50° C., particularly preferably at from 0° C. to room temperature. The reaction is carried out under atmospheric pressure.

For carrying out the process 2d according to the invention, generally 1.0 to 3.0 mol, preferably 1.0 to 1.5 mol, of coupling reagent are employed per mole of the compound of the formula (Ic).

The formula (VIII) or (IX) provides a general definition of the compounds to be used in particular as starting materials for carrying out the process 2e according to the invention.

In these formulae (VIII) or (IX), $R^{12}$, Y,

and Z each have the meaning which has already been mentioned in connection with the description of the substances of the general formula (I) according to the invention as being preferred for these substituents.

Some of the compounds of the general formula (VIII) or (IX) can be obtained commercially or by methods known from the literature (cf., for example: Houben-Weyl, Methoden der organischen Chemie, Volume E 4).

The reaction of the 6-hydroxy-1,2,4a,5a,8a,8b-hexahydro-6H-pyrrolo[3',4':4,5]furo[3,2-b]pyrid-8(7H)-one derivatives of the general formula (Ic) with compounds of the general formulae (VIII) or (IX) is preferably carried out in the presence of diluents, if appropriate in the presence of a basic reaction auxiliary.

Suitable diluents for carrying out the process 2e according to the invention are the solvents mentioned under process 2b, such as, for example, halogenated hydrocarbons, in particular chlorinated hydrocarbons, such as methylene chloride, chloroform or 1,2-dichloroethane, nitrites, such as acetonitrile, propionitrile, butyronitrile, in particular acetonitrile, ethers, such as ethyl propyl ether, di-n-butyl ether, diethyl ether, dipropyl ether, diisopropyl ether, tetrahydrofuran or dioxane, in particular tetrahydrofuran or dioxane, aliphatic or aromatic hydrocarbons, such as n-hexane, n-heptane, benzene, toluene or xylenes, and mixtures of these with other diluents mentioned.

The process 2e can also be carried out in the presence of basic reaction auxiliaries. Suitable basic reaction auxiliaries for carrying out the process 2e according to the invention are all of the acid binders mentioned further above, but preferably tertiary amines, in particular trialkylamines, such as triethylamine, N,N-diisopropylethylamine or N-methylmorpholine, and amidine bases or guanidine bases, such as diazabicyclo[4.3.0]nonene (DBN), diazabicyclo[2.2.2]octane (DABCO), 1,8-diazabicyclo[5.4.0]undecene (DBU), in particular 1,8-diazabicyclo[5.4.0]undecene (DBU).

The process 2e is generally carried out by reacting compounds of the general formula (Ic) with compounds of the general formulae (VIII) or (IX), if appropriate in the presence of one of the basic reaction auxiliaries mentioned, with compounds of the general formulae (VIII), in one of the solvents mentioned.

The reaction time is from 4 to 72 hours. The reaction is carried out at temperatures between –10° C. and +180° C., preferably between –5° C. and +120° C., particularly preferably at from 0° C. to the boiling point of the diluent used.

In principle, the reaction can be carried out under atmospheric pressure; however, it is also possible to operate under elevated or reduced pressure. The process is preferably carried out at atmospheric pressure or superatmospheric pressure of up to 15 bar.

For carrying out the process 2e according to the invention, generally 1.0 to 3.0 mol, preferably 1.0 to 1.5 mol, of compound of the general formula (VIII) or (IX) is employed per mole of the compound of the formula (Ic).

After the reaction has ended, the reaction solution is washed and the organic phase is separated off, dried and concentrated under reduced pressure. The resulting products can be purified in a customary manner by recrystallization, vacuum distillation or column chromatography (cf. also the Preparation Examples).

Using, for example, in the process 3a for preparing the novel 6-substituted 1,2,4a,5a,8a,8b-hexahydro-/1,2,3,4,4a,5a,8a,8b-octahydro-6H-pyrrolo[3',4':4,5]furo[3,2-b]pyrid-8 (7H)-one derivatives of the general formulae (I), 1-allyloxycarbonyl-6β-hydroxy-1,2,4aα,5aα,8aα,8bα-(±)-hexahydro-3,4a,7-trimethyl- and 1-allyloxycarbonyl-6β-hydroxy-1,2,4aα,5aα,8aα,8bα-(±)-octahydro-3,4a,7-trimethyl-6H-pyrrolo[3',4':4,5]furo[3,2-b]pyrid-8(7H)-one as compounds of the general formulae (Ia) and (Ib) and ethanol ($R^{16}$: -ethyl; X: —O—) or aqueous sodium hydroxide solution ($R^{16}$: —H; X: —O—) as compounds of the general formula (X), the process can be represented by the reaction scheme VII below:

Scheme VII

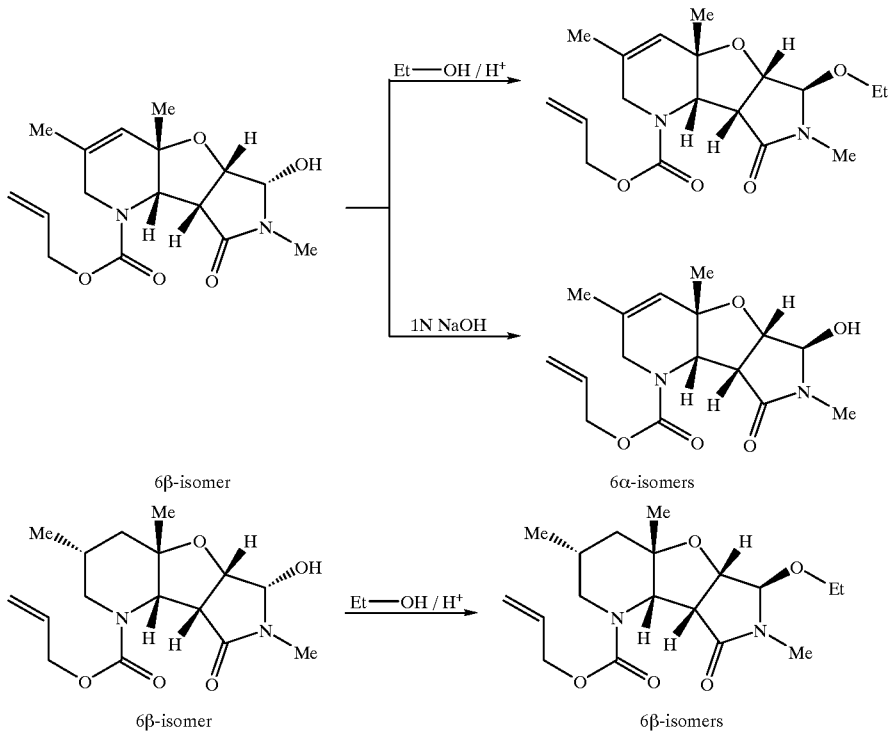

6β-isomer     6α-isomers

6β-isomer     6β-isomers

When using the 6β-isomers of compounds of the general formulae (Ia) and (Ib), an inversion in the 6 position, with formation of the corresponding 6α-isomers, may occur in the process 3 according to the invention.

The formulae (Ia) and (Ib) provide general definitions of the 6-hydroxy-1,2,4a,5a,8a,8b-hexahydro-/1,2,3,4,4a,5a,8a,8b-octahydro-6H-pyrrolo[3,4':4,5]furo[3,2-b]pyrid-8(7H)-one derivatives required as starting materials for carrying out the process 3a according to the invention. In these formulae (Ia) and (Ib), $R^1$, $R^2$, $R^3$, $R^4$ and B each preferably represent those radicals which have already been mentioned in connection with the description of the substances of the general formula (I) according to the invention as being preferred for these substituents.

The 6-hydroxy-1,2,4a,5a,8a,8b-hexahydro-/1,2,3,4,4a,5a, 8a,8b-octahydro-6H-pyrrolo[3',4':4,5]furo[3,2-b]pyrid-8 (7H)-one derivatives of the general formulae (Ia) and (Ib) to be used as starting materials are novel and can be obtained from the 1,2,4a,5a,8a,8b-hexahydro-/1,2,3,4,4a,5a,8a,8b-octahydro-6H-pyrrolo[3',4':4,5]furo[3,2-b]pyrid-6,8(7H)-dione derivatives of the general formulae (II) and (III) by the hydrogenation process described further above.

The formula (X) provides a general definition of the compounds furthermore to be used as starting materials for carrying out the process 3a according to the invention.

In the formula (X), $R^{16}$ and X each have the meaning that has already been mentioned in connection with the description of the substances of the general formula (I) according to the invention as being preferred for these substituents.

In general, it is advantageous to carry out the process 3a according to the invention in the presence of diluents and, if appropriate, in the presence of an acidic or basic reaction auxiliary.

Suitable diluents for carrying out the process 3a according to the invention are all inert solvents mentioned under process 2.

Preferred diluents are inert organic solvents, such as, for example, alcohols, in particular methanol, ethanol, propanol and butanol.

Suitable reaction auxiliaries for carrying out the process 3a according to the invention are all suitable mineral acids. These include virtually all mineral acids. The mineral acids preferably include hydrohalic acids, such as hydrofuric acid, hydrobromic acid, hydrochloric acid or hydriodic acid, and also sulphuric acid, sulphinic acid, phosphoric acid, phosphinic acid and nitric acid.

Preference is given to using sulphuric acid and hydrochloric acid for carrying out the process 3a according to the invention.

The process 3a is carried out by reacting compounds of the general formulae (Ia) and (Ib) in the presence of an acidic reaction auxiliary with compounds of the general formula (X), in one of the diluents mentioned.

The reaction time is from 30 minutes to 48 hours. The reaction is carried out at temperatures between −60° C. and +100° C., preferably between −30° C. and +80° C., particularly preferably at from −10° C. to room temperature. The reaction is carried out under atmospheric pressure.

For carrying out the process 3a according to the invention, generally an excess of compounds of the general formula (X) and a catalytic amount of reaction auxiliary is employed per mole of compounds of the general formulae (Ia) and (Ib).

After the reaction has ended, the entire reaction solution is neutralized and concentrated under reduced pressure, and the residue that remains is taken up in one of the diluents mentioned and washed. The organic phase is separated off and once more concentrated, and the resulting products can be purified in a customary manner by recrystallization, vacuum distillation or column chromatography (cf. also the Preparation Examples).

Alternatively, the 6-alkoxy derivatives can also be obtained in a two-step reaction via O-mesylation in the presence of a base, followed by reaction with the corresponding alcohol (cf. W. N. Speckamp, H. Hiemstra, Tetrahedron, Vol. 41, No. 20 (1985), pp. 4367–4416).

If in the processes 3b and 3c for preparing the novel 6-substituted 1,2,4a,5a,8a,8b-hexahydro-6H-pyrrolo[3',4':4,5]furo[3,2-b]pyrid-8(7H)-one derivatives of the general formulae (Ie) 1-allyloxycarbonyl-6D-hydroxy-1,2,4aα,5aα,8aα,8bα-(ž)-hexahydro-3,4a,7-trimethyl-6H-pyrrolo[3',4':4,5]furo[3,2-b]pyrid-8(7H)-one is used as compound of the general formula (Ia) and cyclopropanecarbonyl chloride as compound of the general formula (V) and acetic anhydride as compound of the general formula (VI), the processes can be represented by the reaction scheme VIII below:

Scheme VIII

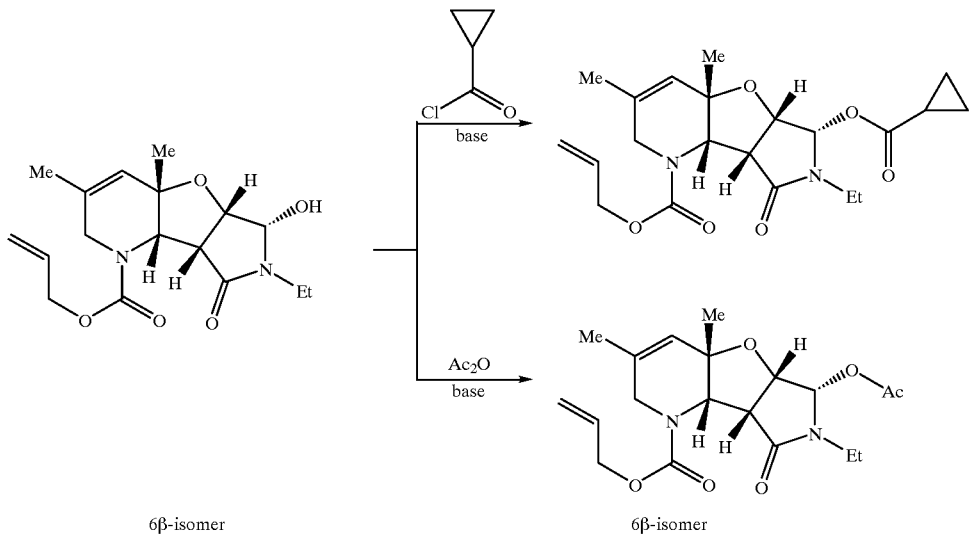

6β-isomer          6β-isomer

In most of the acylations according to the invention, an inversion at the 6 position does not occur, or the 6β isomer is formed in excess, when compounds of the general formula (Ie) are used as 6β-isomers.

The formula (Ia) provides a general definition of the 6-hydroxy-1,2,4a,5a,8a,8b-hexahydro-/1,2,3,4,4a,5a,8a,8b-octahydro-6H-pyrrolo[3',4':4,5]furo[3,2-b]pyrid-8(7H)-one derivatives required as starting materials for carrying out the process 3 according to the invention. In this formula (Ia), $R^1, R^2, R^3, R^4$ and B each preferably represent those radicals which have already been mentioned in connection with the description of the substances of the general formula (I) according to the invention as being preferred for these substituents.

The 6-hydroxy-1,2,4a,5a,8a,8b-hexahydro-6H-pyrrolo[3',4':4,5]furo[3,2-b]pyrid-8(7H)-one derivatives of the general formula (Ia) used as starting materials are novel, and they can be obtained from the corresponding 1,2,4a,5a,8a,8b-hexahydro-6H-pyrrolo[3',4':4,5]furo[3,2-b]pyrid-6,8(7H)-dione derivatives of the general formula (III) by the hydrogenation process described further above.

If, however, the processes 3e and 3f for preparing the novel 6-substituted 1,2,4a,5a,8a,8b-hexahydro-6H-pyrrolo[3',4':4,5]furo[3,2-b]pyrid-8(7H)-one derivatives of the general formulae (Ie) and (Ig) 7-alkyl-6β-hydroxy-1,2,4aα,5aα,8aα,8bα-(ž)-hexahydro-3,4a-dimethyl-6H-pyrrolo[3',4':4,5]furo[3,2-b]pyrid-8(7H)-ones are used as compounds of the general formula (Ic) and allyl chloroformate is used as compound of the general formula (V) and N-benzyloxycarbonyl-N-methyl-leucine (Z-MeLeu-OH) is used as compound of the general formula (VII), the processes can be represented by the reaction scheme IX below:

Scheme IX

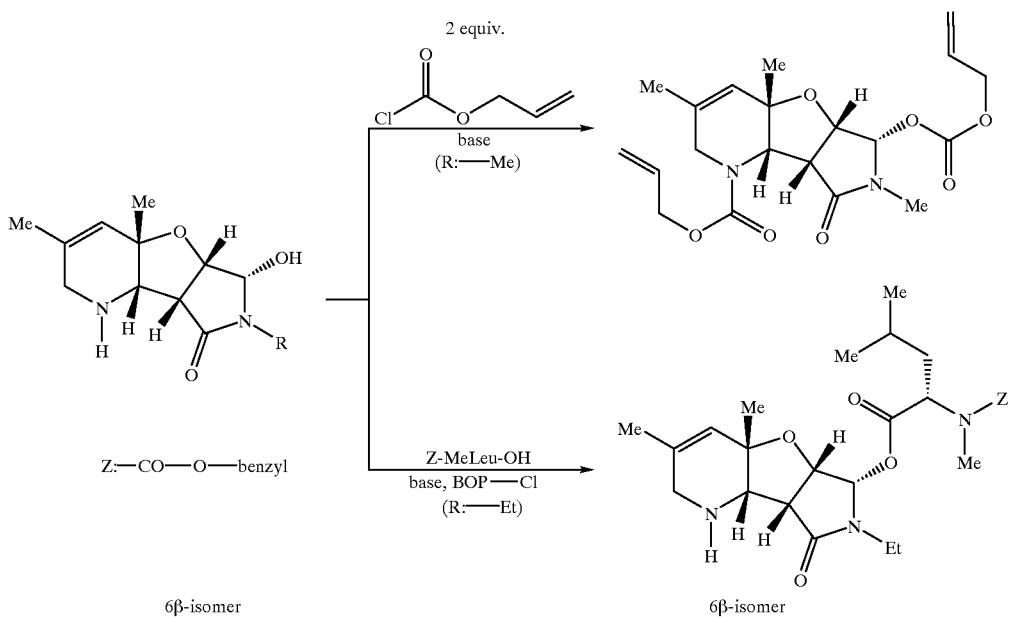

Z:—CO—O—benzyl

6β-isomer

6β-isomer

The formulae (V) and (VII) provide general definitions of the compounds furthermore to be used as starting materials for carrying out the processes 3e and 3f according to the invention.

In the formulae (V) and (VII),

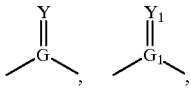

Q and W, $R^8$, $R^9$ and $R^{10}$ each have those meanings which have already been mentioned in connection with the description of the substances of the general formula (I) according to the invention as being preferred for these substituents.

The compounds of the formula (V) are generally known compounds of organic chemistry, and/or some of them can be obtained commercially or by methods known from the literature (for example: persubstituted allophanoyl halides: German Offenlegungsschrift 2 008 116; carbamoyl chlorides: Liebigs Ann. 229, p. 85; carbamates: Houben-Weyl, Methoden der organischen Chemie, Volume E 4).

The natural or synthetic amino acids of the formula (VI) used are likewise generally known compounds of organic chemistry, and some of them can be obtained commercially or by methods known from the literature (cf. process 2d).

The reaction of the compounds (Ic) with the compounds of the general formulae (V) is preferably carried out in the presence of basic reaction auxiliaries, using diluents.

Suitable basic reaction auxiliaries for carrying out the process 3e of the invention are all acid binders mentioned under process 2, such as amines, in particular tertiary amines, and also alkali metal and alkaline earth metal compounds.

In the process 3e, preference is given to using tertiary amines, in particular trialkylamines, such as triethylamine, N,N-diisopropylethylamine, n-propyldiisopropylamine, N,N'-dimethylcyclohexylamine or N-methylmorpholine, and also pyridine derivatives, in particular pyridine, 4-pyrrolidino-pyridine or 4-dimethylaminopyridine.

It is, of course, also possible to use mixtures of the acid binders mentioned for the process 3e according to the invention.

Suitable diluents for carrying out the process 3e according to the invention are the inert aprotic solvents mentioned under process 2, such as, for example, dioxane, acetonitrile or tetrahydrofuran, but also halogenated hydrocarbons, in particular chlorinated hydrocarbons, such as methylene chloride or chloroform.

The process 3e is carried out by reacting compounds of the general formula (Ia) in the presence of basic reaction auxiliaries with compounds of the general formulae (V) and (VI) in one of the diluents mentioned.

The reaction time is from 4 to 72 hours. The reaction is carried out at temperatures between −10° C. and +150° C., preferably between −5° C. and +80° C., particularly preferably at from 0° C. to room temperature. The reaction is carried out under atmospheric pressure. For carrying out the process 3e according to the invention, generally from 2.0 to 6.0 mol, preferably from 2.0 to 3.0 mol, of acylating agent are employed per mole of the compound of the formula (Ia).

The reaction of the 7-alkyl-6hydroxy-1,2,4a,5a,8a,8b-hexahydro-3,4a-dimethyl-6H-pyrrolo[3',4':4,5]furo[3,2-b]pyrid-8(7H)-one derivatives of the general formula (Ic) with the amino acid derivatives of the formula (VII) is preferably carried out in the presence of coupling agents and in the presence of a basic reaction auxiliary, using diluents.

Suitable coupling agents for carrying out the process 3f are all coupling agents which are also suitable for the process 2d.

Preference is given to coupling with phosphonium reagents, such as benzotriazol-1-yl-oxy-tris(dimethylamino) phosphonium hexafluorophosphate (BOP), bis(2-oxo-3-oxazolidinyl)-phosphonyl chloride (BOP-Cl), benzotriazol-1-yl-tris-pyrrolidinophosphonium hexafluorophosphate (PyBOP®), bromo-tris-pyrrolidinophosphonium hexafluorophosphate (PyBroP®), and phosphonic acid reagents, such as diethyl cyanophosphonate (DEPC) or diphenylphosphoryl azide (DPPA).

Suitable basic reaction auxiliaries for carrying out the process 3f according to the invention are all acid binders which are also suitable for process 2d.

Preference is given to using tertiary amines, in particular trialkylamines, such as triethylamine, N,N-diisopropylethylamine, n-propyldiisopropylamine, N,N'-dimethylcyclohexylamine or N-methylmorpholine.

Suitable diluents for carrying out the process 3f according to the invention are the diluents mentioned under process 2d, such as, for example, halogenated hydrocarbons, in particular chlorinated hydrocarbons, such as methylene chloride, chloroform or 1,2-dichlorethane and mixtures of these with other diluents mentioned.

The process 3f is generally carried out by reacting compounds of the general formula (Ic) in the presence of one of the coupling agents mentioned and in the presence of one of the basic reaction auxiliaries mentioned with compounds of the general formulae (VII), in one of the diluents mentioned.

If in the process 4a for preparing the novel 6-substituted 1,2,4a,5a,8a,8b-(ž)-hexahydro- and 6-substituted 1,2,3,4,4a,5a,8a,8b-(±)-octahydro-6H-pyrrolo[3',4':4,5]furo[3,2-b]pyrid-8(7H)-one derivatives of the general formulae (Ig,h), 1-allyloxycarbonyl-6β-hydroxy-1,2,4aα,5aα,8aα,8bα-(±)-hexahydro-3,4a,7-trimethyl6H-pyrrolo[3',4':4,5]furo[3,2-b]pyrid-8(7H)-one is used as compound of the general formula (Ia) or 1-allyloxycarbonyl-6α-ethoxy-7-ethyl-1,2,4aα,5aα,8aα,8bα-(ž)-hexahydro-3,4a-dimethyl- and 1-allyloxycarbonyl-6α-ethoxy-1,2,3,4,4aα,5aα,8aα,8bα-(ž)-octahydro-3β,4a,7-trimethyl-6H-pyrrolo[3',4':4,5]furo[3,2-b]pyrid-8(7H)-one are employed as compounds of the general formulae (Ie, If) and allyl trimethylsilane is employed as compound of the general formula (X), the process can be represented by the reaction scheme X below:

Scheme X

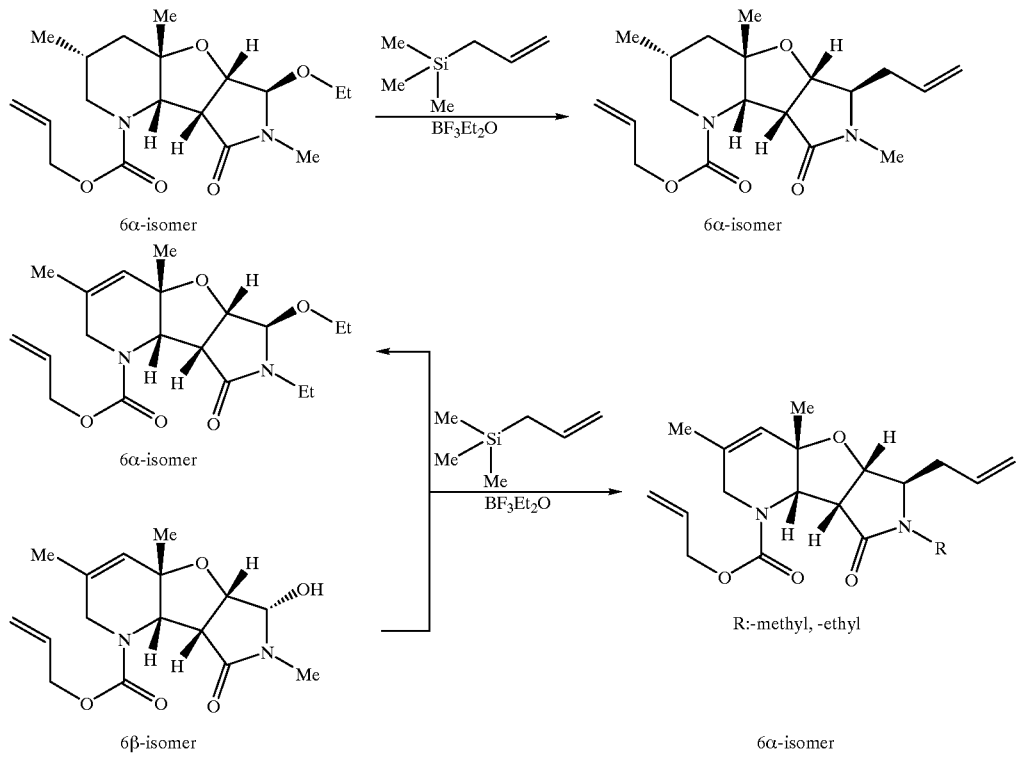

The reaction time is from 4 to 72 hours. The reaction is carried out at temperatures between −10° C. and +120° C., preferably between −5° C. and +50° C., particularly preferably at from 0° C. to room temperature. The reaction is carried out under atmospheric pressure.

For carrying out the process 3f according to the invention, generally from 1.0 to 3.0 mol, preferably from 1.0 to 1.5 mol, of coupling agent are employed per mole of compound of the formula (Ic).

After the reaction has ended, the reaction solution is washed and the organic phase is separated off, dried and concentrated under reduced pressure. The resulting products can be purified in a customary manner by recrystallization, vacuum distillation or column chromatography (cf. also the Preparation Examples).

The formulae (Ia,b) provide a general definition of the 6-hydroxy-1,2,4a,5a,8a,8b-hexahydro- and 6-hydroxy-1,2,3,4,4a,5a,8a,8b-octahydro-6H-pyrrolo[3',4':4,5]furo-[3,2-b]pyrid-8(7H)-one derivatives required as starting materials for carrying out the process 4a according to the invention.

The formulae (Ie, f) provide a general definition of the 6-ethoxy-1,2,4a,5a,8a,8b-hexahydro- and 6-ethoxy-1,2,3,4,4a,5a,8a,8b-octahydro-6H-pyrrolo[3',4':4,5]furo[3,2-b]pyrid-8(7H)-one derivatives furthermore required as starting materials for carrying the process 4a according to the invention.

In these formulae (Ia,b) and (Ie,f), $R^1$, $R^2$, $R^3$, $R^4$, $R^{16}$, X and B each preferably represent those radicals which have already been mentioned in connection with the description of the substances of the general formula (I) according to the invention as being preferred for these substituents.

The 6-hydroxy-1,2,4a,5a,8a,8b-hexahydro- and 6-hydroxy-1,2,3,4,4a,5a,8a,8b-octahydro-6H-pyrrolo[3', 4':4,5]furo[3,2-b]pyrid-8 (7H)-one derivatives of the general formulae (Ia,b) and the 6-alkoxy-1,2,4a,5a,8a,8b-hexahydro- and 6-alkoxy-1,2,3,4,4a,5a,8a,8b-octahydro-6H-pyrrolo[3',4':4,5]furo[3,2-b]pyrid-8(7H)-one derivatives of the general formulae (Ie,f) used as starting materials are novel, and they can be obtained by the processes described further above.

The formula (X) provides a general definition of the compounds furthermore to be used as starting materials for carrying out the process 4a according to the invention.

In the formula (X), $R^{17}$, $R^{18}$ and M each have the meaning that has already been mentioned in connection with the description of the substances of the general formula (I) according to the invention as being preferred for these substituents.

The organometallic compounds of the formula (XI) are generally known compounds of organic chemistry, and some of them can be obtained commercially or by methods known from the literature (cf. Houben-Weyl, Methoden der organischen Chemie, Volume 13/5 and 13/6, 1980).

The reaction of the compounds (Ia,b) and (Ie,f) with the compounds of the general formula (X) is preferably carried out in the presence of a catalyst, using solvents (cf. also Houben-Weyl, Methoden der organischen Chemie, Volume E 21, p. 1968).

Suitable catalysts for carrying out the process 4a according to the invention are all suitable Lewis acids, such as aluminium chloride, boron trifluoride or its etherate, di(isopropyloxy)titanium(IV) dichloride, titanium(IV) chloride, tin(IV) chloride, tin(II) triflate, zinc(II) chloride, zinc(II) bromide, magnesium(II) bromide, ethyl aluminium dichloride or trimethylsilyl triflate.

Preferred Lewis acids are boron trifluoride or its etherate and titanium(IV) chloride.

Suitable diluents for carrying out the process 4a according to the invention are the inert aprotic solvents mentioned under process 2, such as, for example, ethers, dioxane, acetonitrile or tetrahydrofuran, halogenated hydrocarbons, in particular chlorinated hydrocarbons, such as methylene chloride or chloroform, but also aromatic hydrocarbons, such as benzene or toluene.

The process 4a is carried out by reacting compounds of the general formulae (Ia,b) or (Ie,f) in the presence of a catalyst with compounds of the general formulae (XI) in one of the diluents mentioned.

The reaction time is from 1 to 48 hours. The reaction is carried out at temperatures between −150° C. and +100° C., preferably between −100° C. and +50° C., particularly preferably at from −85° C. to room temperature. The reaction is carried out under atmospheric pressure and an atmosphere of protective gas. To carry out the process 4a according to the invention, generally 1.0 to 5.0 mol, preferably 1.5 to 3.0 mol, of an organometallic compound of the formula (XI) is employed per mole of the compound of the formulae (Ia,b) or (Ie,f).

After the reaction has ended, the reaction solution is washed and the organic phase is separated off, dried and concentrated under reduced pressure. The resulting products can be purified in a customary manner by recrystallization, vacuum distillation or column chromatography (cf. also the Preparation Examples).

If in the process 4b for preparing the novel 6-substituted 1,2,4a,5a,8a,8b-(ž)-hexahydro-6H-pyrrolo[3',4':4,5]furo[3,2-b]pyrid-8(7H)-one derivatives of the general formulae (Ii) 1-allyl-oxycarbonyl-6α-ethoxy-7-ethyl-1,2,4aα,5aα,8aα,8bα-(ž)-hexahydro-3,4a-dimethyl-6H-pyrrolo[3',4':4,5]furo[3,2-b]pyrid-8(7H)-one is employed as compound of the general formula (Ie) and 1-phenyltrimethylsiloxyethylene is employed as compound of the general formula (XI), the process can be described by the reaction scheme XI below:

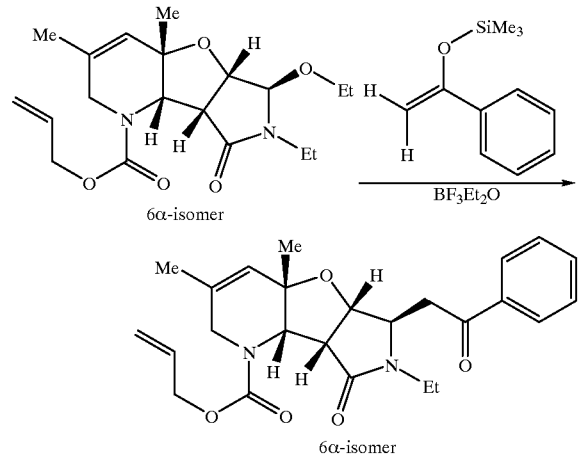

The formulae (Ie) provide general definitions of the 6-alkoxy-1,2,4a,5a,8a,8b-hexahydro-6H-pyrrolo[3',4':4,5]furo[3,2-b]pyrid-8(7H)-one derivatives requires as starting materials for carrying out the process 4b according to the invention.

In this formula (Ie), $R^1$, $R^2$, $R^3$, $R^4$, $R^{16}$, X and B each preferably represent those radicals which have already been mentioned in connection with the description of the substances of the general formula (I) according to the invention as being preferred for these substituents.

The 6-alkoxy-1,2,4a,5a,8a,8b-hexahydro-6H-pyrrolo[3',4':4,5]furo[3,2-b]pyrid-8(7H)-one derivatives of the general formulae (Ie) used as starting materials are novel and they can be obtained by the processes described further above.

The formula (XII) provides a general definition of the compounds furthermore to be used as starting materials for carrying out the process 4b according to the invention.

In the formula (XII), $R^6$, $R^7$ and $R^{19}$ each have the meaning which has already been mentioned in connection with the description of the substances of the general formula (I) according to the invention as being preferred for these substituents.

The compounds of the formula (XII) are generally known compounds of organic chemistry, and some of them can be obtained commercially or by methods known from the literature (cf. Houben-Weyl, Methoden der organischen Chemie, Volume 13/5 and 13/6, 1980).

The reaction of the compounds (Ie) with the compounds of the general formula (XII) is preferably carried out in the presence of a catalyst and using diluents.

Suitable catalysts for carrying out the process 4b according to the invention are all Lewis acids which are also suitable for the process 4a.

Preferred Lewis acids for the process 4b are boron trifluoride or its etherate, titanium(IV) chloride or tin(IV) chloride.

Suitable diluents for carrying out the process 4b according to the invention are the inert aprotic solvents mentioned under process 2, such as, for example, ethers, dioxane, acetonitrile or tetrahydrofuran, halogenated hydrocarbons, in particular chlorinated hydrocarbons, such as methylene chloride or chloroform, but also aromatic hydrocarbons, such as benzene or toluene.

The process 4b is carried out by reacting compounds of the general formulae (Ie) in the presence of a catalyst with compounds of the general formulae (XII) in one of the diluents mentioned.

The reaction time is from 1 to 48 hours. The reaction is carried out at temperatures between −150° C. and +100° C., preferably between −100° C. and +50° C., particularly preferably at from −85° C. to room temperature. The reaction is carried out under atmospheric pressure and an atmosphere of protective gas. To carry out the process 4b according to the invention, generally 1.0 to 5.0 mol, preferably 1.5 to 3.0 mol, of the compound of the formula (XII) are employed per mole of the compound of the formula (Ie).

After the reaction has ended, the reaction solution is washed and the organic phase is separated off, dried and concentrated under reduced pressure. The resulting products can be purified in a customary manner by recrystallisation, vacuum distillation or column chromatography (cf. also the Preparation Examples).

If in the process 4c for preparing the novel 6-substituted 1,2,4a,5a,8a,8b-(±)-hexahydro- and 6-substituted 1,2,4a,5a, 8a,8b-(±)-octahydro-6H-pyrrolo[3',4':4,5]furo[3,2-b]pyrid-8(7H)-one derivatives of the general formulae (Ig,h) 1-allyloxycarbonyl-6α-ethoxy-7-ethyl-1,2,4aα,5aα,8aα, 8bα-(±)-hexahydro-3,4a-dimethyl-6H-pyrrolo[3',4':4,5]furo [3,2-b] pyrid-8(7H)-one is used as compound of the general formula (Ie) and furan is used as compound of the general formula (XIII), the process can be represented by the reaction scheme (XII):

Scheme XII

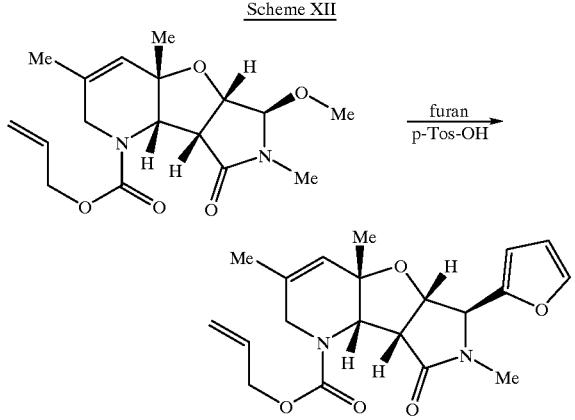

The formulae (Ie) provide a general definition of the 6-alkoxy-1,2,4a,5a,8a,8b-hexahydro-6H-pyrrolo[3',4':4,5] furo[3,2-b]pyrid-8(7H)-one derivatives required as starting materials for carrying out the process 4c according to the invention.

In this formula (Ie), $R^1$, $R^2$, $R^3$, $R^4$, $R^{16}$, X and B each preferably represent those radicals which have already been mentioned in connection with the description of the substances of the general formula (I) according to the invention as being preferred for these substituents.

The 6alkoxy-1,2,4a,5a,8a,8b-hexahydro-6H-pyrrolo[3', 4':4,5]furo[3,2-b]pyrid-8(7H)-one derivatives of the general formulae (Ie) used as starting materials are novel and they can be obtained by the processes described further above.

The formula (XIII) provides a general definition of the compounds furthermore to be used as starting materials for carrying out the process 4c according to the invention.

In the formula (XIII), $R^{17}$ has the meaning that has already been mentioned in connection with the description of the substances of the general formula (I) according to the invention as being preferred for these substituents.

The compounds of the formula (XIII) are generally known compounds of organic chemistry, and some of them can be obtained commercially or by methods known from the literature (cf. furans: P. Bosshard, C. H. Engster in: Advances Heterocycl. Chem.; Ed.: A. R. Katritzky, A. J. Boulton, Vol. 7, New York, Academic Press 1966, p. 377).

The reaction of the compounds (Ie) with the compounds of the general formula (XIII) is preferably carried out in the presence of a catalyst, using diluents.

Suitable catalysts for carrying out the process 4c according to the invention are all acids which are also suitable for the process 3.

Preferred acids for the process 4c are mineral acids, in particular sulphuric acid, or organic acids, in particular acetic acid or sulphonic acids, such as para-toluenesulphonic acid or β-naphthalenesulphonic acid.

Suitable diluents for carrying out the process 4c according to the invention are the inert aprotic solvents mentioned under process 3, such as, for example, ethers, dioxane, acetonitrile or tetrahydrofuran, halogenated hydrocarbons, in particular chlorinated hydrocarbons, such as methylene chloride or chloroform, but also aromatic hydrocarbons, such as benzene or toluene. However, it is also advantageous to employ only the compounds of the general formula (XIII), in equimolar amounts or in excess.

The process 4c is carried out by reacting compounds of the general formulae (Ie) in the presence of a catalyst with compounds of the general formulae (XIII), if appropriate in one of the diluents mentioned.

The reaction time is from 1 to 48 hours. The reaction is carried out at temperatures between −100° C. and +100° C., preferably between −50° C. and +50° C., particularly preferably at from −10° C. to room temperature. The reaction is carried out under atmospheric pressure. To carry out the process 7c according to the invention, generally from 1.0 to 5.0 mol, preferably from 1.5 to 3.0 mol, of a compound of the formula (XII) are employed per mole of a compound of the formula (Ie).

After the reaction has ended, the reaction solution is washed and the organic phase is separated off, dried and concentrated under reduced pressure. The resulting products can be purified in a customary manner by recrystallization, vacuum distillation or column chromatography (cf. also the Preparation Examples).

Using the processes 2, 3 and 4 according to the invention, compounds according to the invention in which the original configuration of the starting materials is retained are obtainable from the individual building blocks having both (S) and (R) configuration (or L and D configuration). However, depending on the starting materials used, it is also feasible to carry out a targetted inversion in position 6 of the compounds according to the invention.

The "inert solvents" referred to in the above process variants 2, 3 and 4 are taken in each case to mean solvents which are inert under the particular reaction conditions, but do not have to be inert under any reaction conditions.

The active compounds are suitable for controlling pathogenic endoparasites which occur in humans and in stock, breeding, zoo, laboratory and test animals and pets in animal husbandry and animal breeding, having favorable toxicity to warm-blooded animals. They are active here against all or individual stages of development of the pests and against resistant and normally sensitive species. By controlling the pathogenic endoparasites, disease, fatalities and reductions in productivity (for example in the production of meat, milk, wool, hides, eggs, honey and the like) are to be diminished, so that more economic and easier animal husbandry is possible by use of the active compounds. The pathogenic endoparasites include cestodes, trematodes, nematodes, acantocephalae, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia sp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp-, Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomun spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filarilda, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example: Filicollis spp., Moniliformis spp., Macracanthorhynchus spp., Prosthenorchis spp.

The stock and breeding animals include mammals such as for example, cattle, horses, sheep, pigs, goats, camels, water buffalo, donkeys, rabbits, fallow deer, reindeer, fur-bearing animals, such as, for example, mink, chinchillas, racoons, birds, such as, for example, chickens, geese, turkeys, ducks, fresh water and salt-water fishes, such as, for example, trout, carp, eels, reptiles, insects, such as, for example, honey bees and silk worms.

Laboratory and test animals include mice, rats, guineapigs, golden hamsters, dogs and cats.

Pets include dogs and cats.

The compounds can be used both prophylactically and therapeutically.

The active compounds are used, directly or in the form of suitable formulations, enterally, parenterally, dermally, nasally, by treatment of the enviromnent or with the aid of molded articles containing the active compound, such as, for example, strips, sheets, tapes, collars, ear marks, limb tapes, marking devices. Enteral use of the active compounds is effected, for example, orally, in the form of powders, tablets, capsules, pastes, drinks, granules, orally administerable solutions, suspensions and emulsions, boli, medicated feed or drinking water. Dermal use is effected, for example, in the form of dips, sprays or pour-on and spot-on formulations. Parenteral use is effected, for example, in the form of injection (intramuscular, subcutaneous, intravenous, intraperitoneal) or by implants.

Suitable formulations are:

Solutions, such as injection solutions, oral solutions, concentrates for oral administration after dilution, solutions for use on the skin or in body cavities, pour-on formulations, gels;

emulsions and suspensions for oral or dermal use and for injection; semi-solid formulations;

formulations in which the active compound is processed in an ointment base or in an oil-in-water or water-in-oil emulsion base;

Solid formulations, such as powders, premixes or concentrates, granules, pellets, tablets, boli, capsules, aerosols and inhalates, molded articles containing the active compound.

Injection solutions are administered intravenously, intramuscularly and subcutaneously.

Injection solutions are prepared by dissolving the active compound in a suitable solvent and if necessary adding additives, such as solubilizing agents, acids, bases, buffer salts, antioxidants, preservatives. The solutions are subjected to sterile filtration and bottled.

Solvents which may be mentioned are: physiologically tolerated solvents, such as water, alcohols, such as ethanol, butanol, benzylalcohol, glycerol, propylene glycol, polyethylene glycols, N-methyl-pyrrolidone, and mixtures thereof.

If appropriate, the active compounds can also be dissolved in physiologically tolerated vegetable or synthetic oils which are suitable for injection.

Solubilizing agents which may be mentioned are: solvents which promote the solution of the active compound in the main solvent or prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic acid esters, n-butanol.

Oral solutions are used directly. Concentrates are used orally after prior dilution to the use concentration. Oral solutions and concentrates are prepared as described above for the injection solutions, but sterile working can be omitted.

Solutions for use on the skin are dripped or brushed on, massaged in, sprinkled on or sprayed on. These solutions are prepared as described above for the injection solutions.

It may be advantageous to add thickeners during the preparation. Thickeners are: inorganic thickeners, such as bentonites, colloidal silicic acid, aluminium monostearate, organic thickeners, such as cellulose derivatives, polyvinyl alcohols and copolymers thereof, acrylates and methacrylates.

Gels are applied to or spread on the skin or introduced into body cavities. Gels are prepared by adding to solutions which have been prepared as described for the injection solutions, an amount of thickeners such that a clear composition having an ointment-like consistency is formed. The thickeners mentioned above are employed as thickeners.

Pour-on formulations are poured or sprayed on to limited areas of the skin, the active compound penetrating through the skin and acting systemically.

Pour-on formulations are prepared by dissolving, suspending or emulsifying the active compound in suitable solvents or solvent mixtures tolerated by the skin. If appropriate, further auxiliaries, such as colorants, absorption-promoting substances, antioxidants, light stabilizers, adhesives, are added.

Solvents which may be mentioned are: water, alkanols, glycols, polyethylene glycols, polypropylene glycols, glycerol, aromatic alcohols, such as benzyl alcohol, phenylethanol, phenoxyethanol, esters, such as ethyl acetate, butyl acetate, benzyl benzoate, ethers, such as alkylene glycol alkyl ethers, such as dipropylene glycol monomethyl ether, diethylene glycol mono-butyl ether, ketones, such as acetone, methyl ethyl ketone, aromatic and/or aliphatic hydrocarbons, vegetable or synthetic oils, DMF, dimethylacetamide, N-methylpyrrolidone, 2,2-dimethyl4-oxy-methylene-1,3-dioxolane.

Colorants are all the colorants which are approved for use on animals and can be dissolved or suspended.

Absorption-promoting substances are, for example, DMSO, spreading oils, such as isopropyl myristate, dipropylene glycol pelargonate, silicone oils, fatty acid esters, triglycerides, fatty alcohols.

Antioxidants are sulphites or metabisulphites, such as potassium metabisulphite, ascorbic acid, butylhydroxytoluene, butylhydroxyanisole, tocopherol.

Light stabilizers are, for example, novantisole acid.

Adhesives are, for example, cellulose derivatives, starch derivatives, polyacrylates, naturally occurring polymers, such as alginates, gelatin.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing this solution with the solvent of the other phase with the aid of suitable emulsifiers and if appropriate other auxiliaries, such as colorants, absorption-promoting substances, preservatives, antioxidants, light stabilizers, viscosity-increasing substances.

Hydrophobic phases (oils) which may be mentioned are: paraffin oils, silicone oils, naturally occurring plant oils, such as sesame oil, almond oil, castor oil, synthetic triglycerides, such as caprylic/capric acid biglyceride, a triglyceride mixture with plant fatty acids of chain length $C_{8-12}$ or other specially selected naturally occurring fatty acids, partial glyceride mixtures of saturated or unsaturated fatty acids, which may also contain hydroxyl groups, mono- and diglycerides of $C_8/C_{10}$-fatty acids.

Fatty acid esters, such as ethylstearate, di-n-butyryl adipate, hexyl laurate, dipropylene glycol pelargonate, esters of a branched fatty acid of medium chain length with saturated fatty alcohols of chain length $C_{16}$–$C_{18}$, isopropylmyristate, isopropylpalmitate, caprylic/capric acid esters of saturated fatty alcohols of chain length $C_{12}$–$C_{18}$, isopropylstearate, oleyl oleate, decyl oleate, ethyl oleate, ethyl lactate, waxy fatty acid esters, such as synthetic duck aropygeal gland fat, dibutyl phthalate, diisopropyl adipate, ester mixtures related to the latter and others.

Fatty alcohols, such as isotridecyl alcohol, 2-octyldodecanol, cetylstearyl alcohol, oleyl alcohol.

Fatty acids, such as, for example, oleic acid and its mixtures.

Hydrophilic phases which may be mentioned are:
water, alcohols, such as, for example, propylene glycol, glycerol, sorbitol and their mixtures.

Emulsifiers which may be mentioned are: nonionic surfactants, for example polyoxyethylated castor oil, polyoxyethylated sorbitan monooleate, sorbitan monostearate, glycerol monostearate, polyoxyethylstearate, alkylphenol polyglycol ethers;
ampholytic surfactants, such as di-Na N-lauryl-β-iminodipropionate or lecithin;
anionic surfactants, such as Na lauryl sulphate, fatty alcohol ether-sulphates, mono/dialkyl polyglycol ether orthophosphoric acid ester monoethanolamine salt.

Further auxiliaries which may be mentioned are: viscosity-increasing and emulsion-stabilizing substances, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances listed.

Suspensions can be used orally, dermally, or as an injection. They are prepared by suspending the active compound in a carrier liquid, if appropriate with the addition of other auxiliaries, such as wetting agents, colorants, absorption-promoting substances, preservatives, antioxidant light stabilizers.

Carrier liquids, which may be mentioned are all the homogeneous solvents and solvent mixtures.

Wetting agents (dispersing agents) which may be mentioned are the surfactants mentioned above.

Other auxiliaries which may be mentioned are those mentioned above.

Semi-solid formulations can be administered orally or dermally. They differ from the suspensions and emulsions described above only in their higher viscosity.

To prepare solid formulations, the active compound is mixed with suitable carrier substances, if appropriate with the addition of auxiliaries, and the mixture is brought into the desired shape.

Carrier substances which may be mentioned are all the physiologically tolerated solid inert substances. Inorganic or organic substances serve as such inert substances. Inorganic substances are, for example, sodium chloride, carbonates, such as calcium carbonate, bicarbonates, aluminum oxides, silicic acids, aluminas, precipitated or colloidal silicon dioxide, phosphates.

Organic substances are, for example, sugars, cellulose, foodstuffs and feedstuffs, such as milk powder, animal flours, cereal flours and shredded cereals, starches.

Auxiliaries are preservatives, antioxidants, dyestuffs, which have already been listed above.

Other suitable auxiliaries are lubricants and slip agents, such as, for example, magnesium stearate, stearic acid, talc, bentonites, substances which promote disintegration, such as starch or crosslinked polyvinylpyrrolidone, binders, such as, for example, starch, gelatin or linear polyvinylpyrrolidone, and dry binders, such as microcrystalline cellulose.

The active compounds can also be present in the formulations as a mixture with synergists or with other active compounds which act against pathogenic endoparasites. Such active compounds are, for example, L-2,3,5,6-tetrahydro-6-phenylimidazothiazole, benzimidazole-arbamates, praziiquantel, pyrantel, febantel.

Ready-to-use formulations comprise the active compound in concentrations of 10 ppm −20 percent by weight, preferably 0.1–10 percent by weight.

Formulations which are diluted before use comprise the active compound in concentrations of 0.5–90% by weight, preferably 5–50% by weight.

EXAMPLE A

In vivo Nematode Test

*Haemonchus contortus*/sheep

Sheep experimentally infected with *Haemonchus contortus* were treated after the end of the prepatency period of the parasites. The active compounds were administered orally and/or intravenously as pure active compound.

The efficacy is determined by quantitatively counting the worm eggs excreted with the faeces, before and after treatment.

Complete cessation of the excretion of eggs after treatment means that the worms have been expelled or are so severely damaged that they no longer produce any eggs (*Dosis effectiva*).

The active compounds tested and effective dosages (*Dosis effectiva*) can be seen from the table below.

| Active compound Example No. | *Dosis effectiva* in [mg/kg] |
|---|---|
| 7 | 1.0 |
| 13 | 1.0 |
| 17 | 1.0 |
| 40 | 1.0 |
| 52 | 1.0 |
| 88 | 1.0 |

EXAMPLE B

In vivo Nematode Test

*Trichostrongylus colubriformis*/Sheep

Sheep experimentally infected with *Trichostrongylus colubriformis* were treated after the end of the prepatency period of the parasites. The active compounds were administered orally and/or intravenously as pure active compound.

The efficacy is determined by quantitatively counting the worm eggs excreted with the faeces, before and after treatment.

Complete cessation of the excretion of eggs after treatment means that the worms have been expelled or are so severely damaged that they no longer produce any eggs (*Dosis effectiva*).

The active compounds tested and effective dosages (*Dosis effectiva*) can be seen from the table below.

| Active compound Example No. | *Dosis effectiva* in [mg/kg] |
|---|---|
| 13 | 1.0 |
| 17 | 1.0 |
| 40 | 1.0 |

PREPARATION EXAMPLES

6α- and 6β-Hydroxy-7-(p-tolyl)-1,2,4aα,5aα,8aα,8bα-(z̆)-hexahydro-3,4a-dimethyl-6H-pyrrolo[3',4':4,5]furo[3,2-b]pyrid-8(7H)-one

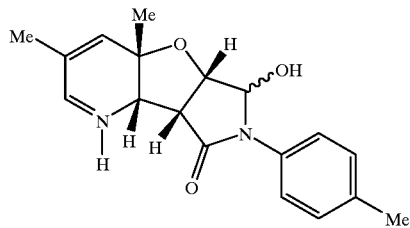

1.6 g (4.9 mmol) of 7-(p-tolyl)-4aα,5aα,8aα,8bα-(±)-tetrahydro-3,4a-dimethyl-6H-pyrrolo[3',4':4,5]furo[3,2-b]pyridine-6,8(7H)-dione are suspended in 50 ml of methanol and, at −5° C., admixed a little at a time with 0.24 g (6.37 mmol) of $NaBH_4$. The mixture is stirred at 0° C. for 1 hour and then at room temperature for approximately 18 hours. The mixture is then acidified (pH 7–8) using 1 N HCl, and the entire reaction solution is concentrated under reduced pressure. The residue that remains is then taken up in chloroform, and the organic phase is extracted repeatedly with water and saturated NaCl solution. The organic phase is separated off, dried over magnesium sulphate and concentrated under reduced pressure. This gives a 6α/6β-hydroxy isomer mixture which can be separated on a silica gel column (silica gel 60-Merck, particle size: 0.04 bis 0.063 mm) using the mobile phase cyclohexane:acetone (2:1).

EXAMPLE 1

6α-Hydroxy-7-(p-tolyl)-1,2,4aα,5aα,8aα,8bα-(±)-hexahydro-3,4a-dimethyl-6H-pyrrolo[3',4':4,5]furo[3,2-b]pyrid-8(7H)-one m.p.: 171° C.

$^1$H NMR (400 MHz, $CDCl_3$, δ): 1.25, 1.73,2.33 (s, 9H, —$CH_3$); 3.19–3.26 (m, 3H, —N—$CH_2$—, —N—CH—); 3.63 (dd, 1H, —CH—CO—); 4.08,4.93 (2d, 2H, —$CH_2$-aryl; J =14.6 Hz); 4.68 (dd, 1H, —O—CH—); 4.78 (d, 1H, —CH—OH); 5.53 (s, 1H, =CH—); 6.1 (brd.s, 1H, —OH); 7.12, 7.14 (2d, 4H, aryl-H, J=8.1 Hz) ppm.

EXAMPLE 2

6β-Hydroxy-7-(p-tolyl)-1,2,4aα,5aα,8aα,8bα-(±)-hexahydro-3,4a-dimethyl-6H-pyrrolo[3',4':4,5]furo[3,2-b]pyrid-8(7H)-one m.p.: 143–144° C.

$^1$H NMR (400 MHz, $CDCl_3$, δ): 1.17, 1.41, 2.31 (s, 9H, —$CH_3$); 3,18 (brd, 2H, —N—$OCH_2$—); 3.25 (d, 1H, —N—CH—); 3.64 (dd, 1H, —CH—CO—); 4.04, 4.65 (2d, 2H, —CH$_2$-aryl; J=14.6 Hz); 4.37 (dd, 1H, —O—CH—); 5.05 (d, 1H, —CH—OH); 5.43 (s, 1H, =CH—); 7.10, 7.23 (2d, 4H, aryl-H, J=8.1 Hz) ppm.

EI-MS m/z (%): 328 (M$^+$, 2); 310 (28); 108 (100).

EXAMPLE 3

6β-Hydroxy-1,2,4aα,5aα,8aα,8bα-(±)-hexahydro-3, 4a,7-trimethyl-6H-pyrrolo[3',4':4,5]furo[3,2-b]pyrid-8(7H)-one

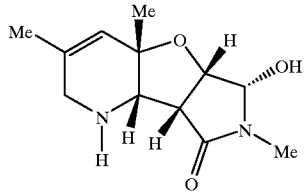

Analogously to Example 1, the 6β-hydroxy isomer is prepared from:

5.00 g (0.020 mol) of 4aα,5aα,8bα-(±)-tetrahydro-3,4a, 7-trimethyl-6H-pyrrolo[3',4':4,5]furo[3,2-b]pyridine6,8 (7H)-dione 0.98 g (0.026 Mol) of NaBH$_4$ 100 ml of methanol This gives 3.2 g (66.9% of theory) of 6β-hydroxy-1,2, 4aα,5aα,8aα,8bα-(±)-hexahydro-3,4a,7-trimethyl-6H-pyrrolo[3',4:4,5]furo[3,2-b]pyrid-8(7H)-one.

m.p.: 158–160° C.

$^{13}$C NMR (150 MHz, CDCl$_3$, δ): 20.5 25.2 (2×—CH$_3$); 51.2 (—CO—CH—); 27.2 —N—CH$_3$); 75.4, 84.9 (1×—O—CH—); 83.9 (HO—CH—N—); 170.8 (1×—N—C=O); 47.7 (1×—NH—CH$_2$—); 59.0 (—NH—CH—); 122.8 (=CH—); 135.0 (=C—Me) ppm.

EI-MS m/z (%): 338 (M$^+$, 3); 108 (100).

EXAMPLE 4

7-Ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one

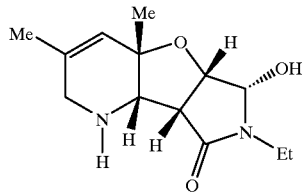

Analogously to Example 3, the 6β-hydroxy isomer is prepared from:

8.00 g (0.034 mol) of 7-ethyl-4aα,5aα,8aα,8bα-(±)-tetrahydro-3,4a-dimethyl-6H-pyrrolo[3',4':4,5]furo[3,2-b]pyridin-6,8(7H)-dione 1.67 g (0.044 mol) of NaBH$_4$ 160 ml of methanol This gives 6.7 g (78.5% of theory) of 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one.

m.p.: 114° C.

EXAMPLE 5

Hydrogen sulphate of 7-ethyl-6β-hydroxy-1,2,4aα, 5aα,8aα,8bα-(±)-hexahydro-3,4a-dimethyl-6H-pyrrolo[3',4':4,5]furo[3,2-b]pyrid-8(7H)-one

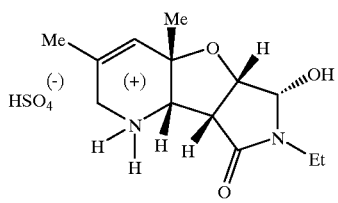

10.0 g (0.04 mmol) of 7-ethyl-6β-hydroxy-1,2,4aα,5aα, 8aα,8bα-(±)-hexahydro-3,4a-dimethyl-6H-pyrrolo[3',4':4, 5]furo[3,2-b]pyrid-8(7H)-one are initially charged in 50 ml of ethanol, admixed with 21 ml of 2M H$_2$SO$_4$ in ethanol (pH2) and stirred at room temperature for 72 hours. The precipitated solid is separated off and washed with ethanol. This gives 8.4 g (60.4% of theory) of 7-ethyl-6β-hydroxy-1,2,4aα,5aα,8aα,8bα-(ž)-hexahydro-3,4a-dimethyl-6H-pyrrolo[3',4':4,5]furo[3,2-b]pyrid-8 (7H)-one H$_2$SO$_4$.

m.p.: 168–170° C. (decomp.)

EXAMPLE 6

7-Ethyl-6α-ethoxy-1,2,4aα,5aα,8aα,8bα-(±)-hexahydro-3,4a-dimethyl-6H-pyrrolo[3',4':4,5]furo[3,2-b]pyrid-8(7H)-one

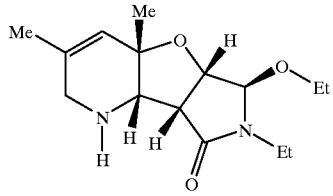

The mother liquor from Example 5 is concentrated and the crude product that remains is chromatographed over a silica gel column (silica gel 60-Merck, particle size: 0.04 to 0.063 mm) and the mobile phase cyclohexane:acetone (2:1). This gives 0.5 g (4.5% of theory) of 7-ethyl-6α-ethoxy-1, 2,4aα,5aα,8aα,8bα-(±)-hexahydro-3,4a-dimethyl-6H-pyrrolo[3',4':4,5]furo[3,2-b]pyrid-8(7H)-one.

$^1$H NMR (400 MHz, CDCl$_3$, ): 1.19, 1.25 (2t, 6H, —CH$_3$); 1.71, 1.88 (2s, 6H, —CH$_3$); 3.17–3.70 (m, 7H; 2×—N—CH$_2$—, —O—CH$_2$, —N—CH—, —O—CH—, —CH—); 4.36 (d, 1H, —O—CH—); 4.85 (s, 1H, —CH—OH); 5.62 (s, 1H, =CH—) ppm.

EI-MS m/z (%): 280 (M+., 16); 251 (30); 108 (100).

EXAMPLE 7

6β-Hydroxy-1,2,3,4,4aα,5aα,8aα,8bα-(±)-
octahydro-3β,4a,7-trimethyl-6H-pyrrolo[3',4':4,5]
furo[3,2-b]pyrid-8(7H)-one

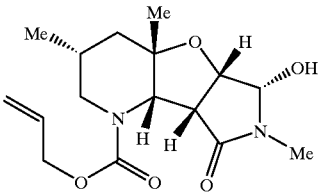

The 6β-hydroxy isomer is prepared analogously to Example 1 from:

6.40 g (0.020 mol) of 1,2,3,4,4aα,5aα,8aα,8bα-(±)-octahydro-3β,4a,7-trimethyl-6H-pyrrolo[3',4':4,5]furo[3,2-b]pyridine-6,8(7H)dione 0.98 g (0.026 mol) of $NaBH_4$ 100 ml of methanol This gives 6.3 g (96.6% of theory) of 6β-hydroxy-1,2,3,4,4aα,5aα,8aα,8bα-(±)-octahydro-3β,4a,7-trimethyl-6H-pyrrolo[3',4':4,5]furo[3,2-b]pyrid-8(7H)-one.

m.p.: 88–89° C.

$^{13}C$ NMR (150 MHz, $CDCl_3$, δ): 20.0, 24.5 (2×—$CH_3$); 23.4 (—CH—); 26.5 (—N—$CH_3$); 73.2, 82.2, 82.9 (3×—O—CH—); 156.3, 169.5 (2×—N—C=O); 40.5, 48.1 (2×—$CH_2$—); 48.8 (—CH—); 62.4 (—N—CH—); 66.1 (—O—$CH_2$—); 117.0 (=$CH_2$); 133.0 (—CH=) ppm.

EI-MS m/z (%): 324 ($M^+$, 8); 239 (12); 221 (100).

EXAMPLE 8

1-Allyloxycarbonyl-7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one

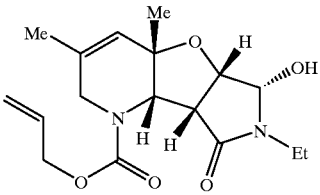

5.0 g (14.2 mmol) of 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one $H_2SO_4$ are suspended in 100 ml of methylene chloride, admixed with 30 ml of water, 5.0 g (39.0 mmol) of N,N-diisopropylethylamine ("Hünig's Base") and stirred at room temperature for 30 minutes. The aqueous phase is separated off and the organic phase is then concentrated under reduced pressure. A solution of 2.8 g (11.0 mmol) of the liberated 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one, 2.7 g (20.8 mmol) of N,N-diisopropylethylamine ("Hünig's Base") and 1.4 g (12.0 mmol) of allyl chloroformate in 50 ml of methylene chloride is then stirred initially at 0° C. for 1 hour and then at room temperature for another 18 hours. The entire reaction solution is then washed repeatedly with water. The organic phase is separated off, dried over magnesium sulphate and then concentrated under reduced pressure, and the crude product that remains is chromatographed over a silica gel column (silica gel 60-Merck, particle size: 0.04 to 0.063 mm) using the mobile phase cyclohexane:acetone (2:1). This gives 2.6 g (70.2% of theory) of l-allyloxycarbonyl-7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one.

$^1H$ NMR (300 MHz, $CDCl_3$, δ): 4.73 (dd, 1H, 5aα-H; $J^1$=7.4 Hz; $J^2$=1.0 Hz); 5.54 (s, 1H, =CH—); 6.11 (d, 1H, NH, J=12.1 Hz) ppm.

EI-MS m/z (%): 336 ($M^+$, 18); 318 (20); 251(45); 233 (100).

APCI-MS-LOOP acidic m/z (%): 337 ($MH^+$, 21); 319 (100).

EXAMPLE 9

1-(N-Benzyloxycarbonyl-N-methyl-glycyl)-7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)one

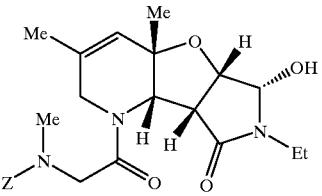

At 0° C., 2.2 g (17.2 mmol) of N,N-diisopropylethylamine (Hünig's Base) and 2.2 g (8.7 mmol) of bis(2-oxo-3-oxazolidinyl)phosphinic chloride (BOP-CI) are added to a solution of 2.2 g (8.7 mmol) of 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one and 1.6 g (7.25 mmol) of N-benzyloxycarbonyl-sarcosine (Z-Sar-OH) in 80 ml of methylene chloride, and the mixture is stirred at 0° C. for 30 minutes and then at room temperature for 18 hours. The reaction solution is shaken twice with water and the organic phase is separated off and, after drying over sodium sulphate, concentrated under reduced pressure. The crude product that remains is chromatographed over a silica gel column (silica gel 60-Merck, particle size: 0.04 to 0.063 mm) using the mobile phase cyclohexane:acetone (2:1). This gives 2.3 g (57.8% of theory) of 1-(N-benzyloxycarbonyl-N-methyl-glycyl)-7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one.

EI-MS m/z (%): 457 (M⁺, 19), 251 (80), 233 (85), 91 (100).

EXAMPLE 10

1-(N-Methylaminocarbonyl)-7-ethyl-6β-hydroxy-1, 2,4aα,5aα,8aα,8bα-(±)-hexahydro-3,4a-dimethyl-6H-pyrrolo[3',4':4,5]furo[3,2-b]pyrid-8(7H)-one

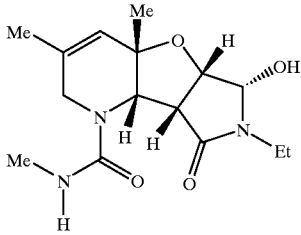

2.2 g (8.7 mmol) of 7-ethyl-6β-hydroxy-1,2,4aα,5aα, 8aα,8bα-(±)-hexahydro-3,4a-dimethyl-6H-pyrrolo[3',4':4, 5]furo[3,2-b]pyrid-8(7H)-one and 0.6 g (8.7 mmol) of methyl isocyanate in 20 ml of toluene are stirred at reflux temperature for 1 hour. After cooling, the precipitated solid is separated off and stirred with diethyl ether. This gives 2.0 g (74.3% of theory) of I-(N-methylaminocarbonyl)-7-ethyl-6β-hydroxy-1,2,4aα,5aα,8aα,8bα-(ž)-hexahydro-3,4a-dimethyl-6H-pyrrolo[3',4':4,5]furo[3,2-b]pyrid-8(7H)-one.

¹H NMR (300 MHz, CDCl₃, δ): 4.61 (dd, 1H, 5aα-H; J¹=7.4 Hz; J²=1.0 Hz); 5.06 (d, 1H, 6β-H, J=7.4 Hz); 5.32 (s, 1H, =CH—) ppm.

¹³C NMR (150 MHz, CDCl₃, δ): 13.1, 20.0, 26.2, 27.6 (4×—CH₃); 35.1 (1×—N—CH₂—); 158.3 (1×—NH—C=O); 170.3 (1×—N—C=O); 46.3 (1×—CH—); 73.9 (1×—O—CH—); 81.7 (1×HO—CH—N—); 78.2 (1×C—Me); 58.8 (1×—N—CH—); 45.6 (1×—N—CH₂—); 129.8 (1×=C—Me); 125.6 (1×—CH=) ppm.

EI-MS m/z (%): 309 (M⁺, 8), 234 (22), 108 (100).

EXAMPLE 11

1-Allyloxycarbonyl-6α-ethoxy-1,2,4aα,5aα,8aα, 8bα-(±)hexahydro-3,4a,7-trimethyl-6H-pyrrolo[3', 4':4,5]furo[3,2-b]pyrid-8(7H)-one

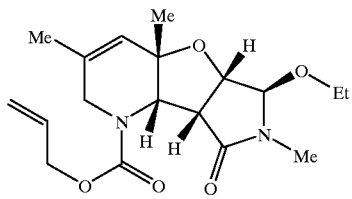

1.6 g (5.0 mmol) of 1-allyloxycarbonyl-6β-hydroxy-1,2, 4aα,5aα,8aα,8bα-(±)-hexahydro-3,4a,7-trimethyl-6H-pyrrolo[3',4':4,5]furo[3,2-b]pyrid-8(7H)-one are dissolved in 50 ml of ethanol and admixed with 2 ml of 2M H₂SO₄, and the mixture is stirred at room temperature for 48 hours. The pH is subsequently adjusted to 7 using saturated NaHCO₃ solution, and the entire reaction solution is concentrated under reduced pressure. The residue that remains is then taken up in methylene chloride, and the organic phase is repeatedly extracted with water. The organic phase is separated off, dried over magnesium sulphate and concentrated under reduced pressure, and the crude product that remains is chromatographed over a silica gel column (silica gel 60-Merck, particle size: 0.04 to 0.063 mm) using the mobile phase cyclohexane:acetone (4:1). This gives 0.8 g (45.7% of theory) of 1-allyloxycarhonyl-6α-ethoxy-1,2, 4aα,5aα,8aα,8bα-(±)-hexahydro-3,4a,7-trimethyl-6H-pyrrolo[3',4':4,5]furo[3,2-b]pyrid-8(7H)-one.

m.p.: 68–69° C.

¹H NMR (300 MHz, CDCl₃, δ): 4.43 (d, 1H, 5aβ-H) ppm.

EXAMPLE 12

1-Allyloxycarbonyl-6α-ethoxy-1,2,3,4,4aα,5aα,8aα, 8bα-(±)-octahydro-3β,4a,7-trimethyl-6H-pyrrolo[3', 4':4,5]furo[3,2-b]pyrid-8(7H)-one

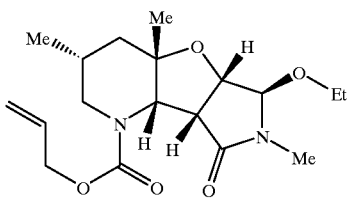

The 6α-ethoxy isomer is prepared analogously to Example 7 from:

2.0 g (6.0 mmol) of 1-allyloxycarbonyl-6β-hydroxy-1,2, 3,4,4aα,5aα,8aα,8bα-(±)-octahydro-3β,4a,7-trimethyl-6H-pyrrolo[3',4':4,5]furo[3,2-b]pyrid-8(7H)-one 0.5 ml of 2M H₂SO₄

30 ml of ethanol

This gives 1.0 g (47.3% of theory) of 1-allyloxycarbonyl-6α-ethoxy-1,2,3,4,4aα,5aα,8aα,8bα-(±)-octahydro-3β,4a, 7-trimethyl-6H-pyrrolo[3',4':4,5]furo[3,2-b]pyrid-8(7H)-one.

m.p.: oil

¹³C NMR (150 MHz, CHCl₃, δ): 48.1, 39.2, 40.4 (3×—CH₂—); 62.7, 62.9, 66.0, 66.1 (4×—O—CH₂—); 15.0; 15.8, 20.2, 26.7, 27.1 (5×—CH₃); 23.3, 47.3, 47.4 (3×—CH—); 61.3 (1×—N—CH—); 77.7, 78.0, 92.6, 92.8 (4×—O—CH—); 27.5 (1×—N—CH₃); 156.1, 156.6, 171.3, 171.4 (4×—N—C=O); 133.0, 133.3 (2×—CH=); 116.9, 117.0 (2×=CH₂) ppm. (E/Z isomer mixture)

EI-MS m/z (%): 352 (M⁺, 8); 267 (100); 108 (40); 41(46).

EXAMPLE 13

1-Allyloxycarbonyl-6α-hydroxy-1,2,4aα,5aα,8aα, 8bα-(±)-hexahydro-3,4a,7-trimethyl-6H-pyrrolo[3', 4':4,5]furo[3,2-b]pyrid-8(7H)-one

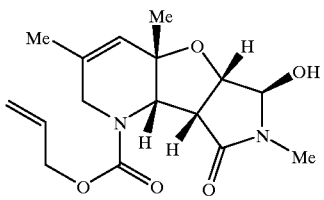

1.1 g (3.0 mmol) of 1-allyloxycarbonyl-6β-hydroxy-1,2, 4aα,5aα,8aα,8bα-(±)-hexahydro-3,4a,7-trimethyl-6H-pyrrolo[3',4':4,5]furo[3,2-b]pyrid-8(7H)-one are dissolved in 75 ml of ethanol, admixed with 6.5 ml of 4N NaOH and stirred at room temperature for 18 hours. The mixture is subsequently adjusted to pH7 using 10% strength HCl, and the entire reaction solution is concentrated under reduced pressure. The residue that remains is then taken up in methylene chloride and the organic phase is extracted repeatedly with water. The organic phase is separated off, dried over magnesium sulphate and concentrated under reduced pressure, and the crude product that remains is chromatographed over a silica gel column (silica gel 60-Merck, particle size: 0.04 to 0.063 mm) using the mobile phase cyclohexane:acetone (2:1). This gives 0.65 g (67.4% of theory) of 1-allyloxycarbonyl-6α-hydroxy-1,2,4aα,5aα,8aα,8bα-(±)-hexahydro-3,4a,7-trimethyl-6H-pyrrolo[3',4':4,5]furo[3,2-b]pyrid-8(7H)-one.

m.p.: 102° C.

$^1$H NMR (300 MHz, CDCl$_3$, δ): 5.30 (s, 1H, 6β-H) ppm.

$^{13}$C NMR (150 MHz, CHCl$_3$, δ): 45.8, 46.0 (2×—CH$_2$—); 66.4, 66.5 (2×—O—CH$_2$—); 20.0, 20.1, 25.9, 26.0 (4×—CH$_3$); 45.3, 45.9 (2×—CH—); 60.6, 60.9 (2×—N—CH—); 77.7, 77.9, 82.0, 82.1, 90.2, 90.3 (6×—O—CH—); 26.9 (1×—N—CH$_3$); 131.1, 130.4 (2×Me—C=); 124.2, 124.7 (2×=CH—), 172.0, 172.3, 155.6, 156.2 (4×—N—C=O); 132.6, 132.8 (2×—CH=); 117.5 (1×=CH$_2$) ppm (E/Z isomer mixture).

EXAMPLE 14

6β-Acetoxy-1-allyloxycarbonyl-7-ethyl-1,2,4aα,5aα,8aα,8bα-(±)-hexahydro-3,4a-dimethyl-6H-pyrrolo[3,4':4,5]furo[3,2-b]pyrid-8(7H)-one

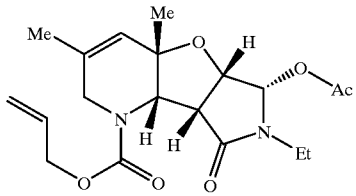

4.4 g (13.0 mmol) of 1-allyloxycarbonyl-6β-hydroxy-7-ethyl-1,2,4aα,5aα,8aα,8bα-(±)-hexahydro-3,4a-dimethyl-6H-pyrrolo[3',4':4,5]furo[3,2-b]pyrid-8(7H)-one are dissolved in 50 ml of methylene chloride and, at 0° C., admixed with 1.4 g (13.5 mmol) of triethylamine and 0.16 g (1.3 mmol) of 4-(N,N-dimethylamino)-pyridine. 2.0 g (19.5 mmol) of acetic anhydride are then added dropwise and the mixture is stirred at 0–5° C. for 1 hour and at room temperature for a further 20 hours. The mixture is subsequently washed with 10% strength HCl, saturated NaHCO$_3$ solution and water. The organic phase is separated off and dried over magnesium sulphate and then concentrated under reduced pressure, and the crude product that remains is chromatographed over a silica gel column (silica gel 60-Merck, particle size: 0.04 to 0.063 mm) using the mobile phase cyclohexane:acetone (4:1). This gives 3.4 g (69.9% of theory) of 6β-acetoxy-1-allyloxycarbonyl-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

$^1$H NMR (300 MHz, CDCl$_3$, δ): 5.85 (d, 1H, 6α-H) ppm.

EI-MS mz (%): 378 (M$^+$, 12), 318 (25), 293 (19), 233 (100), 148 (60).

EXAMPLE 15

1-Allyloxycarbonyl-6β-cyclopropylcarbonyloxy-7-ethyl-1,2,4aα,5aα,8aα,8bα-(±)-hexahydro-3,4a-dimethyl-6H-pyrrolo[3',4':4,5]furo[3,2-b]pyrid-8(7H)-one

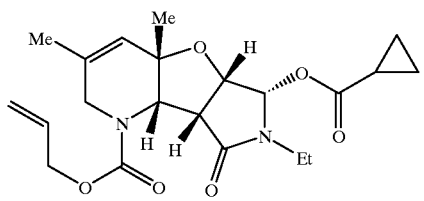

The 6β-cyclopropylcarbonyloxy isomer is prepared analogously to Example 14 from:

1.20 g (3.6 mmol of 1-allyloxycarbonyl-6β-hydroxy-7-ethyl-1,2,4aα,5aα,8aα,8bα-(±)-hexahydro-3,4a,7-trimethyl-6H-pyrrolo[3',4':4,5]furo[3,2-b]pyrid-8(7H)-one 0.37 g (3.7 mmol) of triethylamine 0.56 g (5.4 mmol) of cyclopropanecarbonyl chloride about 0.04 g of 4-(N,N-dimethylamino)-pyridine 20 ml of methylene chloride This gives 0.25 g (17.1% of theory) of 1-allyloxycarbonyl-6β-cyclopropylcarbonyloxy-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

EI-MS m/z (%): 404 (M$^{+\cdot}$, 7), 319 (30), 108 (82).

EXAMPLE 16

6β-(N-Benzyloxycarbonyl-N-methyl-leucinyloxy)-7-ethyl-1,2,4aα,5aα,8aα,8bα-(±)-hexahydro-3,4a-dimethyl-6H-pyrrolo[3',4':4,5]furo[3,2-b]pyrid-8(7H)-one

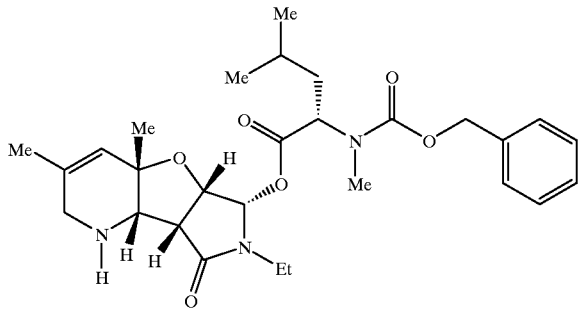

The 6β-O-acyl derivative is prepared analogously to Example 9 from:

2.2 g (8.70 mmol) of 7-ethyl-6β-hydroxy-1,2,4aα,5aα,8aα,8bα-(±)-hexahydro-3,4a-dimethyl-6H-pyrrolo[3',4':4,5]furo[3,2-b]pyrid-8(7H)-one 1.9 g (7.25 mmol) of N-benzyloxycarbonyl-N-methyl-leucine (Z-MeLeu-OH)

2.2 g (17.2 mmol) of N,N-diisopropylethylamine (Hünig's Base)

2.2 g (8.70 mmol) of bis(2-oxo-3-oxazolidinyl)-phosphinic chloride (BOP-Cl)

80 ml of methylene chloride

After work-up, the crude product that remains is chromatographed over a silica gel column (silica gel 60-Merck, particle size: 0.04 to 0.063 mm) using the mobile phase cyclohexane:acetone (2:1). This gives 150 mg (3.4% of theory) of 6β-(N-benzyloxycarbonyl-N-methyl-leucinyloxy)-7-ethyl-1,2,4aα,5aα,8aα,8bα-(±)-hexahydro-3,4a-dimethyl6H-pyrrolo[3',4':4,5]furo[3,2-b]pyrid-8(7H)-one as a mixture of diastereomers.

m.p.: oil $^{13}$C NMR (150 MHz, CDCl$_3$, δ): 12.8, 12.9, 21.3, 23.3, 24.4, 24.5, (4×—$\underline{C}$H$_3$); 36.0, 36.7 (1×—N—$\underline{C}$H$_2$—); 30.1 (1×—N—$\underline{C}$H$_3$); 24.2, 24.4 (1×—$\underline{C}$H—); 36.2, 37.5 (1×—$\underline{C}$H$_2$—); 49.0 (1×—NH—$\underline{C}$H$_2$—); 50.1, 50.3 (1×—CO—$\underline{C}$H—); 56.7 (1×—CO—$\underline{C}$H—); 60.7, 60.8 (1×—NH—$\underline{C}$H—); 67.4, 67.5 (1×—O—$\underline{C}$Hr$_2$—); 72.8, 73.0 (1×—O—$\underline{C}$H—); 83.6, 84.1 (1×CO—O—$\underline{C}$H—); 83.5, 83.6 (1×—$\underline{C}$—Me); 122.8, 123.3 (1×=$\underline{C}$—H); 136.3, 136.5 (1×=$\underline{C}$—Me); 127.7, 17.9, 128.4, 139.1, 140.1 (4×aryl —$\underline{C}$H=) 156.0, 156.7, 170.9 (1×—N—$\underline{C}$=O); ppm.

EI-MS m/z (%): 513 (M$^+$, 1), 234 (18), 108 (100).

EXAMPLE 17

1-Allyloxycarbonyl-6β-allyloxycarbonyloxy-1,2,4aα,5aα,8aα,8bα-(±)-hexahydro-3,4a,7-trimethyl-6H-pyrrolo[3',4':4,5]furo[3,2-b]pyrid-8(7H)-one

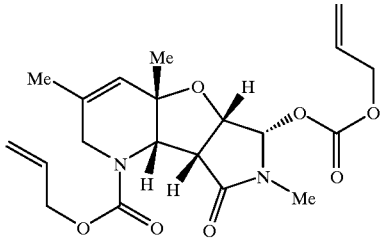

At 0° C., 12.9 g (0.10 mol) of N,N-diisopropylethylamine ("Hünig's base") and 5.7 g (0.048 mol) of allyl chloroformate are added dropwise to a solution of 5.0 g (0.02 mol) of 6β-hydroxy-1,2,4aα,5aα,8aα,8bα-(±)-hexa-hydro-3,4a,7-trimethyl-6H-pyrrolo[3',4':4,5]furo[3,2-b]pyrid-8(7H)-one in 150 ml of methylene chloride, and the mixture is stirred at room temperature for 18 hours. The mixture is subsequently washed twice with water. The organic phase is separated off and dried over magnesium sulphate and then concentrated under reduced pressure, and the crude product that remains is chromatographed over a silica gel column (silica gel 60-Merck, particle size: 0.04 to 0.063 mm) using the mobile phase cyclohexane:acetone (2:1). This gives 1.4 g (17.2% of theory) of 1-allyloxycarbonyl-6β-allyloxycarbonyloxy-1,2,4aα,5aα,8aα,8bα-(±)-hexahydro-3,4a,7-trimethyl-6H-pyrrolo[3',4':4,5]furo[3,2-b]pyrid-8(7H)-one.

$^1$H NMR (300 MHz, CDCl$_3$, δ): 5.67 (d, 1H, 6a-H; J=5.6 Hz) ppm.

EI-MS m/z (%/): 322 (M$^+$, 38), 237 (88), 219 (100).

EXAMPLE 18

1-Acetyl-6β-acetoxy-7-ethyl-1,2,4aα,5aα,8aα,8ba-(+)-hexahydro-3,4a-dimethyl-6H-pyrrolo[3',4':4,5]furo[3,2-b]pyrid-8(7H)one

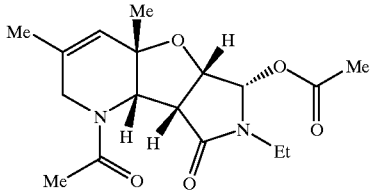

The 6β-acetoxy isomer is prepared analogously to Example 14 from:

1.20 g (3.6 mmol) of 6β-hydroxy-7-ethyl-1,2,4aα,5aα,8aα,8bα-(±)-hexahydro-3,4a-dimethyl-6H-pyrrolo[3',4':4,5]furo[3,2-b]pyrid-8(7H)-one 1.80 g (17.9 mmol) of triethylamine 2.04 g (20.0 mmol) of acetic anhydride about 0.22 g of 4-(N,N-dimethylamino)-pyridine 30 ml of methylene chloride This gives 0.5 g (38.8% of theory) of 1-acetyl-6β-acetoxy-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

$^1$H NMR (300 MHz, CDCl$_3$, δ): 5.85 (d, 1H, 6α-H; J=5.6 Hz) ppm.

EI-MS m/z (%): 336 (M$^+$, 21), 233 (42), 108 (100).

EXAMPLE 19

6α-Allyl-1-allyloxycarbonyl-1,2,4aα,5aα,8aα,8ba-(+)-hexahydro-3,4a,7-trimethyl-6H-pyrrolo[3',4':4,5]furo[3,2-b]pyrid-8(7H)-one

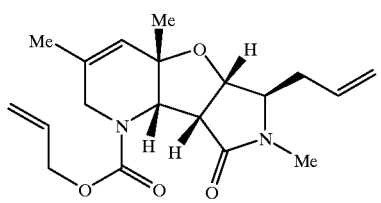

1.2 g (3.0 mmol) of 1-allyloxycarbonyl-6α-ethoxy-1,2,4aα,5aα,8aα,8bα-(±)-hexahydro-3,4a,7-trimethyl-6H-pyrrolo[3',4':4,5]furo[3,2-b]pyrid-8(7H)-one are dissolved in 30 ml of methylene chloride and, at −70° C., admixed successively with 0.68 g (6.0 mmol) of allyltrimethylsilane and 0.85 g (6.0 mmol) of BF$_3$ Et$_2$O (argon atmosphere). The mixture is subsequently stirred at −70° C. for another 5 minutes and then at room temperature for another 1.5 to 2 hours. The mixture is then washed with saturated NaHCO$_3$ solution and water. The organic phase is separated off and dried over magnesium sulphate and then concentrated under reduced pressure, and the crude product that remains is chromatographed over a silica gel column (silica gel 60-Merck, particle size: 0.04 to 0.063 mm) using the mobile phase cyclohexane:acetone (4:1). This gives 0.42 g (40.4% of theory) of 6α-allyl-1-allyloxycarbonyl-1,2,4aα,5aα,8aα,8bα-(±)-hexahydro-3,4a,7-trimethyl-6H-pyrrolo[3',4':4,5]furo[3,2-b]pyrid-8(7H)-one.

$^1$H NMR (300 MHz, CDCl$_3$, δ): 4.42 (dd, 1H, 5aα-H; J$^1$=7.4 Hz; J$^2$=1.0 Hz) ppm.

EI-MS m/z (%): 346 (M$^+$, 42), 261(100).

EXAMPLE 20

6α-Allyl-1-allyloxycarbonyl-7-ethyl-1,2,4aα,5aα,8aα,8bα-(±)-hexahydro-3,4a-dimethyl-6H-pyrrolo[3',4':4,5]furo[3,2-b]pyrid-8(7H)-one

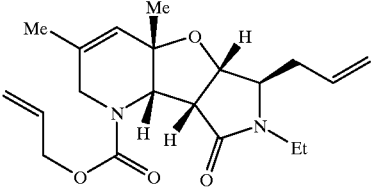

The 6α-allyl isomer is prepared analogously to Example 19 from:

1.90 g (5.00 mmol) of 1-allyloxycarbonyl-60-hydroxy-7-ethyl-1,2,4aα,5aα,8aα,8bα-(±)-hexahydro-3β,4',7-trimethyl-6H-pyrrolo[3',4':4,5]furo[3,2-b]pyrid-8(7H)-one 1.10 g (10.0 mmol) of allyltrimethylsilane 1.42 g (10.0 mmol) of BF$_3$.Et$_2$O 50 ml of methylene chloride This gives 0.75 g (41.6% of theory) of 6α-allyl-1-allyloxycarbonyl-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

$^1$H NMR (300 MHz, CDCl$_3$, δ): 4.42 (dd, 1H, 5aα-H; J$^1$=7.4 Hz; J$^2$=1.0 Hz) ppm.

EI-MS m/z (%): 360 (M$^+$, 38); 275 (100); 148 (62); 41 (54).

EXAMPLE 21

6α-Allyl-1-allyloxycarbonyl-1,2,3,4,4aα,5aα,8aα,8bα-(±)-octahydro-3p,4a,7-trimethyl-6H-pyrrolo[3',4':4,5]furo[3,2-b]pyrid-8(7H)-one

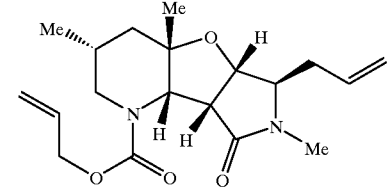

The 6α-allyl isomer is prepared analogously to Example 19 from:

0.80 g (2.3 mmol) of 1-allyloxycarbonyl-6α-ethoxy-1,2,3,4,4aα,5aα,8aα,8bα-(±)-octahydro-3β,4a,7-trimethyl-6H-pyrrolo[3',4':4,5]furo[3,2-b]pyrid-8(7H)-one 1.07 g (4.6 mmol) of allyltrimethylsilane 0.66 g (4.6 mmol) of BF$_3$.Et$_2$O 20 ml of methylene chloride This gives 0.3 g (33.7% of theory) of 6α-allyl-1-allyloxycarbonyl-1,2,3,4,4aα,5aα,8aα,8bα-(±)-octahydro-3β,4a,7-trimethyl-6H-pyrrolo[3',4':4,5]furo[3,2-b]pyrid-8 (7H)-one.

$^1$H NMR (400 MHz, CHCl$_3$, δ): 4.28 (dd, 1H, 5aα-H; J=5.5 Hz).

EI-MS m/z (%): 348 (M$^+$, 9); 263 (100); 138 (12); 108 (62); 41 (54).

EXAMPLE 22

6α-Benzoylmethyl-1-allyloxycarbonyl-7-ethyl-1,2,4aα,5aα,8aα,8bα-(±)-hexahydro-3,4a-dimethyl-6H-pyrrolo[3',4':4,5]furo[3,2-b]pyrid-8(7H)-one

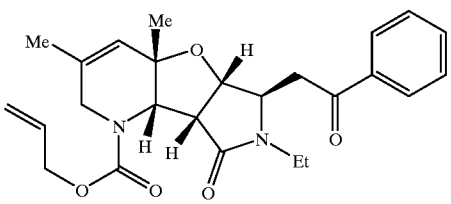

The 6α-benzoylmethyl isomer is prepared analogously to Example 19 from:

2.00 g (5.50 mmol) of n-allyloxycarbonyl-6α-ethoxy-7-ethyl-1,2,4aα,5aα,8aα,8bα-(±)-hexahydro-3,4a,7-dimethyl-6H-pyrrolo[3',4':4,5]furo[3,2-b]pyrid-8(7H)-one 2.10 g (11.0 mmol) of 1-phenyltrimethylsiloxyethylene 1.60 g (11.0 mmol) of $BF_3 \cdot Et_2O$ 50 ml of methylene chloride This gives 0.5 g (21.4% of theory) of 6α-benzoylmethyl-1-allyloxycarbonyl-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

EI-MS m/z (%): 338 ($M^+$, 38); 353 (75); 105 (100).

EXAMPLE 23

1-Allyloxycarbonyl-6α-cyano-7-ethyl-1,2,4aα,5aα,8aα,8bα-(±)-hexahydro-3,4a-dimethyl-6H-pyrrolo[3',4':4,5]furo[3,2-b]pyrid-8(7H)-one

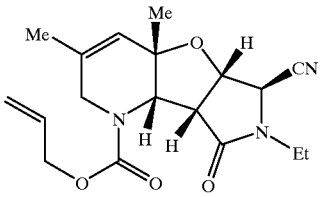

The 6α-cyano isomer is prepared analogously to Example 19 from:

1.20 g (3.0 mmol) of 1-allyloxycarbonyl-6α-ethoxy-7-ethyl-1,2,4aα,5aα,8aα,8bα-(±)-hexahydro-3,4a,dimethyl-6H-pyrrolo[3',4':4,5]furo[3,2-b]pyrid-8(7H)-one 0.59 g (6.0 mmol) of trimethylsilyl cyanide 0.85 g (6.0 mmol) of $BF_3 \cdot Et_2O$ 30 ml of methylene chloride This gives 0.3 g (31.2% of theory) of 1-allyloxycarbonyl-6α-cyano-7-ethyl-1,2,4aα,5aα,8aα,8bα-(±)-hexahydro-3,4a-dimethyl-6H-pyrrolo[3',4':4,5]furo[3,2-b]pyrid-8(7H)-one.

$^1H$ NMR (300 MHz, $CDCl_3$, δ): 4.27 (s, 1H, 6β-H); 4.90 (d, 1H, 5aα-H, J=7.4 Hz) ppm.

$^{13}C$ NMR (150 MHz, $CDCl_3$, δ): 11.6, 11.7, 20.2, 20.3, 26.0, 26.1 (6×—$CH_3$); 36.2 (1×—CO—N—$CH_2$—); 155.3, 156.0, 170.3, 170.6 (4×—N—C═O); 45.3, 46.0 (2×—CH—CO—); 45.8, 46.0 (2×—N—$CH_2$—), 55.5, 60.3, 60.6 (2×—N—CH—); 66.4, 66.5 (2×—O—$CH_2$—); 76.8, 78.6, 78.8 (3×—O—CH—); 116.0 (1×—CN); 117.5; 117.7 (2×═$CH_2$); 123.7, 124.2 (2×—CH═); 131.4, 131.9 (2×Me—C═); 132.6; 132.7 (2×═CH—$CH_2$—) ppm (E/Z-isomer mixture).

EI-MS m/z (%): 345 ($M^+$, 12); 260 (100); 124 (18); 41 (15).

EXAMPLE 24

1-Allyloxycarbonyl-6α-(fur-2-yl)-1,2,4aα,5aα,8aα,8bα-(±)-hexahydro-3,4a,7-trimethyl-6H-pyrrolo[3',4':4,5]furo[3,2-b]pyrid-8(7H)-one

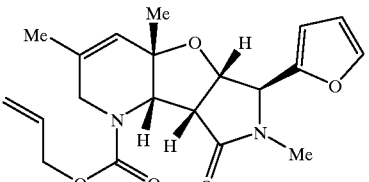

In the presence of 0.74 g (3.9 mmol) of para-toluenesulphonic acid and 5 ml of furan, 1.3 g (3.9 mmol) of 1-allyloxycarbonyl-6α-cyano-1,2,4aα,5aα,8aα,8bα-(±)-hexahydro-3,4a,7-trimethyl-6H-pyrrolo[3',4':4,5]furo[3,2-b]pyrid-8(7H)-one are stirred at reflux temperature for 24 hours. After cooling, the mixture is admixed with sodium bicarbonate solution and the organic phase is separated off and concentrated under reduced pressure. The crude product that remains is chromatographed over a silica gel column (silica gel 60-Merck, particle size: 0.04 to 0.063 mm) using the mobile phase cyclohexane:acetone (6:1). This gives 0.7 g (48.3% of theory) of 1-allyloxycarbonyl-6α-(fur-2-yl)-1,2,4aα,5aα,8aα,8bα-(±)-hexahydro-3,4a,7-trimethyl-6H-pyrrolo[3',4':4,5]furo[3,2-b]pyrid-8(7H)-one.

$^1H$ NMR (300 MHz, $CDCl_3$, δ): 4.42 (s, 1H, 6β-H); 4.64 (d, 1H, 5aa-H, J=7.4 Hz); 6.23, 6.32, 7.36 (3m, 3H, furyl-H) ppm.

EI-MS m/z (%): 345 ($M^+$, 12); 260 (100); 124 (18); 41 (15).

Analogously to the processes, it is possible to prepare the compounds of the general formulae (I-1) and (I-2) listed in Tables 27 and 28 below.

TABLE 27
Examples of compounds of the formula (I-1)
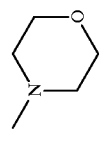
(I-1)
| Ex. No. | $R^1$ | $R^2$ | $R^3$ | $R^4$ | A | B | Physical data* |
|---|---|---|---|---|---|---|---|
| 25 | —H | —Me | 4aα-Me | 2,6-Cl$_2$-Benzyl | 6α-/6β-OH | —H | 282 (M$^+$, 87) |
| 26 | —H | —Me | 4aα-Me | 4-Cl,3-CF$_3$-Benzyl | 6β-OH | —H | m.p.: 130–131° C. |
| 27 | —H | —Me | 4aα-Me | 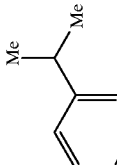 | 6β-OH | —H | 4.33(d, 1H, 6α-H); 4.66 (dd, 1H, 5aα-H) |
| 28 | —H | —Me | 4aα-Me | 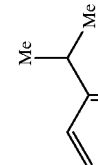 | 6β-OH | —H | m.p.: 130–131° C. |
| 29 | —H | —Me | 4aα-Me |  | 6α-OH | —H | m.p.: 159–160° C. |
| 30 | —H | —Me | 4aα-Me | 2,6-Cl$_2$-Phenyl | 6β-OH | —H | m.p.: 200–204° C. |
| 31 | —H | —Me | 4aα-Me |  | 6β-OH | —H | m.p.: 180–182° C. |

TABLE 27-continued

Examples of compounds of the formula (I-1)

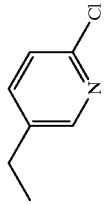

| Ex. No. | R¹ | R² | R³ | R⁴ | A | B | Physical data* |
|---|---|---|---|---|---|---|---|
| 32 | —H | -Me | 4aα-Me | 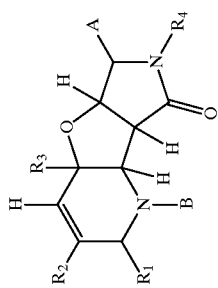 | 6α-OH | —H | m.p.: 185–186° C. |
| 33 | —H | -Me | 4aα-Me | 4-MeO-Benzyl | 6β-OH | —H | m.p.: 113–114° C. |
| 34 | —H | -Me | 4aα-Me | 4-Cl-Benzyl | 6β-OH | —H | m.p.: 153–154° C. |
| 35 | —H | -Me | 4aα-Me | 4-Cl-Benzyl | 6α-OH | —H | m.p.: 175° C. decomp. |
| 36 | —H | -Me | 4aα-Me | -Me | 6β-OH | -Me | m.p.: 80–82° C. |
| 37 | —H | -Me | 4aα-Me | -Et | 6β-OH | —H.HBr | 45.8 (CH₂—NH₂⁺) |
| 38 | —H | -Me | 4aα-Me | -Et | 6β-OH | —H.HI | 5.93 (m,1H,CH—Cl) |
| 39 | —H | -Me | 4aα-Me | -Me | 6β-OH | —CO—O—CHCl-Me | |
| 40 | —H | -Me | 4aα-Me | -Me | 6β-OH | —CO—O-Allyl | m.p.: 103–105° C. |
| 41 | —H | -Me | 4aα-Me | -Me | 6α-O-Me | —CO—O-Allyl | 336 (M⁺,25) |
| 42 | —H | -Me | 4aα-Me | -Me | 6α-O-iPr | —CO—O-Allyl | m.p.: 153–154° C. |
| 43 | —H | -Me | 4aα-Me | -Et | 6α-O-Et | —CO—O-Allyl | m.p.: 68–69° C. |
| 44 | —H | -Me | 4aα-Me | -Me | 6α-O-Allyl | —CO—O-Allyl | m.p.: 175° C. decomp. |
| 45 | —H | -Me | 4aα-Me | -Me | 6α-CN | —CO—O-Allyl | 331 (M⁺, 12) |
| 46 | —H | -Me | 4aα-Me | -Et | 6α- (cyclohexanone) | —CO—O-Allyl | 417 (MH⁺, 100) |
| 47 | —H | -Me | 4aα-Me | -Et | 6β-OH | —CS—NH-Et | 339 (M⁺, 35) |
| 48 | —H | -Me | 4aα-Me | -Et | 6α-O—Ac | —Ac | 336 (M⁺, 23) |
| 49 | —H | -Me | 4aα-Me | -Et | 6α-O-Me | —CO—O-Allyl | 350 (M⁺, 7) |
| 50 | —H | -Me | 4aα-Me | -Et | 6β-OH | —Z | 386 (M⁺, 8) |
| 51 | —H | -Me | 4aα-Me | -Et | 6β-OH | —CS—NH—Cpm | m.p.: 80–81° C. |
| 52 | —H | -Me | 4aα-Me | -Et | 6α-OH | —CS—NH—Cpm | 365 (M⁺, 65) |

TABLE 27-continued
Examples of compounds of the formula (I-1)
(I-1)
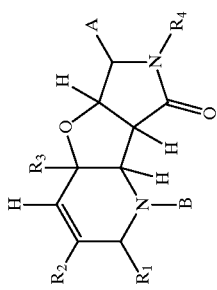
| Ex. No. | $R^1$ | $R^2$ | $R^3$ | $R^4$ | A | B | Physical data* |
|---|---|---|---|---|---|---|---|
| 53 | —H | -Me | 4aα-Me | -Et | 6β-OH | CO—Fur-2-yl | 346 (M+, 42) |
| 54 | —H | -Me | 4aα-Me | -Et | 6α-Fur-2-yl | —CO—O-Allyl | 386 (M+, 50) |
| 55 | —H | -Me | 4aα-Me | -Et | 6α-Thien-2-yl | —CO—O-Allyl | 350 (M+, 28) |
| 56 | —H | -Me | 4aα-Me | -Et | 6β-OH | —CO—O— CH₂—Pnp | 431 (M+, 12) |
| 57 | —H | -Me | 4aα-Me | -Et | 6β-OH | —CO—O-Me | m.p.: 130–32° C. |
| 58 | —H | -Me | 4aα-Me | -Et | 6β-OH | —CO—O-Pnp | m.p.: 72–75° C. |
| 59 | —H | -Me | 4aα-Me | -Me | 6β- [thiazolidine-CO₂Me, N-Boc, S] | —CO—O-Allyl | 537 (M+, 1) |
| 60 | —H | -Me | 4aα-Me | -Me | 6β- [pyrrolidine-CO₂Me, N-Z, S] | —H | 483 (M+, 16) |

TABLE 27-continued

Examples of compounds of the formula (I-1)

(I-1)

| Ex. No. | R¹ | R² | R³ | R⁴ | A | B | Physical data* |
|---|---|---|---|---|---|---|---|
| 61 | —H | -Me | 4α-Me | -Me | 6β- methyl thiazolidine-[S]-carboxylate, N-Boc | —H | m.p.: 90–94° C. |
| 62 | —H | -Me | 4α-Me | -Me | 6β- methyl 4-OBn pyrrolidine-[S]-carboxylate, N-Boc | —H | m.p.: 70–73° C. |
| 63 | —H | -Me | 4α-Me | -Me | 6β- methyl 4-OH pyrrolidine-[S]-carboxylate, N-Boc | —H | 465 (M⁺, 8) 365 (56) |

TABLE 27-continued

Examples of compounds of the formula (I-1)

(I-1)

| Ex. No. | R$^1$ | R$^2$ | R$^3$ | R$^4$ | A | B | Physical data* |
|---|---|---|---|---|---|---|---|
| 64 | —H | -Me | 4aα-Me | -Me | 6β- (methyl pyrrolidine with O·tBu, [S], N-Z) | —H | m.p.: 74–76° C. |
| 65 | —H | -Me | 4aα-Me | -Me | 6β- (tetrahydroisoquinoline with N-Boc, [S], methyl ester) | —H | m.p.: 91–95° C. |
| 66 | —H | -Me | 4aα-Me | —CH$_2$—CH$_2$—CH=CH$_2$ | 6β-OH | —H | m.p.: 102–104° C. |
| 67 | —H | -Me | 4aα-Me | CH$_3$ (2-methylpent-1-enyl) | 6β-OH | —H | m.p.: 103–104° C. |
| 68 | —H | -Me | 4aα-Me | —CH$_2$—CH$_2$—CH=CH$_2$ | 6β-OH | —CO—O-Allyl | 362(M$^+$, 13) |

TABLE 27-continued
Examples of compounds of the formula (I-1)
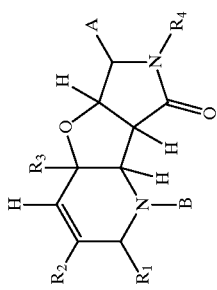
(I-1)
| Ex. No. | R¹ | R² | R³ | R⁴ | A | B | Physical data* |
|---|---|---|---|---|---|---|---|
| 69 | —H | -Me | 4α-Me | CH₂=C(CH₃)-CH₂-CH₂-CH₃ | 6β-OH | —CO—O-Allyl | m.p.: 85–86° C. |
| 70 | —H | -Me | 4α-Me | -Et | 6β-OH | —CS—NH—Cpr | m.p.: 84–86° C. |
| 71 | —H | -Me | 4α-Me | -Et | 6β-OH | —CS—NH—Allyl | m.p.: 170–172° C. |
| 72 | —H | -Me | 4α-Me | -Et | 6β-OH | —CO—Cpr | 320 (M⁺, 50) |
| 73 | —H | -Me | 4α-Me | -Et | 6β-OH | —CO—(4-Cl-C₆H₄) | 390 (M⁺, 42) |
| 74 | —H | -Me | 4α-Me | -Et | 6β-OH | —CO—O-Vinyl | m.p.: 71–75° C. |
| 75 | —H | -Me | 4α-Me | -Et | 6β-OH | —CO—O-iBu | 352 (M⁺, 18) |
| 76 | —H | -Me | 4α-Me | -Et | 6β-OH | —CO—O—(4-MeO-C₆H₄) | 402 (M⁺, 15) |
| 77 | —H | -Me | 4α-Me | -Et | 6β-OH | —CO—O-tBu | m.p.: 142–144° C. |

TABLE 27-continued
Examples of compounds of the formula (I-1)
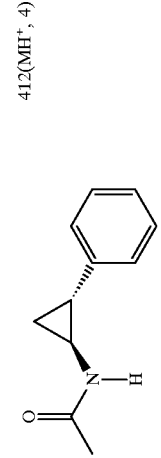
(I-1)
| Ex. No. | R[1] | R[2] | R[3] | R[4] | A | B | Physical data* |
|---|---|---|---|---|---|---|---|
| 78 | —H | -Me | 4aα-Me | 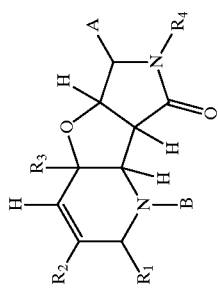 | 6β-OH | —H | 367 (M+, 20) |
| 79 | —H | -Me | 4aα-Me | 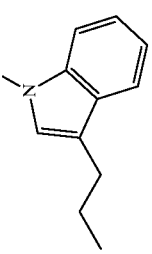 | 6β-OH | —CO—O-Allyl | m.p.: 145° C. |
| 80 | —H | -Me | 4aα-Me | -Et | 6β-OH | 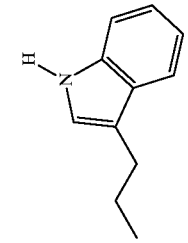 | 412(MH+, 4) |

TABLE 27-continued
Examples of compounds of the formula (I-1)
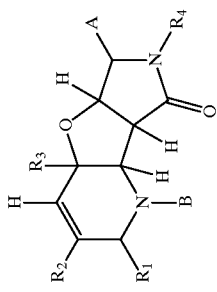
(I-1)
| Ex. No. | R¹ | R² | R³ | R⁴ | A | B | Physical data* |
|---|---|---|---|---|---|---|---|
| 81 | —H | -Me | 4aα-Me | indol-3-yl-propyl | 6β-O—Ac | —CO—O-Allyl | m.p.: 145° C. |
| 82 | —H | -Me | 4aα-Me | -Me | 6α-(5-methyl-2-TMS-furyl) | —CO—O-Allyl | 445 (M⁺, 100) |
| 83 | —H | -Me | 4aα-Me | -Et | 6α/6β-OH | —C(=S)—CH₂—N(H)—CH₂CH₂-morpholine | m.p.: 64–67° C. |

TABLE 27-continued
Examples of compounds of the formula (I-1)
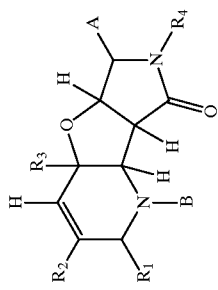
(I-1)
| Ex. No. | R¹ | R² | R³ | R⁴ | A | B | Physical data* |
|---|---|---|---|---|---|---|---|
| 84 | —H | -Me | 4α-Me | -Et | 6β-OH | 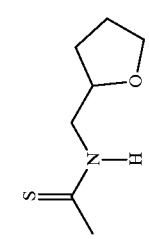 | m.p.: 160–62° C. |
| 85 3422 | —H | -Me | 4α-Me | -Et | 6β-OH | 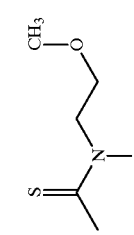 | m.p.: 180° C. |
| 86 3423 | —H | -Me | 4α-Me | -Et | 6β-OH | —CS—NH-iBu | m.p.: 121–23° C. |
*Analytical methods: LC/MS (acidic); EI-MS m/z (%), ¹H NMR (300 MHz, CDCl₃, δ), ¹³C NMR (150 MHz, CDCl₃, δ);

Abbreviations: Ac: -acetyl; allyl: —CH₂—CH=CH₂; Bu: -butyl; Bn: -benzyl; Boc: tert-butyloxy-carbonyl; Cpm: cyclopropylmethyl; Et: -ethyl; Me: -methyl; MeLeu: N-methyl-N-leucine; vinyl: —CH=CH₂; Cpr: cyclopropyl; Ph: -phenyl; Pnp: para-nitrophenyl; Z: benzyloxycarbonyl; i-, s- and t-: iso, secondary and tertiary; TMS: trimethylsilyl (—SiMe₃)

TABLE 28

Examples of compounds of the formula (I-2)

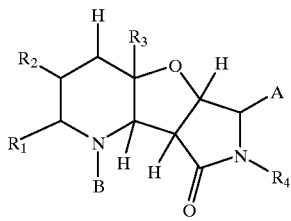

(I-2)

| Ex. No. | $R^1$ | $R^2$ | $R^3$ | $R^4$ | A | B | Physical data* |
|---|---|---|---|---|---|---|---|
| 87 | —H | 3α-Me | 4aα-Me | -Et | 6β-OH | —CO—O-Allyl | 338 (M⁺, 35) |
| 88 | —H | 3α-Me | 4aα-Me | -Me | 6β-OH | —CO—O-Allyl | m.p.: 113–114° C. |
| 89 | —H | 3β-Me | 4aα-Me | -Me | 6β-O-Et | —CO—O-Allyl | 352 (M⁺, 8) |
| 90 | —H | 3β-Me | 4aα-Me | -Et | 6β-OH | —CS—NH—Cpm | 368 (M⁺, 10) |
| 91 | —H | 3β-Me | 4aα-Me | -Me | 6α/6β-OH (89:11) | —CS—NH—Cpm | m.p.: 135–137° C. |

*Analytical methods: LC/MS (acidic); EI-MS m/z (%), ¹H NMR (300 MHz, CDCl₃, δ) in [ppm]

Abbreviations: Ac: -acetyl; allyl: —CH₂—CH=CH₂; Bu: -butyl; Me: -methyl; Ph: -phenyl; Pr: -propyl; i-, s- and t-: iso, secondary and tertiary, Et: -ethyl; Cpm: -cyclopropylmethyl

What is claimed is:

1. 6-Substituted 1,2,4a,5a,8a,8b-hexahydro- and 1,2,3,4,4a,5a,8a,8b-octahydro-6H-pyrrolo[3',4':4,5]furo[3,2-b]pyrid-8(7H)-one compound of the formula (I) or a pharmaceutically acceptable salt thereof

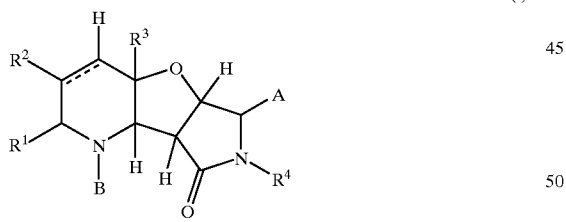

(I)

in which $R^1$ represents hydrogen, straight-chain or branched alkyl, cycloalkyl, arylalkyl, aryl, heteroaryl, or hetarylalkyl, which is optionally substituted, $R^2$ represents hydrogen, straight-chain or branched alkyl, cycloalkyl, or alkoxycarbonyl, which Is optionally substituted, $R^1$ and $R^2$ together with the atoms to which they are attached represent a 5- or 6-membered ring which Is optionally interrupted by oxygen, sulphur, sulphoxyl or sulphonyl and which is optionally substituted, $R^3$ represents hydrogen, straight-chain or branched alkyl, cycloalkyl or alkoxycarbonyl, which is optionally substituted, $R^4$ represents hydrogen, straight-chain or branched alkyl, alkenyl, alkinyl, cycloalkyl, cycloalkylalkyl, aryl, arylalkyl, hetaryl, hetarylalkyl, amino, alkylamino, dialkylamino, or cycloalkylamino, which is optionally substituted, A represents hydroxyl, alkoxy, alkenyloxy, alkinyloxy, arylalkyloxy, formyloxy, azido, halogen, aryloxy, hetarylalkyloxy, hetaryloxy, mercapto, alkylthio, alkylsulphonyl, alkenylthio, alkenylsulphonyl, alkinylthio, alkinylsulphonyl, arylalkylthio, arylalkylsulphonyl, hetarylalkylthio, hetarylalkylsulphonyl, arylthio, arylsulphonyl, alkyl, alkenyl, alkinyl, aryl, arylalkyl, hetaryl, hetarylalkyl, or alkoxycarbonyl, which is optionally substituted, or cyano, carbamoyl, thiocarbamoyl, or optionally represents a radical from the group consisting of $A^1$, $A^2$ and $A^3$

(A¹)

(A²)

(A³)

in which

X represents oxygen or sulphur,

represents carboxyl, thiocarboxyl, sulphoxyl, sulphonyl, —P(O)—O—$R^5$ or —P(S)—O—$R^5$, Q represents straight-chain or branched alkyl, alkenyl, alkinyl, cycloalkyl, alkoxy, alkenyloxy, alkinyloxy, aryl, arylalkyl, cycloalkoxy, hetaryl, hetarylalkyl, or a cyclic amino group which is attached via nitrogen and which is optionally substituted, $R^5$ represents alkyl, $R^6$ represents hydrogen, alkyl, alkoxy, arylalkoxy, alkylthio, cycloalkylthio, arylthio, or hetarylalkylthio, $R^7$ represents alkyl, alkenyl, cycloalkyl, alkylthio, arylthio, aryl, arylalkyl, hetaryl or hetarylalkyl, which is optionally substituted, $R^6$ and $R^7$ together with the atoms to which they are attached represent a 5-, 6 or 7-membered carbocyclic ring, which is optionally substituted, B represents hydrogen, straight-chain or branched alkyl, alkenyl, alkinyl, cycloalkyl, cycloalkylalkyl, aryl, arylalkyl, hetaryl, or hetarylalkyl, which is optionally substituted, formyl, alkoxydicarbonyl or optionally represents a radical from the group consisting of $B^1$, $B^2$, $B^3$ and $B^4$

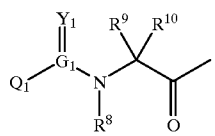 (B$^1$)

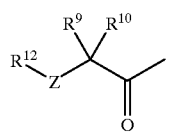 (B$^2$)

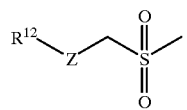 (B$^3$)

 (B$^4$)

in which $R^8$ represents hydrogen, straight-chain or branched alkyl, cycloalkyl, aryl, arylalkyl, heteroaryl, or heteroarylalkyl, which is optionally substituted, $R^8$ and $R^9$ together with the atoms to which they are attached represent a 5- or 6-membered ring which is optionally interrupted by oxygen, sulphur, sulphoxyl or sulphonyl and is optionally substituted, $R^9$ and $R^{10}$ independently of one another each represent hydrogen, straight-chain or branched alkyl, alkenyl, cycloalkyl, optionally substituted aryl, arylalkyl, hetaryl, or hetarylalkyl, or $R^9$ and $R^{10}$ together represent a spirocyclic ring, which is optionally substituted,

represents carboxyl, thiocarboxyl, —C=CH—$NO_2$, —C=CH—CN, —C=N—$R^{11}$, sulphoxyl, sulphonyl, —P(O)—O—$R^5$ or —P(S)—O—$R^5$, $R^{11}$ represents hydrogen, hydroxyl, alkoxy, alkylcarbonyl, alkoxycarbonyl, halogenoalkylcarbonyl, alkylsulphonyl, nitro or cyano, and $Q^1$ represents straight-chain or branched alkyl, alkenyl, alkinyl, cycloalkyl, aryl, arylalkyl, hetaryl or hetarylalkyl, which is optionally substituted, or a radical from the group consisting of $G^1$ and $G^2$

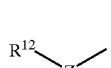 (G$^1$)

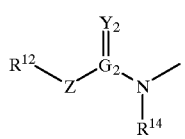 (G$^2$)

in which

may represent carboxyl, thiocarboxyl or sulphonyl,

Z represents oxygen, sulphur or —$NR^{13}$, $R^{12}$ represents a cyclic amino group which is attached via a nitrogen atom, if Z is nitrogen, $R^{12}$ and $R^{13}$ independently of one another represent hydrogen, straight-chain or branched alkyl, alkenyl, alkinyl, cycloalkyl, cycloalkyl-alkyl, alkoxycarbonyl, aryl, arylalkyl, hetaryl, or hetarylalkyl, which is optionally substituted, or $R^{12}$ and $R^{13}$ together with the adjacent N atom represent a heterocyclic 5-, 6- or 7-membered ring system or a 7- to 10-membered bicyclic ring system, which is optionally interrupted by oxygen, sulphur, sulphoxyl, sulphonyl, carbonyl, —N—O, —N=, —$NR^{15}$— or by quarternized nitrogen and which is optionally substituted, $R^{14}$ represents hydrogen or alkyl, $R^{15}$ represents hydrogen, straight-chain or branched alkyl, alkenyl, alkinyl, cycloalkyl, cycloalkylalkyl, alkoxycarbonyl, alkylcarbonyl, cycloalkylcarbonyl, cyano, aryl, arylalkyl, hetaryl, or hetarylalkyl, which is optionally substituted.

2. A process for preparing the novel 6-hydroxy-1,2,4a,5a,8a,8b-hexahydro-6H-pyrrolo[3',4':4,5]furo[3,2-b]pyrid-8(7H)-one and/or 6-hydroxy-1,2,3,4,4a,5a,8a,8b-octahydro6H-pyrrolo[3',4:4,5]furo[3,2-b]pyrid-8(7H)-one compound as recited in claim 1 having the formulae (Ia) and (Ib) or pharmaceutically acceptable salts thereof (Ia)

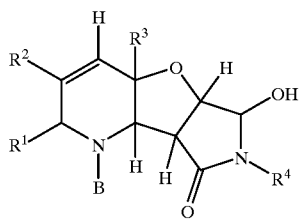

(Ib)

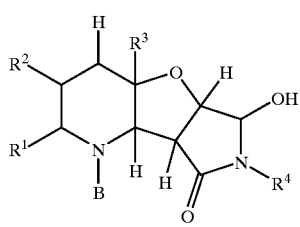

in which

R¹, R², R³, R⁴ and B are each as defined in claim 1, comprising hydrogenating 1,2,4a,5a,8a,8b-hexahydro-6H-pyrrolo[3',4':4,5]furo[3,2-b]pyridine-6,8(7H)-dione and/or 1,2,3,4,4a,5a,8a,8b-octahydro-6H-pyrrolo[3',4':4,5]furo[3,2-b]pyridine-6,8(7H)-dione compound of the formulae (IIa) and (IIb) or a pharmaceutically acceptable salt thereof (IIa)

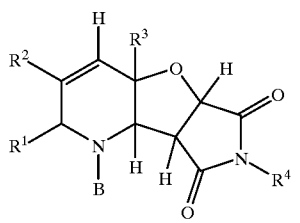

(IIb)

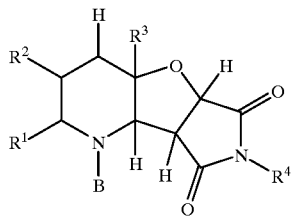

in which

R¹, R², R³, R⁴ and B are each as defined in claim 1 in the presence of a diluent, or hydrogenating 1,2,4a,5a,8a,8b-hexahydro-6H-pyrrolo[3',4':4,5]furo[3,2-b]pyridine-6,8(7H)-dione and/or 1,2,3,4,4a,5a,8a,8b-octahydro-6H-pyrrolo[3',4':4,5]furo[3,2-b]pyridine-6,8(7H)-dione compound of the formulae (IIc) and (IId) or a pharmaceutically acceptable salt thereof (IIc)

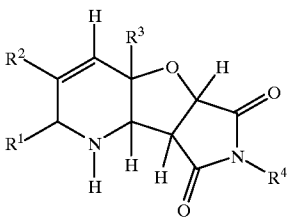

(IId)

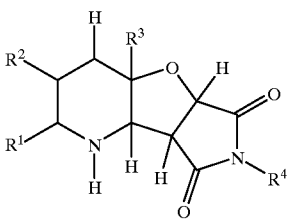

in which

R¹, R², R³ and R⁴ are each as defined in claim 1 in the presence of a diluent to give 6-hydroxy-1,2,4a,5a,8a,8b-hexahydro-6H-pyrrolo[3',4':4,5]furo[3,2-b]pyrid-8(7H)-one and/or 6-hydroxy-1,2,3,4,4a,5a,8a,8b-octahydro-6H-pyrrolo[3',4':4,5]furo[3,2-b]pyrid-8(7H)-one compound of the formulae (Ic) and (Id)

(Ic)

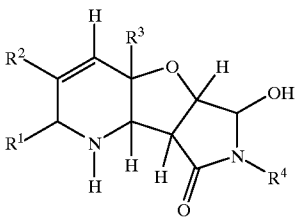

(Id)

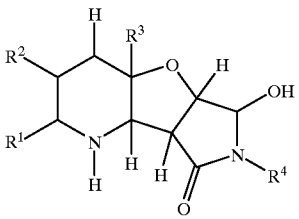

in which

R¹, R², R³ and R⁴ are each as defined in claim 1, or hydrogenating in a first reaction step the 4a,5a,8a,8b-tetrahydro-6H-pyrrolo[3',4':4,5]furo[3,2-b]pyridine6,8(7H)-dione compound of the formula (III) and their salts (III)

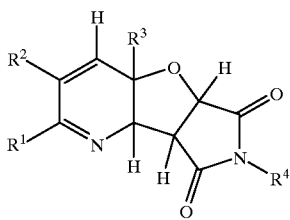

in which
R$^1$, R$^2$, R$^3$ and R$^4$ are each as defined in claim 1 in the presence of a diluent to give 6-hydroxy-1,2,4a,5a,8a,8b-hexahydro-6H-pyrrolo[3',4':4,5]furo[3,2-b]pyrid-8 (7H)-one compound of the formula (Ic)

(Ic)

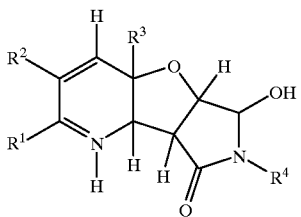

in which
R$^1$, R$^2$, R$^3$ and R$^4$ are each as defined in claim 1, and, subsequently in a second reaction step, reacting the compound of the formulae (Ic) and (Id)

(Ic)

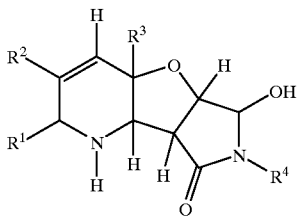

(Id)

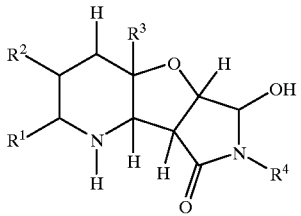

in which
R$^1$, R$^2$, R$^3$ and R$^4$ are each as defined in claim 1, with
a) a compound of the formula (IV)

B—E  (IV)

in which
B is as defined above, and
E represents an electron-withdrawing leaving group, optionally in the presence of diluents or a basic reaction auxiliary, or with b) a compound of the formula (V)

(V)

in which

and Q are each as defined in claim 1, and
W represents a leaving group, which is a halogen, alkoxy, alkylthio or aryloxy,
and optionally in the presence of a catalyst, a basic reaction auxiliary or a diluent, to prepare the novel 6-hydroxy-1,2,4a,5a,8a,8b-hexahydro-6H-pyrrolo[3',4':4,5]furo[3,2-b]pyrid-(7H)-one and/or 6-hydroxy 1,2,3,4,4a,5a,8a,8b-octahydro-6H-pyrrolo[3',4':4,5]furo[3,2-b]pyrid-(7H)-one compound of the formulae (Ia) and (Ib) and their salts in which the group

represents carboxyl, or with
c) a carboxylic anhydride of the formula (VI)

(Q—C=O)$_2$O  (VI)

in which
Q is as defined under claim 1, optionally in the presence of a catalyst, in the presence of diluents, with
d) amino acid derivatives of the formula (VII)

(VII)

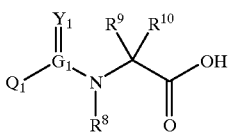

in which

Q$^1$, R$^8$, R$^9$ and R$^{10}$ are as defined in claim 1, optionally in the presence of coupling agents and in the presence of a basic reaction auxiliary, in the presence of diluents, or with
e) compounds of the formulae (VIII) or (IX)

(VIII)

R$^{12}$—N=C=Y

-continued

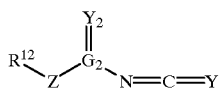
(IX)

in which

Z and $R^{12}$ are each as defined in claim 1,

Y represents oxygen or sulphur, optionally in the presence of a catalyst, or a diluent.

3. A process for preparing 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro6H-pyrrolo[3',4':4,5]furo[3,2-b]pyrid-8(7H)-one compound as recited in claim 1 having the formulae (Ie) and (If) or a pharmaceutically acceptable salt thereof

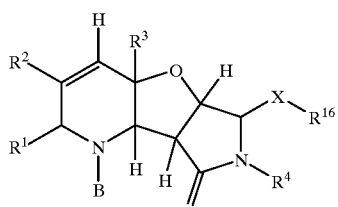
(Ie)

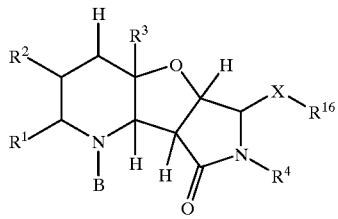
(If)

in which $R^1$, $R^2$, $R^3$, $R^4$ and B are each as defined in claim 1,

X represents oxygen, sulphur or sulphonyl, $R^{16}$ represents alkyl, alkenyl, alkinyl, arylalkyl, aryl, hetarylalkyl, or hetaryl, which is optionally substituted, or the group

in which

G, Y and Q are each as defined in claim 1, and their optical isomers and racemates, comprising:

a) reacting compounds of the formulae (Ia) and (Ib) obtainable according to claim 2 or a pharmaceutically acceptable salt thereof

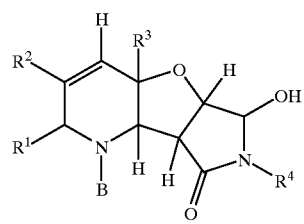
(Ia)

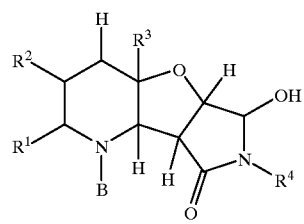
(Ib)

in which $R^1$, $R^2$, $R^3$, $R^4$ and B are each as defined in claim 1 with compounds of the formula (X)

$$H\text{—}X\text{—}R^{16} \qquad (X)$$

in which $R^{16}$ and X are each as defined above, optionally in the presence of an acid, or a diluent, or b) preparing novel 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one compound of the formulae (Ie) and (If) and their salts, in which the radical $R^{16}$ represents the group

in which

and Q are each as defined in claim 1, comprising reacting them with the compounds of the formula (V)

(V)

in which

and Q are each as defined in claim 1, optionally in the presence of a catalyst, a basic reaction auxiliary or a diluent, or c) preparing the novel compound of the formulae (Ie) and (If) and their salts or a pharmaceutically acceptable salt thereof,
in which the group

represents carboxyl, comprising reacting them with a carboxylic anhydride of the formula (VI)

(Q—C=O)$_2$O  (VI)

in which
Q is as defined in claim 1, optionally in the presence of a catalyst, or a diluent, or
d) comprising reacting them with compounds of the formulae (VII) or (IX)

R$^{12}$—N=C=Y  (VIII)

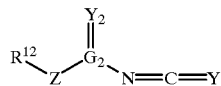  (IX)

in which

Z, Y and R$^{12}$ are each as defined under claim 1, optionally in the presence of a catalyst, or a diluent, or
e) preparing the novel 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one compound of the formulae (Ie) and (If) or pharmaceutically acceptable salt thereof

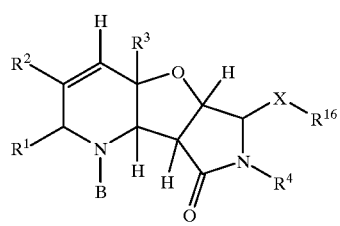  (Ie)

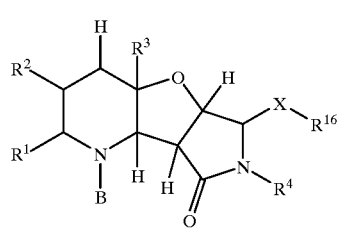  (If)

in which
R$^1$, R$^2$, R$^3$, R$^4$, X and B are as defined in claim 1 and the radicals B and R$^{16}$ represent the same group

in which

and Q are each as defined in claim 1, compounds of the general formulae (Ic) and (Id)

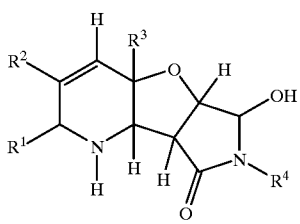  (Ic)

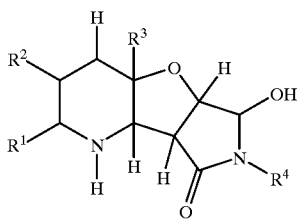  (Id)

in which
R$^1$, R$^2$, R$^3$, R$^4$ are each as defined in claim 1 comprising reacting them with acylating agents of the formula (IV)

E—B  (IV)

and/or

E—R$^{16}$ either on the radical —NH— in position 1 or on the radical —OH in position 6 or on both radicals, where E—B and/or E—R$^{16}$ are one of the compounds of the formulae (V), (VI), (VIII) or (IX) below

  (V)

(Q—C=O)$_2$O  (VI)

R$^{12}$—N=C=Y  (VIII)

-continued

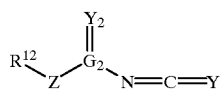 (IX)

in which

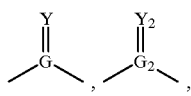

Q, Z, W and $R^{12}$ are each as defined under 1 and 2;

the reaction being carried out, optionally in the presence of a catalyst, a basic reaction auxiliary or a diluent, f) preparing the novel 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one compounds of the formulae (Ie) and (If) or a pharmaceutically acceptable salt thereof,

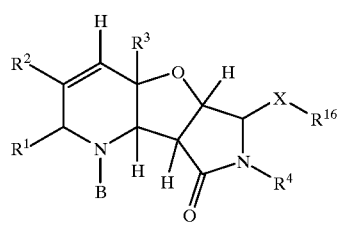 (Ie)

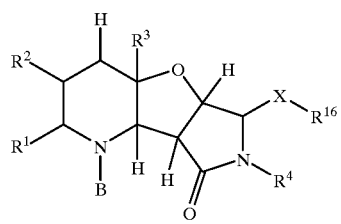 (If)

in which $R^1$, $R^2$, $R^3$, $R^4$, X and B are each as defined under claim 1 and the radical $R^{16}$ represents the group

in which

and Q are each as defined under claim 1, comprising reacting compounds of the formulae (Ic) and (Id)

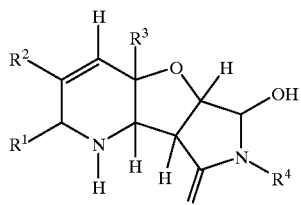 (Ic)

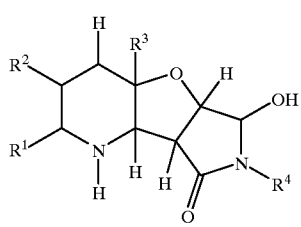 (Id)

in which $R^1$, $R^2$, $R^3$, $R^4$ are each as defined under claim 1, with an acylating agent of the formula (IV)

$$E\text{—}R^{16} \qquad (IV)$$

on the radical —OH in position 6, where $E\text{—}R^{16}$ represents the compound of the formula (VI)

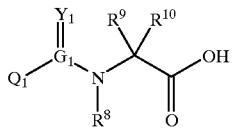 (VII)

in which

$Q^1$, $R^8$, $R^9$ and $R^{10}$ are each as defined under claims 1 and 2; and subsequently, the compounds of the formulae (Ig) and (Ih)

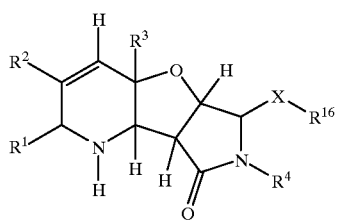 (Ig)

-continued (Ih)

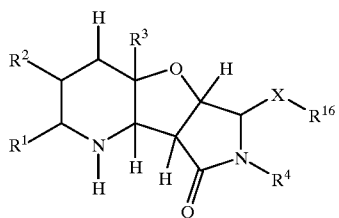

obtained in this manner in which $R^1$, $R^2$, $R^3$, $R^4$ and X are each as defined under claim 1 and the radical $R^{16}$ represents the group

in which

and Q are each as defined under claim 1, with an acylating agent of the formula (IV)

E—B     (IV)

on the radical —NH— in position 1, where E—B is one of the compounds of the formulae (V), (VI), (VII) or (IX) in which

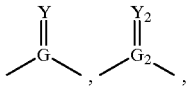

Q, Z, W, and $R^{12}$ are each as defined under claims 1 and 2;

the reaction being carried out, optionally, in the presence of a catalyst, a basic reaction auxiliary or a diluent.

4. A process for preparing the 6-substituted 1,2,4a,5a,8a,8b-hexahydro-6H-pyrrolo[3',4':4,5]furo[3,2-b]pyrid-8(7H)-one and/or 6-substituted 1,2,3,4,4a,5a,8a,8b-octahydro-6H-pyrrolo[3',4':4,5]furo[3,2-b]pyrid-8(7H)-one compound as recited in claim 1 having the formulae (Ii) and (Ij) or a pharmaceutically acceptable salt thereof (Ii)

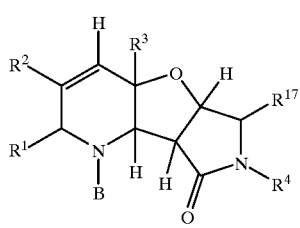

(Ij)

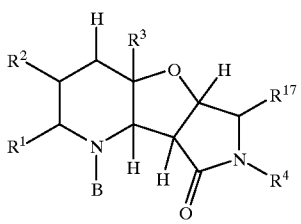

in which $R^1$, $R^2$, $R^3$, $R^4$ and B are each as defined in claim 1, $R^{17}$ represents alkyl, alkenyl, alkinyl, aryl, arylalkyl, hetaryl, hetarylalkyl, cyano, alkoxycarbonyl, carbamoyl, thiocarbamoyl, which are optionally substituted, or a radical from the group $A^2$

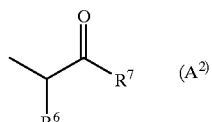

in which $R^6$ and $R^7$ are each as defined above in claim 1, and their optical isomers and racemates, comprising reacting either of the compounds of the formulae (Ia) and (Ib)

(Ia)

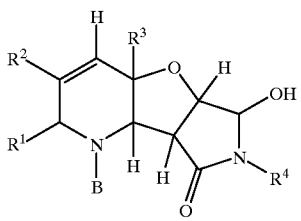

(Ib)

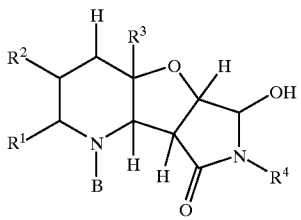

in which $R^1$, $R^2$, $R^3$, $R^4$ and B are each as defined in claim 1, with a) organometallic compounds of the formula (XI)

$(R^{18})_3M—R^{17}$     (XI)

in which $R^{18}$ represents $C_{1-4}$-alkyl,

M represents a metal atom, in particular silicon or tin, $R^{17}$ represents alkyl, alkenyl, cycloalkenyl, alkinyl, arylalkyl, hetarylalkyl, which are optionally substituted, or cyano, optionally in the presence of diluents or a catalyst, or b) with compounds of the formula (XII)

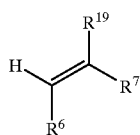 (XII)

in which

R$^6$ and R$^7$ are each as defined above,

R$^{19}$ represents hydrogen, —O-acyl, —O—Sn—O—SO$_2$—CF$_3$, —O—B(CH$_2$—CH$_3$)$_2$, or represents the radicals —O—M(R$^{18}$)$_3$ and

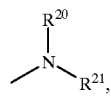

in which

M and R$^{18}$ are each as defined above, and

R$^{20}$ and R$^{21}$ independently of one another each represent hydrogen, straight-chain or branched alkyl, alkenyl, alkinyl, cycloalkyl, cycloalkylalkyl, arylalkyl, which are optionally substituted, or R$^{20}$ and R$^{21}$ together with the adjacent N atom represent a heterocyclic 5-, 6- or 7-membered ring system, which is optionally interrupted by oxygen, sulphur or nitrogen and which is optionally substituted, optionally in the presence of a catalyst or a diluent, or with c) aromatics or heteroaromatics of the formula (XIII)

 (XIII)

in which

R$^{17}$ represents aryl or hetaryl, which is optionally substituted, optionally in the presence of a catalyst and or a diluent.

5. An endoparasitical composition comprising at least one 6-substituted 1,2,4a,5a,8a,8b-hexahydro- or 1,2,3,4,4a,5a,8a,8b-octahydro6H-pyrrolo[3',4':4,5]furo[3,2-b]pyrid-8(7H)-one compound according to claim 1.

6. A process for preparing an endoparasiticidal composition comprising a 6-substituted 1,2,4a,5a,8a,8b-hexahydro- or 1,2,3,4,4a,5a,8a,8b-octahydro6H-pyrrolo[3',4':4,5]furo[3,2-b]pyrid-8(7H)-one compound according to claim 1 comprising mixing said compound with extenders and/or surfactants.

7. A method of controlling pathogenic endoparasites in a human or an animal comprising administering to the human or animal in need thereof an effective amount of an endoparasitical composition comprising a 6-substituted 1,2,4a,5a,8a,8b-hexahydro- or 1,2,3,4,4a,5a,8a,8b-octahydro-6H-pyrrolo[3',4':4,5]furo[3,2-b]pyrid-8(7H)-one compound according to claim 1.

8. The process of claim 4 wherein the compound has formula (Ie) or (If)

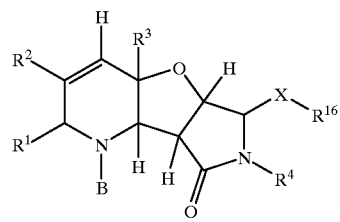 (Ie)

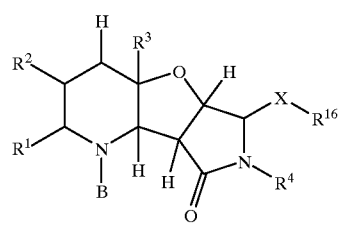 (If)

which is prepared as recited in claim 3, in which

R$^1$, R$^2$, R$^3$, R$^4$ and B are each as defined in claim 3 and

R$^{16}$ represents alkyl, arylalkyl, aryl or acyl, which are optionally substituted, X represents oxygen, sulphur or sulphonyl.

* * * * *